United States Patent [19]

Baxter et al.

[11] Patent Number: 5,670,489

[45] Date of Patent: Sep. 23, 1997

[54] OLIGONUCLEOTIDE ANALOGUES

[75] Inventors: Anthony David Baxter, Northwich; Eric Keith Baylis, Stockport; Stephen Paul Collingwood, Westhoughton; Roger John Taylor, Stretford, all of England; Alain De Mesmaeker, Kanerkinden; Chantal Schmit, Basel, both of Switzerland

[73] Assignee: Novartis Corporation, Summit, N.J.

[21] Appl. No.: 463,139

[22] Filed: Jun. 2, 1995

Related U.S. Application Data

[62] Division of Ser. No. 204,020, Feb. 28, 1994.

[30] Foreign Application Priority Data

Mar. 6, 1993 [GB] United Kingdom ............... 9304618

[51] Int. Cl.$^6$ ............................. A61K 31/70; C07H 21/04
[52] U.S. Cl. ........................... 514/44; 536/24.5; 536/25.6; 435/6
[58] Field of Search ................. 514/44; 516/24.5; 435/6

[56] References Cited

U.S. PATENT DOCUMENTS 5,466,677   11/1995   Baxter et al. ..................... 514/44

FOREIGN PATENT DOCUMENTS

| | | |
|---|---|---|
| 477454 | 1/1992 | European Pat. Off. |
| 479640 | 4/1992 | European Pat. Off. |
| 9115499 | 10/1991 | WIPO |
| 9202534 | 2/1992 | WIPO |
| 9213869 | 8/1992 | WIPO |
| 9220697 | 11/1992 | WIPO |

OTHER PUBLICATIONS

Padyukova et al.(I), "A New Synthetic Route to Phosphonate Analogs of 5'-Nucleotides," *Bioorg. Khim.*, 13(5), 706–707 (1987); *Chem. Abstr.*, 108(19), p. 691, Abstr. No. 167857v ((1988).

Mikhailov et al., "Use of 5-Deoxy-ribo-hexofuranose Derivatives for the Preparation m of 5'-Nucleotide Phosphonates and Homoribonucleosides," *Collect. Czech. Chem. Comm.*, 54, 1055–1066 (1989).

Padyukova et al.(II), "A New Scheme for the Synthesis of 5'-Nucleotide Phosphonate Analogs," *Tett. Lett.*, 28(31), 3623–3626 (1987).

Breaker et al., "Synthesis and Properties of Adenosine Oligonucleotide Analogues Containing Methylene Groups in Place of Phosphodiester 5'-Oxygens," *Biochemistry*, 32(35), 9125–9128 (1993).

Marquez et al., "Thiazole-4-carboxamide Adenine Dinucleotide (TAD). Analogues Stable to Phosphodiesterase Hydrolysis," *J. Med. Chem.*, 29(9), 1726–1731 (1986).

Buhr et al., "Methylenephosphonate Nucleoside Analogs and Oligonucleotide Analogs Made Therefrom," *Chem. Abstr.*, 118(1), p. 780, Abstr. No. 7326z (1993); see patent reference 'L' for the complete publication.

*Primary Examiner*—John Kight
*Assistant Examiner*—L. Eric Crane
*Attorney, Agent, or Firm*—George R. Dohmann

[57] ABSTRACT

A dinucleotide analogue of formula

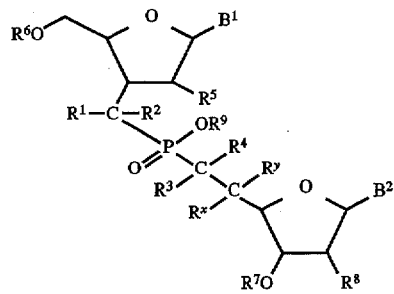

I where $B^1$ and $B^2$ are each independently a monovalent nucleoside base radical;

$R^1$ is $R^1_a$ or Z;

$R^1_a$, $R^2$, $R^3$ and $R^4$ are each independently hydrogen, halogen or hydroxy;

$R^5$ is $R^5_a$ or Z;

$R^6$ is hydrogen or $R^6_a$;

$R^7$ is hydrogen, alkyl-N,N-dialkylphosphoramidyl or $R^7_a$, $R^8$ is $R^8_a$ or Z, or the indicated $R^7O$ and $R^8$ together denote an isopropylidenedioxy group;

$R^5_a$ and $R^8_a$ are each independently hydrogen, halogen, hydroxy, $—OR^{10}$, $—OCOR^{10}$ or silyloxy substituted by three $C_1$–$C_5$ hydrocarbyl groups;

$R^6_a$ and $R^7_a$ are each independently a $C_1$–$C_{10}$ aliphatic radical, a $C_6$–$C_{15}$ aromatic radical, a $C_7$–$C_{30}$ araliphatic radical, $—COR^{11}$, $—SO_2R^{11}$ or silyl substituted by three $C_1$–$C_{15}$ hydrocarbyl groups;

$R^9$ is hydrogen, a $C_1$–$C_8$ aliphatic radical, a $C_3$–$C_8$ cycloaliphatic radical, a $C_6$–$C_{15}$ aromatic radical, a $C_7$–$C_{13}$ araliphatic radical, an alkali metal ion or an ammonium ion;

$R^{10}$ and $R^{11}$ are each independently a $C_1$–$C_{10}$ aliphatic radical, a $C_3$–$C_8$ cycloaliphatic radical, a $C_6$–$C_{15}$ aromatic radical or a $C_7$–$C_{16}$ araliphatic radical;

$R^x$ and $R^y$ are independently hydrogen, halogen, hydroxy, a $C_1$–$C_{10}$ alkyl, $C_2$–$C_{10}$ alkenyl, $C_3$–$C_8$ cycloalkyl, $C_6$–$C_{15}$ aryl, $C_7$–$C_{16}$ aralkyl, $C_1$–$C_{10}$ alkoxy, $C_2$–$C_{10}$ alkenoxy, $C_6$–$C_{10}$ aryloxy or $C_7$–$C_{16}$ aralkyloxy group, which is substituted or unsubstituted, or $—OCOR_z$;

$R^z$ is a substituted or unsubstituted $C_1$–$C_{10}$ alkyl, $C_2$–$C_{10}$ alkenyl, $C_3$–$C_8$ cycloalkyl, $C_6$–$C_{15}$ aryl or $C_7$–$C_{16}$ aralkyl group; and Z is $C_6$–$C_{10}$ aryloxythiocarbonyloxy, the $C_6$–$C_{10}$ aryl group being substituted or unsubstituted.

14 Claims, No Drawings

OLIGONUCLEOTIDE ANALOGUES

This is a divisional of Ser. No. 08/204,020, filed Feb. 28, 1994.

This invention relates to compounds which are dinucleotide analogues, their preparation and to oligonucleotide analogues incorporating units derived therefrom.

For several years there has been interest in structural analogues of natural oligonucleotides because of their utility as anti-sense probes for inhibiting gene expression in biological systems and as pharmaceuticals in the treatment of viruses such as influenza, herpes and HIV, and in the treatment of cancer. Amongst the analogues of recent interest are those in which the groups linking the sugar moieties of oligonucleotides are modified by the replacement of the $3^1$ and $5^1$ oxy linkages by other linking groups.

WO 91/15499 describes oligonucleotides of formula

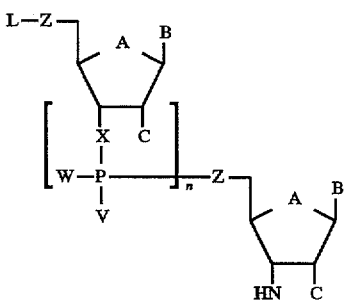

where B is a nucleic acid base; A is —O— or —CH$_2$—; X and Z are each —O—, —S—, —NH— or —CH$_2$— where X and Z may be the same or different; V and W are =O, =S, =Se, —NH$_2$, alkoxy, —OH or —SH, where V and W may be the same or different in a monomer unit; L is —H or a partner of a bonding pair; C is —OR where R is an alkyl, alkenyl or alkynyl group optionally substituted by one or more halogen, cyano, carboxy, hydroxy, nitro and/or mercapto radicals; and n is any integer.

No compounds of the above formula where X and Z are each —CH$_2$— are disclosed in WO 91/15499 and there is no suggestion as to how such compounds might be prepared. The preparation of oligonucleotide analogues in which both the $3^1$ oxy linkage and the $5^1$ oxy linkage are replaced by carbon linkages has remained a significant problem. A method for the preparation of such oligonucleotide analogues has now been found. The resulting novel compounds have good stability towards nuclease hydrolysis and good hybridisation properties, facilitating their use as anti-sense probes and as pharmaceuticals for the treatment of viruses such as influenza, herpes and HIV.

Accordingly, the present invention provides a dinucleotide analogue of formula

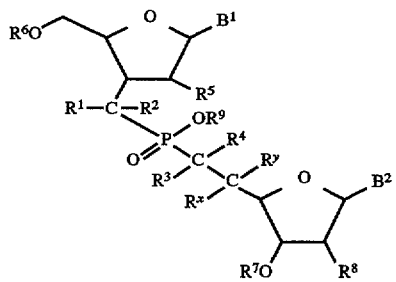   I where $B^1$ and $B^2$ are each independently a monovalent nucleoside base radical;

$R^1$ is $R^1_a$ or Z, $R^1_a$, $R^2$, $R^3$ and $R^4$ are each independently hydrogen, halogen or hydroxy;

$R^5$ is $R^5_a$ or Z;

$R^6$ is hydrogen or $R^6_a$;

$R^7$ is hydrogen, alkyl-N,N-dialkylphosphoramidyl or $R^7_a$, $R^8$ is $R^8_a$ or Z, or the indicated $R^7$O and $R^8$ together denote an isopropylidenedioxy group;

$R^5_a$ and $R^8_a$ are each independently hydrogen, halogen, hydroxy, —OR$^{10}$, —OCOR$^{10}$ or silyloxy substituted by three C$_1$–C$_{15}$ hydrocarbyl groups;

$R^6_a$ and $R^7_a$ are each independently a C$_1$–C$_{10}$ aliphatic radical, a C$_6$–C$_{15}$ aromatic radical, a C$_7$–C$_{30}$ araliphatic radical, —COR$^{11}$, —SO$_2$R$^{11}$ or silyl substituted by three C$_1$–C$_{15}$ hydrocarbyl groups;

$R^9$ is hydrogen, a C$_1$–C$_8$ aliphatic radical, a C$_3$–C$_{10}$ cycloaliphatic radical, a C$_6$–C$_{15}$ aromatic radical, C$_7$–C$_{13}$ araliphatic radical, an alkali metal ion or an ammonium ion;

$R^{10}$ and $R^{11}$ are each independently a C$_1$–C$_{10}$ aliphatic radical, a C$_3$–C$_8$ cycloaliphatic radical, a C$_6$–C$_{15}$ aromatic radical or a C$_7$–C$_{16}$ araliphatic radical;

$R^x$ and $R^y$ are independently hydrogen, halogen, hydroxy, a C$_1$–C$_{10}$ alkyl, C$_2$–C$_{10}$ alkenyl, C$_3$–C$_8$ cycloalkyl, C$_6$–C$_5$ aryl, C$_7$–C$_{16}$ aralkyl, C$_1$–C$_{10}$ alkoxy, C$_2$–C$_{10}$ alkenoxy, C$_6$–C$_{10}$ aryloxy or C$_7$–C$_{16}$ aralkyloxy group, which is substituted or unsubstituted, or —OCOR$^z$;

$R^z$ is a substituted or unsubstituted C$_1$–C$_{10}$ alkyl, C$_2$–C$_{10}$ alkenyl, C$_3$–C$_8$ cycloalkyl, C$_6$–C$_{15}$ aryl or C$_7$–C$_{16}$ aralkyl group; and Z is C$_6$–C$_{10}$ aryloxythiocarbonyloxy, the C$_6$–C$_{10}$ aryl group being substituted or unsubstituted.

Generally, in compounds of formula I, $R^5$ and $R^5$ are each independently hydrogen, fluorine, chlorine, hydroxy, C$_1$–C$_{10}$ alkoxy, C$_2$–C$_{10}$ alkenoxy, C$_6$–C$_{15}$ aryloxy, C$_7$–C$_{16}$ aralkyloxy, —OCOR$^{10}$ or silyloxy substituted by three C$_1$–C$_{15}$ hydrocarbyl groups;

$R^6_a$ and $R^7_a$ are each independently a substituted or unsubstituted C$_1$–C$_{10}$ alkyl, C$_2$–C$_{10}$ alkenyl, C$_6$–C$_5$ aryl or C$_7$–C$_{30}$ aralkyl group, —COR$^{11}$, —SO$_2$R$^{11}$ or silyl substituted by three C$_1$–C$_5$ hydrocarbyl groups;

$R^9$ is hydrogen, substituted or unsubstituted C$_1$–C$_8$ alkyl, C$_3$–C$_8$ cycloalkyl, C$_6$–C$_5$ aryl or C$_7$–C$_{13}$ aralkyl, an alkali metal ion or an ammonium ion; and $R^{10}$ and $R^{11}$ are each independently substituted or unsubstituted C$_1$–C$_{10}$ alkyl, C$_2$–C$_{10}$ alkenyl, C$_3$–C$_8$ cycloalkyl, C$_6$–C$_{15}$ aryl or C$_7$–C$_{16}$ aralkyl.

The compounds of formula I may be in the form of one of the possible isomers, for example as a diastereomer, an optical isomer, a racemate or a mixture thereof. Preferred isomers are those of formula

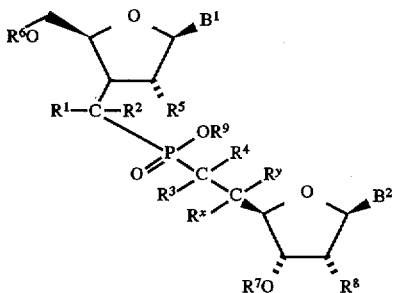

IA where $B^1$, $B^2$, $R^x$, $R^y$ and $R^1$ to $R^9$ are as hereinbefore defined.

In compounds of formula I and IA, $B^1$ and $B^2$ may be the same or different and may be radicals of bases found in naturally occurring nucleosides, such as adeninyl, cytosinyl, guaninyl, thyminyl or uracilyl, which may be unsubstituted or substituted, for example on an amino nitrogen atom by a protecting group, for example an acyl group such as acetyl, an aracyl group such as benzoyl or 4-nitrobenzoyl, or an aralkyloxymethyl group such as benzyloxymethyl, or synthetic analogues thereof. Suitable analogues of natural nucleoside bases include purines such as 2-methylthioadenine, 2-aminoadenine, 6-hydroxypurine and 2-amino-6-chloropurine, pyrindines such as 5-fluorouracil, 5-chlorouracil, 5-bromouracil, dihydrouracil and 5-methylcytosine, and derivatives thereof with protecting groups on basic nitrogen atoms. Preferably $B^1$ and $B^2$ are each a monovalent radical of a pyrimidine base, more preferably a thymine or cytosine base, especially where $B^1$ and $B^2$ are each 1-thyminyl or $B^1$ is 1-thyminyl and $B^2$ is N-benzyloxymethyl-1-thyminyl or N-acetyl-1-cytosinyl.

$R^5$ or $R^8$ as Z, i.e. as substituted or unsubstituted $C_6$–$C_{10}$ aryloxythiocarbonyloxy may for example, substituted or unsubstituted phenyloxythiocarbonyloxy, preferably $C_1$–$C_4$ alkyl- or halogen-substituted phenyloxythiocarbonyloxy, especially p-tolyloxythiocarbonyloxy or pentafluorophenoxythiocarbonyloxy.

When $R^x$, $R^y$, $R^5$ or $R^8$ denote $C_1$–$C_{10}$ alkoxy they may be, for example, methoxy, ethoxy, n-propoxy, isopropoxy, n-butoxy, isobutoxy, tert-butoxy, n-pentoxy, neopentyloxy, n-hexyloxy, n-octyloxy, 2-ethylhexyloxy, n-nonyloxy or n-decyloxy. $R^x$, $R^y$, $R^5$ or $R^8$ as alkoxy is preferably $C_1$–$C_4$ alkoxy, particularly methoxy or ethoxy.

$R^x$, $R^y$, $R^5$ or $R^8$ as $C_2$–$C_{10}$ alkenoxy may be, for example, vinyloxy, allyloxy, 1-propenyloxy, isopropenyloxy, methallyloxy, 2-butenyloxy, 1-butenyloxy, isobutenyloxy, pentenyloxy, hexenyloxy, octenyloxy or decenyloxy. Preferably, $R^x$, $R^y$, $R^5$ or $R^8$ as alkenoxy is $C_3$ or $C_4$ alkenoxy, particularly allyloxy or methallyloxy.

When $R^x$, $R^y$, $R^5$ or $R^8$ denote $C_6$–$C_{15}$ aryloxy, they may be, for example, phenoxy, o-tolyloxy, m-tolyloxy, p-tolyloxy, 2,3-dimethylphenoxy, 2,4-dimethylphenoxy, 2,5-dimethylphenoxy, alpha-naphthyloxy or beta-naphthyloxy. $R^x$, $R_y$, $R^5$ or $R^8$ as aryloxy is preferably $C_6$–$C_8$ aryloxy, particularly phenoxy.

$R^x$, $R^y$, $R^5$ or $R^8$ as aralkyloxy may be, for example, benzyloxy, 4-methylbenzyloxy, 2-phenylethoxy, 2-phenylpropoxy, 3-phenylpropoxy or diphenylmethoxy. Preferably, $R^x$, $R^y$, $R^5$ or $R^8$ as aralkyloxy is $C_7$ to $C_9$ aralkyloxy, particularly benzyloxy.

$R^5$ or $R^8$ as tri($C_1$–$C_{15}$ hydrocarbyl)-substituted silyloxy may be, for example, trialkylsilyloxy such as trimethylsilyloxy, triethylsilyloxy, tri-n-propylsilyloxy, tri-isopropylsilyloxy, tri-n-butylsilyloxy, tri-isobutylsilyloxy, tri-tert-butylsilyloxy, isopropyldimethylsilyloxy, tert-butyldimmethylsilyloxy, or 1,1,2,2-tetramethylethyldimethylsilyloxy (thexyldimethylsilyloxy), aryldialksilyloxy such as phenyldimethylsilyloxy, phenyldiethylsilyloxy, phenyldiisopropylsilyloxy or phenyl-di-tert-butylsilyloxy, or alkyldiarylsilyloxy such as isopropyldiphenylsilyloxy or tert-butyldiphenylsilyloxy. Preferably, $R^5$ or $R^8$ as tri($C_1$–$C_5$ hyarocarbyl)-substituted silyloxy is $C_1$–$C_6$ alkyldi ($C_6$–$C_8$ aryl)silyloxy, especially tert-butyldiphenylsilyloxy, or $C_2$–$C_{10}$ branched alkyl (di $C_1$–$C_4$ alkyl) silyloxy, especially thexyldimethylsilyloxy.

$R^x$, $R^y$, $R^z$, $R^6$, $R^7$, $R^{10}$ or $R^{11}$ as unsubstituted or substituted $C_1$–$C_{10}$ alkyl may be, for example, methyl, ethyl, n-propyl, isopropyl, n-butyl, isobutyl, tert-butyl, n-pentyl, neopentyl, n-hexyl, n-octyl, 2-ethylhexyl, or n-decyl, or any of these groups substituted by halogen, hydroxy or nitro. Preferably, $R^x$, $R^{y,\ Rz}$, $R^6$, $R^7$, $R^{10}$ or $R^{11}$ as $C_1$–$C_{10}$ alkyl is $C_1$ to $C_4$ alkyl, particularly methyl or ethyl.

When $R^x$, $R^y$, $R^z$, $R^6$, $R^7$, $R^{10}$ or $R^{11}$ denotes unsubstituted or substituted $C_2$–$C_{10}$ alkenyl, it may be, for example, vinyl, allyl, 1-propenyl, isopropenyl, methallyl, 2-butenyl, 1-butenyl, isobutenyl, pentenyl, hexenyl, octenyl or decyl, or any of these groups substitued by halogen, hydroxy or nitro. $R^x$, $R^y$, $R^z$, $R^6$, $R^7$, $R^{10}$ or $R^{11}$ as $C_2$–$C_{10}$ alkenyl is preferable $C_3$ or $C_4$ alkenyl, particularly allyl or methallyl.

$R^x$, $R^{y,\ Rz}$, $R^6$, $R^7$, $R^9$, $R^{10}$ or $R^{11}$ as unsubstituted or substituted $C_6$–$C_{15}$ aryl may be, for example, phenyl, o-tolyl, m-tolyl, p-tolyl, o-xylyl, m-xylyl, p-xylyl, alpha-naphthyl or beta-naphthyl, or any of these groups substituted by halogen, hydroxy, $C_1$–$C_4$ alkoxy or nitro. Preferably, $R^x$, $R^y$, $R^z$, $R^6$ or $R^7$ as $C_6$–$C_{15}$ aryl is $C_6$–$C_8$ aryl, particularly phenyl and $R^{10}$ or $R^{11}$ as $C_6$–$C_{15}$ aryl is $C_6$–$C_{10}$aryl, particularly phenyl, nitrophenyl or naphthyl.

$R^6$ or $R^7$ as substituted or unsubstituted $C_7$–$C_{30}$ aralkyl may be, for example benzyl, 2-phenylethyl, 2-phenylpropyl, 3-phenylpropyl, diphenylmethyl, triphenylmethyl or any of these groups substituted by $C_1$–$C_4$ alkyl, $C_1$–$C_4$ alkoxy, halogen or hydroxy, for example 4-methylbenzyl, methoxytriphenylmethyl or dimethoxytriphenylmethyl. Preferably $R^6$ or $R^7$ as $C_7$–$C_{30}$ aralkyl is unsubstituted or $C_1$–$C_4$ alkoxy-substituted $C_7$ to $C_{20}$ aralkyl, especially benzyl, triphenylmethyl or dimethoxytriphenylmethyl.

When $R^x$, $R^y$, $R^z$, $R^{10}$ or $R^{11}$ denotes substituted or unsubstituted $C_7$–$C_{16}$ aralkyl, it may be, for example benzyl, 4-methylbenzyl, 2-phenylethyl, 2-phenylpropyl, 3-phenylpropyl or diphenylmethyl, or any of these groups substituted by halogen, hydroxy, $C_1$–$C_4$ alkoxy or nitro. Preferably, it is $C_7$ to $C_9$ aralkyl, particularly benzyl.

$R^6$ or $R^7$ as tri($C_1$–$C_{15}$ hydrocarbyl)-substituted silyl may be, for example, trialkylsilyl such as trimethylsilyl, triethylsilyl, tri-n-propylsilyl, tri-isopropylsilyl, tri-n-butylsilyl, tri-isobutylsilyl, tri-tert-butylsilyl, isopropyldimethylsilyl tert-butyldimethylsilyl, or thexyldimethylsilyl, aryldialkylsilyl such as phenyldimethylsilyl, phenyldiethylsilyl, phenyldiisopropylsilyl or phenyl di-tert-butylsilyl, or alkyldiarylsilyl such as isopropyldiphenylsilyl or tert-butyldiphenylsilyl. Preferably $R^6$ or $R^7$ as tri($C_1$–$C_{15}$ hydrocarbyl)-substituted silyl is $C_1$–$C_6$ alkyl di($C_6$–$C_8$ aryl) silyl, especially tert-butyldiphenylsilyl, or $C_2$–$C_{10}$ branched alkyl (di $C_1$–$C_4$ alkyl) silyl, especially thexyldimethylsilyl.

$R^7$ as alkyl-N,N-dialkylphosphoramidyl may be any group of this class which is useful in activating the dinucleotide analogue of formula I for coupling at the $3^1$ position in automated synthesis of oligonucleotide analogues. The group may be, for example, $C_1$–$C_8$ alkyl-N,N-dialkylphosphoramidyl where the $C_1$–$C_8$ alkyl group is unsubstituted or substituted by cyano, $C_1$–$C_4$ alkylsulphonyl or a carboxylic ester group. Conveniently, the group is cyano-$C_1$–$C_8$ alkyl-N,N-di($C_1$–$C_8$) alkylphosphoramidyl, preferably cyano-$C_1$–$C_4$ alkyl-N,N-di($C_1$–$C_4$) alkylphosphoramidyl, especially 2-cyanoethyl-N,N-diisopropylphosphoramidyl.

$R^9$ as unsubstituted or substituted $C_1$–$C_8$ alkyl may be, for example, methyl, ethyl, n-propyl, isopropyl, n-butyl, isobutyl, tert-butyl, n-pentyl, neopentyl, n-hexyl, n-octyl or 2-ethylhexyl, preferably $C_1$–$C_6$ alkyl, particularly methyl, ethyl or isobutyl, or any of these groups substituted by $C_1$–$C_4$ alkoxy, halogen, $C_1$–$C_4$ alkylsulphonyl or cyano, for example methoxymethyl, 2-methoxyethyl, 2-ethoxyethyl, 2-butoxyethyl, 3-methoxypropyl, 4-methoxybutyl, 2-methoxy-n-butyl, 2-fluoroethyl, 2,2,2-trifluoroethyl, 2-chloroethyl, 2-chloro-n-propyl, 2-methanesulphonylethyl or, preferably, 2-cyanoethyl. $R^9$ as unsubstituted or substituted $C_7$–$C_{13}$ aralkyl may be, for example, benzyl, 4-methylbenzyl, o-methoxybenzyl, p-methoxybenzyl, diphenylmethyl, 2-phenylethyl, 2-phenylpropyl, or 3-phenylpropyl, preferably $C_7$–$C_9$ aralkyl, especially benzyl. $R^9$ as an alkali metal ion is preferably a sodium or potassium ion. $R^9$ as an ammonium ion may be an unsubstituted ammonium ion or a substituted ammonium ion, for example an alkylammonium ion such as a methylammonium, ethylammonium, n-propylammonium, isopropylammonium, n-butylammonium, isobutylammonium, tert-butylammonium, 2-hydroxyethylammonium or 3-hydroxypropylammonium, a dialkylammonium ion such as dimethylammonium, diethylammonium, di-(2-hydroxyethylammonium, methyl (2-hydroxyethyl)ammonium, di-n-propylammonium, or di-(isopropyl)ammonium, or a trialkylammonium ion such as trimethylammonium, triethylammonium, methyldiethylammonium, tri-n-butylammonium or tri(2-hydroxyethyl)ammonium.

When $R^x$, $R^y$, $R^z$, $R^9$, $R^{10}$ or $R^{11}$ denotes $C_1$–$C_4$ cycloalkyl, it may be, for example, cyclopropyl, cyclobutyl, cyclopentyl, methylcyclopentyl, cyclohexyl, methylcyclohexyl, dimethylcyclohexyl, cycloheptyl or cyclooctyl. Preferably, $R^z$, $R^y$, $R^z$, $R^9$, $R^{10}$ or $R^{11}$ as cycloalkyl is $C_6$–$C_8$ cycloalkyl, particularly cyclohexyl.

Preferred dinucleotide analogues of the invention are those of formula I, particularly the stereoisomers of formula IA, in which $B^1$ and $B^2$ are each a monovalent radical of a pyrimidine base, preferably a thymine or cytosine base, $B^1$ and $B^2$ each being 1-thyminyl or $B^1$ being 1-thyminyl and $B^2$ being N-benzyloxymethyl-1-thyminyl or N-acetyl-1-cytosinyl in especially preferred compounds, $R^1$ is hydrogen, fluorine, hydroxy or $C_1$–$C_4$ alkyl- or halogen-substituted phenyloxythiocarbonyloxy, $R^2$, $R^3$ and $R^4$ are each hydrogen, $R^5$ is hydrogen, hydroxy, or —$OCOR^{10}$ where $R^{10}$ is $C_1$–$C_4$ alkyl or $C_6$–$C_{10}$ aryl, especially preferred $R^5$ being hydrogen or —$OCOCH_3$, $R^6$ is hydrogen, —$COR^{11}$ where $R^{11}$ is $C_1$–$C_4$ alkyl or $C_6$–$C_{10}$ aryl, alkyldiarylsilyl, or unsubstituted or $C_1$–$C_4$ alkoxy-substituted $C_7$–$C_{20}$ aralkyl, especially preferred $R^6$ being hydrogen, benzoyl, tert-butyldiphenylsilyl or 4,4¹-dimethoxytriphenylmethyl, $R^7$ is hydrogen, benzyl, cyano-$C_1$–$C_4$ alkyl-N,N-di ($C_1$–$C_4$ alkyl) phosphoramidyl, especially 2-cyanoethyl-N,N-diisopropylphosphoramidyl, or —$COR^{11}$ where $R^{11}$ is $C_6$–$C_{10}$ aryl, especially where $R^{11}$ is phenyl, 4-nitrophenyl or alpha-naphthyl, $R^8$ is hydrogen, hydroxy, —$OR^{10}$ where $R^{10}$ is $C_1$–$C_4$ alkyl, especially methyl, or —$OCOR^{10}$ where $R^{10}$ is $C_1$–$C_4$ alkyl, especially methyl, or $C_6$–$C_{10}$ aryl especially phenyl, or $R^7O$ and $R^8$ together denote an isopropylidenedioxy group, $R^9$ is hydrogen or unsubstituted or substituted $C_1$–$C_6$ alkyl, especially methyl, ethyl, isobutyl or 2-cyanoethyl, and $R^x$ and $R^y$ are independently hydrogen, fluorine, methyl, ethyl or phenyl, or $R^y$ is hydrogen, methyl, ethyl or phenyl and $R^x$ is hydroxy, fluorine, methoxy, ethoxy, benzyloxy, acetoxy or benzoyloxy, $R^x$ and $R^y$ each being hydrogen in especially preferred compounds.

Dinucleotide analogues of formula I may be prepared by reaction of a compound of formula

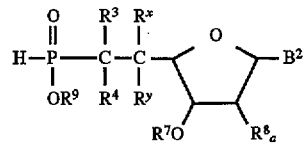

with a compound of formula

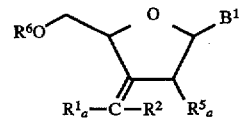

in the presence of a free radical initiator, where $B^1$, $B^2$, $R^x$, $R^y$, $R^1_a$, $R^2$, $R^3$, $R^4$, $R^5_a$, $R^6$, $R^8_a$ and $R^9$ are as hereinbefore defined and $R^7$ is hydrogen or $R^7_a$. Suitable initiators include azo compounds such as azobis(isobutyronitrile), peroxides such as benzoyl peroxide, tert-butyl peroxide or 2,2-bis(tert-butylperoxy)propane, peresters such as tert-butyl perbenzoate or tert-butyl per-2-ethylhexanoate, percarbonates such as diacetyl perdicarbonate or bis(4-tert-butylcyclohexyl) perdicarbonate or persalts such as potassium persulphate. The initiator is generally used in an amount of 0.1 to 100% mol, preferably 5 to 15, mol %, per mol of the compound of formula III.

The reaction between II and III may be carried out without a solvent, but is preferably carried out in an organic solvent, usually an aromatic hydrocarbon such as benzene, toluene or xylene. It may be carried out at temperatures of 30° to 150° C., preferably 70° to 100° C.

Dinucleotide analogues of formula I may be prepared by reaction of a compound of formula II as hereinbefore defined with a compound of formula

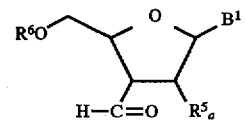

where $B^1$, $R^5_a$ and $R^6$ are as hereinbefore defined, in the presence of a base, preferably a non-nucleophilic base which may be, for example, a hindered amine such as 1,8-diazabicyclo[5.4.0]undec-7-ene or 1,5-diazabicyclo[4.3.0] non-5-ene, or an alkali metal alkoxide such as a methoxide, ethoxide or butoxide of sodium or potassium.

The reaction may be carried out at temperatures of −20° to 100° C. and is preferably carried out at ambient temperature. It is preferably effected in an inert organic solvent, for example an aromatic hydrocarbon such as benzene, toluene or xylene or, preferably, an ether, such as diethyl ether, dioxan or, especially, tetrahydrofuran.

Dinucleotide analogues of formula I may also be prepared by reaction of a compound of formula II as hereinbefore defined with a silylating agent to give a P(III) silyl compound and reacting the latter with a compound of formula IV as hereinbefore defined. The silylating agent may be, for example, a trialkylhalosilane, such as trimethylchlorosilane, or triethylchlorosilane, which is reacted with the compound of formula II in the presence of a tertiary base such as pyridine or triethylamine. The reaction between the compound of formula II and the silane may be carried out at temperatures ranging from $-20°$ C. to $150°$ C. and can be effected with or without the use of a solvent such as diethylether, tetrahydrofuran, dioxan or toluene. Alternatively, an excess of the silane can be used as diluent. The silylating agent may alternatively be hexamethyldisilazide, which may be reacted with the compound of formula II in the absence of a solvent at $100°$–$200°$ C. The reaction of the P(III) silyl compound with the compound of formula IV may be carried out under conditions conventional for substitution reactions on P(III) species. It is preferably carried out by the Arbuzov method, e.g. at temperatures between ambient and elevated temperatures such as $160°$ C., followed by hydrolysis of the resulting silyl ether.

The abovementioned reactions of a compound of formula IV with a compound of formula II or a P(III) silyl compound give a dinucleotide analogue of Formula I in which $R^1$ is hydroxy and $R^2$ is hydrogen, from which other dinucleotide analogues of formula I can be prepared by further reaction(s).

Dinucleotide analogues of formula I where $R^1$, $R^2$, $R^5$ and $R^8$ are hydrogen, which are di-2-deoxyribose analogues, can be prepared from analogues where $R^1$, $R^2$ $R^5$ and $R^8$ respectively are hydroxy by conventional deoxygenation methods, for example by reacting a compound of formula I where $R^1$ is hydroxy, $R^2$ is hydrogen, $R^3$ and $R^4$ are as hereinbefore defined, $R^5$ is hydrogen, $R^7$ is hydrogen or $R^7_a$, $R^6$ and $R^7_a$ are as hereinbefore defined, $R^8$ is hydrogen and $R^9$ is as hereinbefore defined, with a suitably substituted reagent to allow free radical mediated cleavage, such as by reaction with a substituted or unsubstituted $C_6$–$C_{10}$ aryloxythiocarbonyl chloride such as p-tolylchlorothionoformate or pentafluorophenylchlorothionoformate to convert the hydroxy group $R^1$ into a substituted or unsubstituted $C_6$–$C_{10}$ aryloxythiocarbonyloxy group, and then removing this group by reaction with a trialkylstannane such as tri-n-butylstannane, in the presence of a free radical initiator such as azobis(isobutyronitrile) or the free radical initiators hereinbefore described. Such deoxygenation can be carried out using conventional procedures. Other standard methods for the deoxygenation of alcohols are described by Hartwig, Tetrahedron 39, 2609 (1983).

Similarly, compounds of formula I where $R^5$ and/or $R^8$ are hydroxy may be converted, by reaction with an aryloxythiocarbonyl chloride as described above, into compounds of formula I where $R^5$ and/or $R^8$ are aryloxythiocarbonyloxy, which can then be reacted with a trialkylstannane in the presence of a free radical initiator to give compounds of formula I where $R^5$ and/or $R^8$ are hydrogen.

Dinucleotide analogues of Formula I where $R^6$ and/or $R^7$ are hydrogen may be prepared by hydrolysis or reduction of analogues of Formula I where $R^6$ and $R^7$ are respectively $R_{6a}$ and $R^7_a$ are as hereinbefore defined, for example using known methods for the hydrolysis of ether, ester or silyl ether groups to form hydroxyl groups. For example, a compound of formula I where $R^6$ and/or $R^7$ is a substituted silyl group as hereinbefore described may be reacted with a strong mineral acid such as hydrochloric acid or with a fluoride such as caesium fluoride or a quaternary ammonium fluoride in the presence of a carboxylic acid, usually acetic acid. In one preferred method, the compound where $R^6$ and/or $R^7$ is a substituted silyl group is reacted with tetra-n-butylammonium fluoride in the presence of acetic acid at ambient temperature to hydrolyse the group —$OR^6$ and/or —$OR^7$ to hydroxyl. A compound of formula I where $R^6$ and/or $R^7$ is an acyl group —$COR^{11}$ may be hydrolysed, for example by reaction with an alkali metal alkoxide or aqueous alkali, or reduced, for example by reaction with lithium aluminium hydride. Other suitable methods for the conversion of ether, ester and silyl ether groups into hydroxyl groups are described in Protective Groups in Organic Synthesis, T. W. Greene and P. G. Wuts, Wiley Interscience 1991.

Dinucleotide analogues of formula I where $R^7$ is substituted or unsubstituted alkyl-N,N-dialkylphosphoramidyl can be prepared by reacting compounds of formula I where $R^7$ is hydrogen with a substituted or unsubstituted alkyl-N,N, $N^1$,$N^1$-tetralkylphosphordiamidite such as 2-cyanoethyl-N, N,$N^1$,$N^1$-tetraisopropylphosphordiamidite. The reaction is conveniently carried out under an inert atmosphere in a solvent such as methylene chloride in the presence of an ammonium tetrazolide such as diisopropylammonium tetrazolide. It can be effected at ambient temperature, or moderately elevated temperatures, for example up to $50°$ C.

Dinucleotide analogues of formula I in which $R^1$ is halogen and $R^2$ is hydrogen can be prepared from those of formula I in which $R^1$ is hydroxy and $R^2$ is hydrogen by nucleophilic displacement reactions using conventional procedures.

For example, compounds of formula 1 where $R^1$ is fluoro and $R^2$ is hydrogen may be prepared by reacting a compound of formula I in which $R^1$ is hydroxy and $R^2$ is hydrogen with a dialkylaminofluorosulfurane or sulphur tetrafluoride. The dialkylaminofluorosulfurane is preferably a dialkylaminosulphur trifluoride such as diethylaminosulphur trifluoride (DAST) and is generally reacted in a non-protic solvent, preferably a halohydrocarbon, an aromatic hydrocarbon or tetrahydrofuran, especially a chlorine-containing sovlent such as chloroform or dichloromethane. The reaction is preferably carried out at a temperature from $-78°$ to $30°$ C. Suitable reaction procedures are describes by M. Hudlicky, Organic Reactions 35,513(1988). Suitable reaction procedures for the reaction with sulphur tetrafluroide are describe by C. L. J. Wang, Organic Reactions, 34,319 (1988).

Compounds of formula II where $R^9$ is a substituted or unsubstituted alkyl, cycloalkyl or

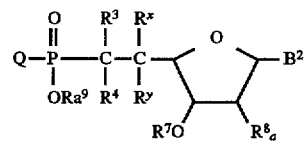

V where $B^2$, $R^x$, $R^y$, $R^3$, $R^4$, $R^8_a$ are as hereinbefore defined, $R^7$ is hydrogen or $R^7_a$, $R^9_a$ is substituted or unsubstituted $C_1$–$C_8$ alkyl, $C_3$–$C_8$ cycloalkyl or $C_7$–$C_{13}$ aralkyl and Q is a protecting group, to replace Q by a hydrogen atom.

The group Q may be any group which is known to be effective in protecting P—H bonds whilst reactions are carried out which would affect such bonds and readily removable after such reactions to generate a P—H bond. Such protecting groups may be, for example, those in compounds of formula Ia of EP 0009348, or those in compounds described in Aust. J. Chem. 33, 292 (1980) or U.S. Pat. No. 4,933,478.

Preferred protecting groups Q include those of formula

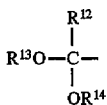
VI where $R^{12}$ is hydrogen, $C_1$–$C_{10}$ alkyl, $C_3$ to $C_8$ cycloalkyl, $C_6$–$C_{10}$ aryl or $C_7$–$C_{11}$ aralkyl and $R^{13}$ and $R^{14}$ are each independently $C_1$ to $C_{10}$ alkyl. Preferred groups of formula VI are those where $R^{12}$ is hydrogen or $C_1$ to $C_4$ alkyl, especially hydrogen or methyl, and $R^{13}$ and $R^{14}$ are each $C_1$ to $C_4$ alkyl, especially methyl or ethyl.

Other preferred protecting groups Q are those of formula

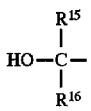
VIA where $R^{15}$ and $R^{16}$ are independently $C_1$–$C_{10}$ alkyl or $R^{15}$ is $C_1$–$C_{10}$ alkyl and $R^{16}$ is $C_6$–$C_{10}$ aryl. Preferred groups of formula VIA are those where $R^{15}$ and $R^{16}$ are $C_1$–$C_4$ alkyl, especially those where $R^{15}$ and $R^{16}$ are each methyl.

Hydrolysis of compounds of formula V to replace Q by a hydrogen atom may be carried out, where Q is a group of formula VI, by reaction with a trialkylsilyl halide such as trimethylsilyl chloride, trimethylsilyl bromide or trimethylsilyl iodide. The reaction may be carried out at a temperature of $-30°$ C. to $100°$ C., preferably 0 to $40°$ C., in the presence of an alcohol such as ethanol, in an organic solvent, for example a halohydrocarbon such as chloroform or trichloroethane, an ether such as tetrahydrofuran or an aromatic hydrocarbon such as benzene, toluene or xylene, or a mixture of two or more of such solvents. In general, when the desired product is a compound of formula II in which $R^9$ is hydrogen, a trialkylsilyl iodide is used, while when a compound of formula II in which $R^9$ is other than hydrogen, i.e. in which $R^9$ is $R^9_a$, is desired, a trialkylsilyl chloride is used. When a trialkylsilyl bromide is used, a mixture of a compound of formula II in which $R^9$ is hydrogen and a compound of formula II in which $R^9$ is $R^9_a$ is generally obtained.

Hydrolysis of compounds of formula V to replace Q by a hydrogen atom can also be effected by treatment with an acid under hydrolytic conditions. It may be carried out with a mineral acid such as hydrochloric acid, in which case $R^9$ in the resulting compound is hydrogen, or with an organic acid such as acetic acid, in which case the resulting product may be a compound where $R^9$ is $R_a^9$, a compound where $R^9$ is hydrogen or a mixture thereof.

When Q is a group of formula VIA, hydrolysis can be effected by treatment with a base, usually under mild conditions, for example by treatment with aqueous ammonia at a temperature from ambient temperature to $100°$ C., preferably from $70°$ to $90°$ C., to give a compound of formula II where $R^9$ is an ammonium ion, which on acidification gives a compound where $R^9$ is hydrogen. Compounds of formula II where $R^9$ is an alkali metal or a substituted ammonium ion can be prepared by carrying out such hydrolysis with an alkali or by reacting a compound of formula II where $R^9$ is hydrogen with an alkali metal base or an amine to form a salt.

Compounds of formula V where $R^7$ is $R^7_a$ may be prepared by reaction of a compound of formula V where $R^7$ is hydrogen, i.e. a compound of formula

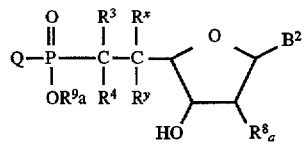
VII where $B^2$, Q, $R^x$, $R^y$, $R^3$, $R^4$,$R^8_a$ and $R^9_a$ are as hereinbefore defined, with a compound of formula $$R^7_a X \qquad \text{VIII}$$

where $R^7_a$ is as hereinbefore defined (other than hydrogen) and X is a halogen atom, for example a chlorine, bromine or iodine atom, or a hydroxyl group, or an anhydride of the acid of Formula $R^{11}$COOH, where $R^{11}$ is as hereinbefore defined. This reaction may be carried out using conventional esterification or etherification procedures. Thus, where $R^7$ is a group —$COR^{11}$, where $R^{11}$ is as hereinbefore defined, esterification may be carried out by reaction of the compound of formula VII with an acid of formula $R^{11}$COOH, or the acid chloride or anhydride thereof, in an inert organic solvent such as an aromatic hydrocarbon, or tetrahydrofuran or a mixture thereof, in the presence of an esterification catalyst. When, as in preferred embodiments of the invention, it is desired to invert the stereochemical orientation of the hydroxy group in the compound of formula V, esterification may be effected using the procedure of Mitsunobu, Synthesis 1981, 1, in the presence of a triarylphosphine and an azodicarboxylate such as diethyl azodicarboxylate or diisopropyl azodicarboxylate.

The compounds of formula VII are alkyl halides, alkenyl halides, aryl halides, aralkyl halides, carboxylic acids, carboxylic acid halides, sulphonic acids, sulphonyl halides or trialkylsilyl halides which are either available commercially or may be prepared by known methods.

Compounds of formula VII where Q is a group of formula VI may be prepared by reaction of an oxetane of formula

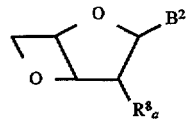
IX where $B^2$ and $R^8_a$ are as hereinbefore defined, with an organometallic compound of formula

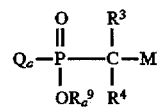
X where $Q_a$ is a group of formula VI, $R^3$, $R^4$ and $R_a^9$ are as hereinbefore defined and M is lithium or magnesium, in the presence of a Lewis acid, preferably a boron trifluoride complex. The reaction is usually carried out at low temperature, preferably $-120°$ C. to $40°$ C., in an inert organic solvent, e.g. tetrahydrofuran, a hydrocarbon such as hexane or a mixture thereof, using 1 to 10 equivalents, preferably 4 to 7 equivalents, of the organometallic compound per equivalent of the oxetane. The organometallic compound of formula X is preferably formed in situ by reaction of an organolithium, preferably an alkyllithium, or an organomagnesium halide, preferably an alkylmagnesium halide, with a compound of formula

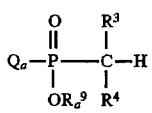  XI where $Q_a$, $R^3$, $R^4$ and $R_a^9$ are as hereinbefore defined. A suitable procedure for reaction of a nucleoside oxetane with an organometallic compound is described in H. Tanaka et al. Tetrahedron Lett., 30,2567 (1989).

Compounds of formula IX may be prepared by reaction of a compound of formula

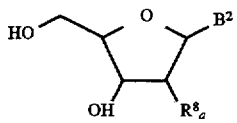  XII where $B^2$ and $R^8_a$ are as hereinbefore defined, with methane sulphonyl chloride in pyridine, followed by treatment with aqueous sodium hydroxide, using the procedure of J. P. Horwitz et al, J. Org. Chem., 31,205 (1966).

Compounds of formula XI can be obtained by reaction of a protected phosphinate ester of formula

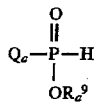  XIII where $Q_a$ and $R_a^9$ are as hereinbefore defined, with a compound of formula

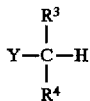  XIV where $R^3$ and $R^4$ are as hereinbefore defined and Y denotes a leaving atom or group.

Phosphinate esters of formula XIII may be prepared by known methods, for example as described in EP 0009348, Aust. J. Chem. 33, 212 (1980) or U.S. Pat. No. 4,933,478.

The leaving atom or group Y in formula XIV may be, for example, a halogen atom or a residue of an organic acid after removal of an acidic hydrogen atom therefrom, such as an organic sulphonate group, e.g. a p-toluenesulphonate or trifluoromethanesulphonate group. Preferably Y is a halogen atom or an arylsulphonate group, especially a chlorine or bromine atom or a p-toluenesulphonate group. Thus compounds of formula XIV are known or may be prepared by known methods.

The reaction between the protected phosphinate ester of formula XIII and the compound of formula XIV may be carried out under conventional conditions for substitution reactions at a P—H bond, for example using a base such as sodium, sodium hydride or an alkyllithium in an inert organic solvent such as tetrahydrofuran.

Compounds of formula XII where $R^8_a$ is hydrogen or hydroxy are readily available nucleosides. Compounds of formula XII where $R^8_a$ is other than hydrogen or hydroxy can be prepared by conventional halogenation, etherification, esterification or silylation reactions of compounds where $R^8_a$ is hydroxy.

Compounds of Formula XI may alternatively be prepared by reacting a protected phosphinate ester of Formula XIII with a silylating agent to give a P(III) silyl compound and reacting the latter with a compound of Formula XIV. Suitable silylating agents include those hereinbefore described.

This method is convenient for the preparation of compounds of formula XI where $R^3$ and/or $R^4$ are fluorine, when the ester of formula XIII can be reacted with bis(trimethylsilyl) amide in a solvent such as toluene at −80° C. to 40° C. to give a P(III) silyl compound, which is then reacted with a compound of formula XIV where $R^3$ and/or $R^4$ are fluorine and Y is a chlorine atom, e.g. chlorodifluoroethane, conveniently in the same solvent at −80° C. to 40° C.

Compounds of formula V where Q is a group of formula VI or VIA and $R^3$ and $R^4$ are each hydrogen can be prepared by glycosylation of a compound of formula

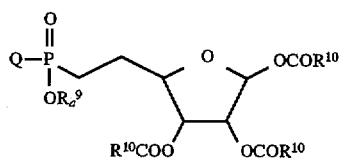  XV where Q, $R_a^9$ and $R^{10}$, are as hereinbefore defined, with a base of formula $B^2H$  XVI where $B^2$ is as hereinbefore defined, in the presence of a silylating agent such as trimethylsilyl choloride, bis (trimethylsilyl)acetamide or hexamethyldisilazane and a catalyst such as a fluoroalkanesulphonate salt in an inert organic solvent such as acetonitrile or 1,2-dichloroethane at a temperature of 40°–90° C., followed by reaction with an aqueous acid, usually an organic acid such as acetic acid, to regenerate the tertiary hydroxyl group which has become silylated during the glycosylation reaction, to give a compound of formula

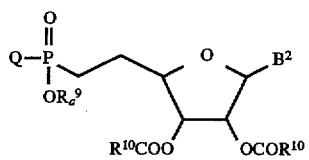  XVII where Q and $R^9_a$ are as hereinbefore defined. The reaction with aqueous acid may be carried out at 90° to 100 ° C.

If it is desired to produce a compound of formula V in which $R^7$ is hydrogen and $R^8_a$ is hydroxy, the compound of formula XVII can be subjected to mild basic hydrolysis conditions, for example by treatment with potassium carbonate in methanol at ambient temperature, to hydrolyse the $R^{10}$COO— groups in formula XVII.

The bases of formula XVI are readily available nucleoside bases such as adenine, cytosine, guanine, thymine or uracil or substituted derivatives thereof prepared by known procedures.

Compounds of formula XV can be prepared by reaction of an olefinic acetonide of formula

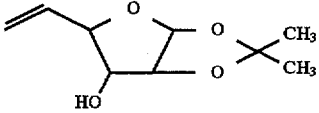  XVIII with a phosphinate of formula $$Q-\overset{O}{\underset{OR_a^9}{\overset{\|}{P}}}-H \qquad XIX$$

where Q and $R_a^9$ are as hereinbefore defined, in the presence of a free radical initiator, to give a compound of formula

XX

[structure showing phosphinate linked to acetonide-protected furanose]

then hydrolysing the acetonide group in the compound of formula XX, for example by treatment with an acidic ion exchange resin, to give a compound of formula

XXI

[structure showing phosphinate with diol furanose]

which is then esterified by reaction with an acid of formula $R^{10}$ COOH, or an anhydride or acid halide thereof, to give a compound of formula XV.

The reaction of the olefinic acetonide with the phosphinate may be carried out in an organic solvent, usually an aromatic hydrocarbon such as benzene, toluene or xylene, in the presence of a free radical initiator. The initiator may be a peroxide such as benzoyl peroxide, tert-butyl peroxide or 2,2-bis(tert-butylperoxy)-propane, a perester such as tert-butyl perbenzoate or tert-butyl per-2-ethylhexanoate, a percarbonate such as diacetylperdicarbonate or bis(4-tert-butylcyclohexyl)perdicarbonate, or a persalt such as potassium persulphate. The reaction may be carried out at 30° to 100° C., preferably 70° to 90° C.

The olefinic acetonide of formula XVIII may be prepared from a diacetonide of formula

XXII

[structure of diacetonide]

which itself can be prepared as described in Carbohyd. Res. 24 (1972) 194–5. The diacetonide may be reacted with a carboxylic acid anhydride or acid halide, usually acetic anhydride, to esterify the hydroxyl group and the product reacted with 80% acetic acid at ambient temperature to give a monoacetonide of formula

XXIII

[structure of monoacetonide with HO, HO, and $R^{11}COO$ groups]

which is then reacted with methanesulphonyl chloride in the presence of a base to replace both the indicated hydroxyl groups by methanesulphonyloxy groups. The product is reacted with sodium iodide in methyl ethyl ketone at 70°–90° C. to give an olefinic acetonide of formula

XXIV

[structure of olefinic acetonide with $R^{11}COO$ group]

which is hydrolysed by treatment with potassium carbonate in aqueous methanol at ambient temperature to give an olefinic acetonide of formula XVIII.

The phosphinate of formula XIX where Q is a group of formula VI is a phosphinate of formula XIII and may be prepared as hereinbefore described.

The phosphinate of formula XIX where Q is a group of formula VIA may be prepared by esterifying a phosphonous acid of formula $$HO-\underset{\underset{R^{16}}{|}}{\overset{\overset{R^{15}}{|}}{C}}-\underset{\underset{OH}{|}}{\overset{\overset{O}{\|}}{P}}-H \qquad XXV$$

with an alcohol of formula $R_a^9$ OH where $R_a^9$, $R_{15}$ and $R^{16}$ are as hereinbefore defined.

The esterification may be carried out at –10° to 30° C., preferably 0° to 10° C. It is conveniently carried out in a solvent, preferably an ether such as tetrahydrofuran, preferably in the presence of a base, usually a tertiary amine such as dimethylaminopyridine, and a dehydrating agent such as N,N$^1$-dicyclohexylcarbodiimide.

Phosphonous acids of formula XXV can be prepared by reacting hypophosphorous acid with a ketone of formula $$\underset{R^{16}}{\overset{R^{15}}{\diagdown}}C=O \qquad XXVI$$

or by reacting hypophosphorous acid with a ketal of this ketone using the procedure described by S. J. Fitch, J. Amer. Chem. Soc. 86,61(1964), followed by hydrolysis of the resulting phosphonous ester, for example by heating with water.

Compounds of formula V can also be prepared by reacting an olefinic nucleoside of formula

XXVII

[structure of olefinic nucleoside with $B^2$, $R_a^7O$, and $OCOR^{10}$ groups]

where $B^2$ and $R^{10}$ are as hereinbefore defined and $R_a^7$ is as hereinbefore defined, with a phosphinate of formula XIX in the presence of a free radical initiator, for example under the same conditions as used for reaction of the phosphinate with the olefinic acetonide of formula XVIII as hereinbefore described.

Olefinic nucleosides of formula XXVII may be prepared by glycosylation of a compound of formula

XXVIII

[structure with $OCOR^{10}$, $R_a^7O$, and $OCOR^{10}$ groups]

where $R^{10}$ and $R_a^7$ are as hereinbefore defined, with a base of formula XVI, for example using the conditions hereinbefore described for the glycosylation of compounds of formula XV.

Compounds of formula XXVIII can be prepared by reaction of the olefinic acetonide of formula XVIII with either a compound of formula

                  XXIX where $R^7_a$ is as hereinbefore defined and X is halogen or hydroxy, or an anhydride of formula

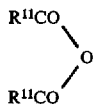                  XXX where $R^{11}$ is as hereinbefore defined, to give a compound of formula

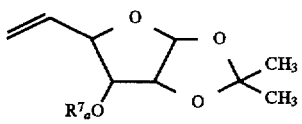                  XXXI where $R^7_a$ is as hereinbefore defined, reacting the compound of formula XXXI with an acidic ion exchange resin at 60° to 80° C. to hydrolyse the acetonide group to form a compound of formula

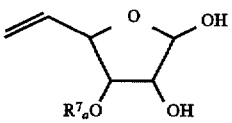                  XXXII where $R^7_a$ is as hereinbefore defined, and esterifying the hydroxyl groups in this compound by reaction with an acid of formula $R^{10}$ COOH or an anhydride or acid halide thereof, where $R^{10}$ is as hereinbefore defined, to give a compound of formula XXVIII.

The compounds $R^7_a X$ are alkyl halides, alkenyl halides, aryl halides, aralkyl halides, carboxylic acids, carboxylic acid halides or trialkylsilyl halides which are either available commercially or may be prepared by known methods. Reaction of such a compound with the olefinic acetonide of formula XVIII may be carried out using conventional etherification or esterification procedures.

Compounds of formula III where $R^5_a$ is a group of formula —$OCOR^{10}$, some of which are novel compounds, where $B^1$ is a thyminyl residue, possessing antiviral properties, including those where $B^1$ is a thyminyl group and $R^6$ is benzoyl, can be prepared by glycosylation of a compound of formula

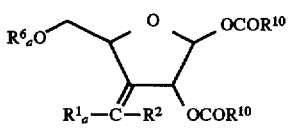                  XXXIII where $R^1_a, R^2, R^6_a$ and $R^{10}$ are as hereinbefore defined, with a base of formula

                  XXXIV where $B^1$ is as hereinbefore defined. This reaction may be carried out under known glycosylation conditions, for example in the presence of a silylating agent such as trimethylsilyl chloride, bis(trimethylsilyl)acetamide or hexamethyldisilazane and an appropriate catalyst such as a fluoroalkanesulphonate salt in an inert organic solvent such as acetonitrile or 1,2-dichloroethane at a temperature of 40°–90° C.

The bases of formula XXXIV are readily available nucleoside bases such as adenine, cytosine, guanine, thymine or uracil or substituted derivatives thereof prepared by known procedures.

Compounds of formula XXXIII may be prepared by treatment of a compound of formula

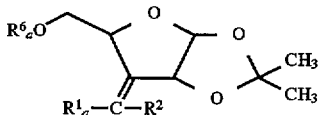                  XXXV where $R^{1a}$, $R^2$ and $R^6$ are as hereinbefore defined, with an acidic ion exchange resin to hydrolyse the acetonide group, usually in water or a polar organic solvent such as dimethyl formamide or dichloromethane at 40°–100° C., followed by esterification of the hydroxy groups formed on hydrolysis by reaction with an acid of formula $R^{10}$ COOH, or an anhydride or acid halide thereof, where $R^{10}$ is as hereinbefore defined.

Compounds of formula XXXV where $R^1_a$ and $R^2$ are each hydrogen can be obtained by a Wittig reaction of a ketone of formula

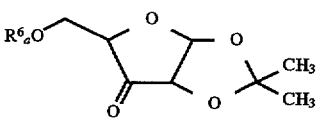                  XXXVI with a quaternary phosphonium salt and an alkyllithium, usually at a temperature increasing from within the range −60° to −80° C. to ambient temperature, the reaction mixture obtained being acidified, usually with acetic acid. The reaction may be carried out in an organic solvent, e.g. tetrahydrofuran, a hydrocarbon such as hexane or a mixture thereof.

Compounds of formula XXXV where one or both of $R^1_a$ and $R^2$ are halogen can be obtained from compounds of formula XXXVI.

Reaction of such compounds with carbon tetrachloride and triphenylphosphine in acetonitrile using the procedure described by J. M. J. Trondiet et al, Eur. J. Med. Chem-Chim. Ther. 11(6), 489 (1976) gives compounds of formula XXXV where $R^1_a$ and $R^2$ are chlorine. Reaction of compounds of formula XXXVI with dibromodifluoromethane, hexamethylphosphorustriamide and zinc in tetrahydrofuran gives novel compounds of formula XXXV where $R^1_a$ and $R^2$ are each fluorine.

Compounds of formula XXXVI may be prepared from 1,2-isopropylidenexylose by reaction of the primary alcohol group with a compound of formula $R^6_a X$ where $R^6_a$ is as hereinbefore defined and X is a halogen atom or a hydroxyl group, to convert the methylol group into a group —$CH_2OR^6_a$, and reacting the product with an oxidising agent such as pyridinium dichromate, usually at 30°–40° C. in the presence of a dehydrating agent such as acetic anhydride and in an inert solvent such as methylene chloride, to convert the $3^1$-hydroxyl group into a keto group. A suitable procedure for preparation of compounds of formula XXXVI is described by H. S. Mosher et al, J. Org. Chem 51, 2702 (1986).

The compounds $R^6_a X$ may be chosen from a similar range of compounds as the compound $R^7_a$ X of formula VIII as hereinbefore described, and reaction with the xylose acetonide may be carried out using known esterification or etherfication procedures.

Compounds of formula III where $R^5_a$ is hydroxy and/or $R^6$ is hydrogen can be obtained by hydrolysis of a compound of formula III in which $R^5_a$ is a group —$OCOR^{10}$ and/or $R^6$ is other than hydrogen, e.g. alkyl, —COR$^{11}$ where R$^{11}$ is alkyl or aryl, or trialkylsilyl, using known procedures.

Compounds of formula III where R$^5_a$ is fluorine or chlorine may be prepared by nucleophilic displacement reactions of compounds of formula III where R$^5_a$ is hydroxy using known procedures.

Compounds of formula III where R$^5_a$ is alkoxy, alkenoxy, aryloxy, aralkyloxy or substituted silyloxy can be prepared by etherification of compounds of formula III where R$^5_a$ is hydroxy using known procedures.

Compounds of formula IV may be prepared by reaction of the corresponding 3$^1$-iodo nucleoside with carbon monoxide and tris(trimethylsilyl)silane in the presence of a free radical initiator such as 2,2$^1$-azobis(isobutyronitrile), by reduction of the corresponding 3$^1$-cyano nucleoside with diisobutyla-luminium hydride or otherwise as described in WO 92/20823.

Compounds of formula IV may also be prepared by treatment of the corresponding 3$^1$-amino nucleoside with nitrite as described by S. Shuto et al, Nucleosides & Nucleotides, 1 (3), 263–272(1982), or by hydrolysis of the corresponding 3$^1$-C-(4,5-dihydro-5-methyl-1,3,5-dithiazin-2-yl) nucleoside as described by Bamford et al, J. Med. Chem. 1990, 33, 2494.

Intermediates for the dinucleotides analogues of the invention which are themselves novel include compounds of formula II and V in which R$^x$ and R$^y$ are not both hydrogen, i.e. compounds of formula

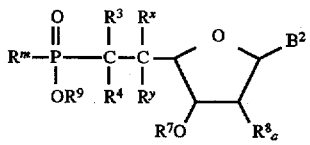

where R$^3$, R$^4$, R$^7$, R$^8_a$, R$^9$, R$^x$, R$^y$, and B$^2$ are as hereinbefore defined and R$^m$ is hydrogen or Q as hereinbefore defined, provided that R$^x$ and R$^y$ are not both hydrogen. Compounds of formula V where R$^x$ is hydrogen and R$^y$ is R$^{17}$ which is C$_1$–C$_{10}$ alkyl, C$_2$–C$_{10}$ alkenyl, C$_3$–C$_8$ cycloalkyl, C$_6$–C$_{15}$ aryl, or C$_7$–C$_{16}$ aralkyl, may be prepared by deoxygenation of a compound of formula

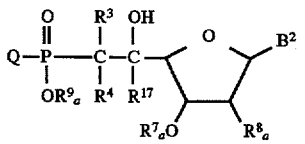 XXXVII where B$^2$, Q, R$^3$, R$^4$, R$^7_a$, R$^8_a$, R$^9_a$, and R$^{17}$ are as hereinbefore defined. The deoxygenation may be carried out using deoxygenation procedures hereinbefore described.

Compounds of formula XXXVII can be obtained by reaction of a compound of formula X as hereinbefore defined with a compound of formula

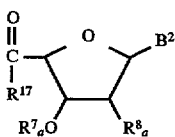 XXXVIII where B$^2$, R$^7_a$, R$^8_a$ and R$^{17}$ are as hereinbefore defined, optionally in the presence of a Lewis acid such as a boron trifluoride complex, for example under the conditions used for reaction of the compounds of formulae IX and X.

Compounds of Formula XXXVII can also be obtained by reaction of a compound of Formula XIII, in ionic form produced by treatment with a base such as sodium or sodium hydride, in the presence of a Lewis acid such as a boron trifluoride complex, with an epoxide of the diol of formula XXIII, which epoxide can be prepared following the procedure of V. Zsoldos-Mády et al, Monatshifte für Chemie, 117, 1325 (1986).

Compounds of formula XXXVIII may be prepared by reaction of an aldehyde of formula

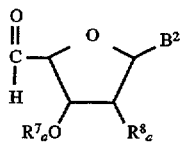 XXXIX where B$^2$, R$^7_a$ and R$^8_a$ are as hereinbefore defined, with an organometallic compound of formula R$^{17}$Li or R$_{17}$Mg Y where R$^{17}$ is as hereinbefore defined and Y is halogen, usually chlorine or bromine, generally in an organic solvent, preferably an ether such as tetrahydrofuran or diethyl ether, and at a temperature of −120° to 0° C., preferably −100° to −60° C., followed by oxidation, for example a Swern oxidation, of the resulting alcohol.

Aldehydes of formula XXXIX can be obtained by oxidation of the corresponding 5'-hydroxymethyl compounds using known methods, for example by treatment with a haloacetic acid, dimethyl sulphoxide and dicyclohexylcarbodiimide using the procedure of Jones and Moffat, J. Amer. Chem. Soc. 90,5337 (1968) or Ranganatham et al, J. Org. Chem. 39, 290 (1974). The 5'-hydroxymethyl compounds are readily available nucleosides or substituted derivatives thereof.

Compounds of formula V where R$^x$ is —OR$^{17}$ and R$^y$ is R$^{17}$, where R$^{17}$ is as hereinbefore defined, may be prepared by etherification of the hydroxyl group in compounds of formula XXXVII by reaction with a halide of formula R$^{17}$Y where R$^{17}$ is as hereinbefore defined and Y is halogen, usually bromine or iodine. The reaction is generally carried out in the presence of a base e.g. sodium hydride or a hindered amine such as 1,8-diazabicyclo[5.4.0]undec-7-ene in an organic solvent, usually a hydrocarbon such as benzene or toluene.

A similar etherification procedure may be used to convert compounds of formula

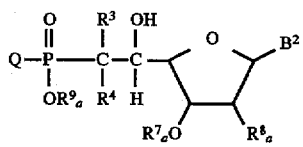 XXXX where B$^2$, Q, R$^3$, R$^4$, R$^7_a$, R$^8_a$ and R$^9_a$ are as hereinbefore defined, into compounds of formula V where R$^x$ is —OR$^{17}$ and R$^y$ is hydrogen.

Compounds of formula V where R$^x$ is halogen and R$^y$ is hydrogen or R$^{17}$ can be obtained by a nucleophilic displacement reaction of a compound of formula XXXX or XXXVII respectively, for example with diethylamino sulphur trifluoride in an organic solvent such as methylene chloride at a temperature of −100° to −30° C., optionally in the presence of pyridine.

Compounds of formula V where R$^x$ is —OCOR$^{17}$ and R$^y$ is hydrogen or R$^{17}$ may be prepared by reacting a compound of formula XXXX or XXXVII respectively with an acid of formula R$^{17}$COOH or an acid halide or anhydride thereof, where R$^{17}$ is as hereinbefore defined, to esterify the hydroxyl group. The reaction may be carried out using conventional esterification procedures; for example, where an acid chloride or anhydride is used, the esterification may be effected in the presence of an organic base such as pyridine in an organic solvent such as methylene chloride, toluene or ethyl acetate at a temperature from −70° to 30° C., preferably −15° to −5° C.

Compounds of formula XXXX can be prepared by reacting an aldehyde of formula XXXIX with a compound of formula X. The reaction is generally carried out at a temperature of −100° to 0° C., preferably −70° to −8° C., in an organic solvent such as tetrahydrofuran, diethyl ether, tert-butyl methyl ether or toluene, optionally in the presence of a Lewis acid such as a boron trifluoride complex.

Dinucleotide analogues of formula I in which $R^9$ is hydrogen can be obtained from dinucleotide analogues of Formula I in which $R^9$ is $R^9_a$ as hereinbefore defined by hydrolysis, preferably by treatment with a base. Such hydrolysis is preferably carried out using an alkali metal hydroxide, particularly sodium hydroxide or lithium hydroxide, or concentrated aqueous or ethanolic ammonia.

When mixtures of diastereomers of dinucleotides of formula I or intermediates are obtained, these can be separated by known methods, for example by fractional distillation, crystallisation or chromatography.

The present invention also provides oligonucleotides containing at least one unit derived from a dinucleotide analogue of formula I, and the use of dinucleotide analogues of formula I in the synthesis of such oligonucleotides. Such oligonucleotides may contain only units derived from the same or different dinucleotide analogues of formula I, preferably of formula IA, or may contain at least one unit derived from a dinucleotide of formula I and at least one other unit derived from another natural or synthetic nucleoside. Generally, the oligonucleotides contain 2 to 200 nucleoside-derived units. Preferred oligonucleotides contain 2 to 100, more preferably 2 to 50, especially 2 to 20 such units. Preferably, the oligonucleotides contain units of the same or different dinucleotide analogues of formula I together with units of natural or synthetic nucleoside derived from D-ribose or 2-deoxyribose.

The present invention further provides oligonucleotides of formula

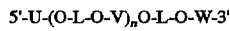   XXXXI where U, V and W are the same or different residues of natural or synthetic nucleosides and at least one of the residues U, V and W being derived from a dinucleotide analogue of formula I and having the formula

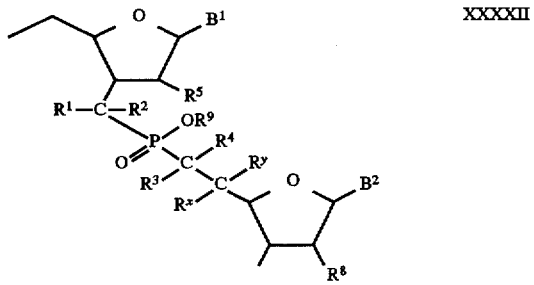   XXXXII

L is a nucleoside-bridging group and n is a number from 0 to 200, preferably 0 to 100, more preferably 0 to 50, especially 0 to 30. A preferred bridging group L is the natural oligonucleoside-bridging group —P(O)O$^\ominus$. Examples of further bridging groups are —P(O)S$^\ominus$—, —P(S)S$^\ominus$—, —P(O)R$^{18}$—, —P(O)NR$^{19}$R$^{20}$— or —CH$_2$— where R$^{18}$ is hydrogen or C$_1$-C$_6$ alkyl and R$^{19}$ and R$^{20}$ are independently hydrogen or C$_1$-C$_6$ alkyl.

The residues derived from one or more dinucleotides of formula I can be bonded terminally or in the nucleotide sequence whereby several, for example 2 to 5, residues derived from one or more dinucleotide analogues of formula I can be bonded between residues of natural or synthetic nucleosides, or there can be mixed forms of this distribution lying in the nucleotide sequence. Preferably there are 4 to 30 nucleoside units, of which preferably 1 to 12, especially 1 to 6 and particularly 1 to 4, units are residues derived from dinucleotide analogues of formula I.

Particularly preferred embodiments are oligonucleotides of formula XXXXI where n is 2 to 50, preferably 2 to 30, L is a group —P(O)O$^\ominus$, U, V and W are the same or different residues of a natural nucleoside, and at least one of the residues U, V and W is of formula XXXXII. The natural nucleoside may be, for example, adenosine, cytosine, guanosine, uridine, 2-aminoadenosine, 5-methylcytosine, 2'-deoxyadenosine, 2'-deoxycytosine, 2'-deoxyguanosine or thymidine. The residue of formula XXXXI can be bound terminally or in the nucleotide sequence, whereby several, for example 2 to 5 of the same or different residues of formula XXXXI can follow one after another, or the same or different residues of formula XXXXI can be bound between residues of natural nucleosides, or mixed types of these distributions can lie in the nucleotide sequence.

In another especially preferred embodiment of oligonucleotides of formula XXXXI, U, V and W are the same or different residues of formula XXXXII in which B$^1$ and B$^2$ are natural nucleoside base radicals. In this embodiment, n is preferably 2 to 20, especially 1 to 12, more especially 1 to 6 and most especially 1 to 4.

The preparation of oligonucleotides according to the invention can be carried out using known procedures, if necessary automatically using commercial nucleic acid synthesizing machines. In the case of the bridging group —P(O)O$^\ominus$, for example, the phosphotriester process, the phosphite triester process or the H-phosphonate process can be used, all of which are familiar to those skilled in the art. Many suitable procedures are described in Oligonucleotides and Analogues: A Practical Approach, edited by F. Eckstein, Oxford University Press, 1991.

In a typical procedure, a dinucleotide analogue of formula I where R$^6$ and R$^7$ are each hydrogen, i.e. where the 5$^1$ and 3$^1$ hydroxyls are free, is reacted with 4,4$^1$-dimethoxytriphenylmethyl chloride in the presence of a base, for example using the procedure described in WO92/20822 or WO 92/20823, to give a dinucleotide analogue of formula I where R$^6$ is a dimethoxytrityl group, which is then reacted with 2-cyanoethyl-N,N,N$^1$,N$^1$-tetraisopropyl phosphordiamidite to replace the 3$^1$ hydroxyl by a 2-cyanoethyl-N, N-diisopropylphosphoramidyl group, thereby activating the dinucleotide analogue for coupling at the 3$^1$ position. The functionalised dinucleotide analogues obtained can be inserted into any desired sequence using, for example, a CPG-solid support and standard nucleic acid synthesizing machine such as Biosystems 380B, 390 and 394 and Milligen/Biosearch 7500 and 8800s.

When an oligonucleotide of the invention contains one or more units of formula XXXXII in which R$^9$ is R$^9_a$ as herebefore defined, it may be converted into the corresponding oligonucleotide where R$^9$ is hydrogen by hydrolysis, preferably by base hydrolysis as hereinbefore described for hydrolysis of dinucleotide analogues of formula I in which R$^9$ is R$^9_a$.

The dinucleotide analogues of the invention and oligonucleotides incorporating units derived therefrom can be used in therapeutics, for example in the treatment of a human or other animal suffering from a disease which is modulated by a protein, or in the treatment of viruses such as influenza, herpes and HIV. Accordingly, the present invention also provides a pharmaceutical composition comprising as active ingredient a dinucleotide analogue of the invention or an oligonucleotide incorporating at least one unit derived therefrom. Optimum dosages and treatment schedules can readily be determined by those skilled in the art. When administered to mammals of about 70 kg weight, the dose can be, for example, 0.01 to 1000 mg per day. It will generally be preferred to administer therapeutic agents in accordance with the invention internally, for example orally, by inhalation, intravenously or intramuscularly. Other methods of administration, such as transdermal, topical or intralesional methods, and by inclusion in suppositries, can also be useful. Use in conjuction with pharmacologically acceptable carriers is preferred for some therapeutic treatments.

The oligonucleotides according to the invention have a surprisingly high stability to degradation by nucleases. A very good plating with complementary nucleic acid strands, particularly of the RNA type, is also observed. The oligonucleotides according to the invention are therefore particularly suitable for antisense technology, i.e. for inhibition of the expression of undesired protein products due to the binding to suitable complementary nucleotide sequences in nucleic acids (see EP 0 266 099, WO 87/07300 and WO 89/08146). They can be employed for the treatment of infections and diseases, for example by blocking the expression of bioactive proteins at the nucleic acid stage (for example oncogenes). The oligonucleotides according to the invention are also suitable as diagnostics and can be used as gene probes for the detection of viral infections or of genetically related diseases by selective interaction at the single or double-stranded nucleic acid stage. In particular—due to the increased stability to nucleases—diagnostic use is not only possible in vitro but also in vivo (for example tissue samples, blood plasma and blood serum). Use possibilities of this type are described, for example, in WO 91/06556.

The pharmacologically active dinucleotides and oligonucleotides according to the invention can be used in the form of parentally administrable preparations-or of infusion solutions. Solutions of this type are preferably isotonic aqueous solutions or suspensions, it being possible to prepare these before use, for example in the case of lyophilized preparations which contain the active substance on its own or together with a carrier, for example mannitol. The pharmaceutical preparations can be sterilised and/or contain excipients, for example preservatives, stabilisers, wetting and/or emulsifying agents, solubilisers, salts for regulating the osmotic pressure and/or buffers. The pharmaceutical preparations, which if desired can contain further pharmacologically active substances such as, for example, antibiotics, are prepared in a manner known per se, for example by means of conventional dissolving or lyophilising processes, and contain about 0.1% to 90%, in particular from about 0.5% to about 30%, for example 1% to 5% of active substance(s).

The invention is illustrated by the following Examples.

EXAMPLE 1

This example describes the preparation of the compound of formula

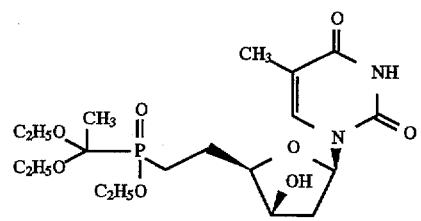

Compound 1

To a solution of ethyl methyl(1,1-diethoxyethyl)phosphinate (59.5 g, 0.26 mole) in tetrahydrofuran (THF) (500 ml) at −78° C. under an atmosphere of argon is added nBuLi (170 ml, 1.6 molar solution in hexanes) slowly over 20 minutes. The resulting solution is stirred at −78° C. for 90 minutes. Boron trifluoride etherate (39 g, 0.27 mole) is then added over 5 minutes followed after a further 5 minutes by the dropwise addition of a solution of 1-(3,5-anhydro-β-D-threo-pentofuranosyl)thymine (12 g, 53mmole) in THF (500 ml) over one hour. The resulting solution is stirred for one hour at −78° C. before the addition of $NaHCO_3$ (saturated) solution (30 ml) plus $NaHCO_3$ (10 g). The resulting mixture is allowed to warm to room temperature over a few hours and then concentrated in vacuo. Addition of dichloromethane (400 ml) and filtration gives a clear yellow oil after concentration. Purification by vacuum flash silica chromatography gradient elution (chloroform-chloroform/ethanol 15:1) gives Compound 1 as a hygroscopic white solid, mp 24°–51° C.

Found C 49.7%, H 7.4%, N 6.0%, P 6.7%; required for $C_{19}H_{33}N_2O_8P\cdot\frac{1}{2}H_2O$, C 49.9%, H 7.5%, N 6.1%, P 6.75%.

NMR characterisation as a mixture of 2 diastereoisomers: $^{31}P$ nmr $^1H$ decoupled ($CDCl_3$, 36.4 MHz) δ 50.7, 50.5 ppm.

EXAMPLE 2

This Example describes the preparation of the compound of formula

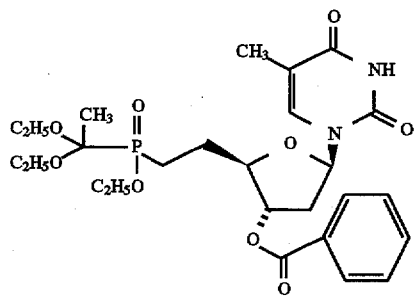

Compound 2

Diethylazodicarboxylate (2.8 ml, 18 mmole) is added dropwise to a cooled (0°–5° C.) solution of Compound 1 (7.3 g, 16.3 mmole), triphenylphosphine (4.7 g, 18 mmole) and benzoic acid (2.19 g, 18 mmole) in a mixture of toluene (100 ml) and tetrahydrofuran (30 ml) under argon. After standing at room temperature for 60 hours, the mixture is concentrated and purified by vacuum flash chromatography (gradient elution dichloromethane/ethanol 100:0→10:1) to give a white solid which is dissolved in dichloromethane (200 ml) and washed with saturated sodium hydrogen carbonate solution (5×100 ml), dried over magnesium sulphate and concentrated to give a white foam of Compound 2.

Found: C 55.9, H 7.0, N 4.8, P 5.8%; $C_{26}H_{37}N_2O_9P\cdot\frac{1}{2}H_2O$ requires C 55.6, H 6.8, N 5.0, P 5.5%

NMR characterisation as a mixture of 2 diastereomers at phosphorus:

$^{31}P$ nmr $^1H$ decoupled ($CDCl_3$, 161.9 MHz) δ 5 49.1, 49.2 ppm.

EXAMPLE 3

This Example describes the preparation of the compound of formula:

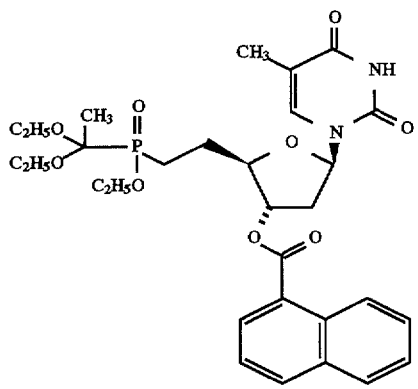

Compound 3

Diethylazodicarboxylate (2.1 ml 13 mmole) is added dropwise (5 minutes) to a cooled (0°–5° C.) and stirred solution of Compound 1 (5 g, 11 mmole), triphenylphosphine (3.5 g, 13 mmole) and 1-naphthoic acid (2.3 g, 13 mmole) in a mixture of toluene (60 ml) and tetrahydrofuran (15 ml) under argon. The resulting solution is allowed to stand at room temperature for 48 hours and then concentrated in vacuo. Purification by flash silica column chromatography (eluant:chloroform/ethanol 50:1) gives Compound 3 as a white solid.

Found C 59.5%, H 6.8%, N 4.6%, P 5.3%; $C_{30}H_{39}N_2O_9$ P requires C 59.8%, H 6.5%, N 4.65%, P 5.15%.

NMR characterisation as a 1:1 mixture of diastereoisomers at phosphorus:

$^{31}P$ nmr $^1H$ decoupled (CDCl$_3$, 36.4 MH$_2$) δ 48.3, 48.2 ppm.

EXAMPLE 4

This example describes the preparation of the compound of formula

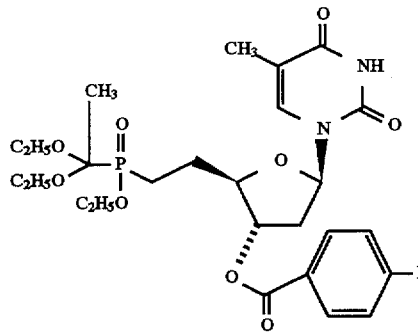

Compound 4

Diethylazodicarboxylate (0.42 ml, 2.7 mmole) is added dropwise (5 minutes) to a stirred solution of Compound 1 (1.0 g, 2.2 mmole), triphenylphosphine (0.70 g, 2.7mmol) and p-nitrobenzoic acid (0.45 g, 2.7 mmole), in a mixture of toluene (20 ml) and tetrahydrofuran (5 ml) under argon. After standing at room temperature overnight the mixture is concentrated and purified by flash silica column chromatography, (eluant:chloroform/ethanol 50:1) to give Compound 4, mp 60°–63° C.

Found C 52.3%, H 6.1%, N 6.8%, P 5.2%; required for $C_{26}H_{36}N_3O_{11}P$, C 52.25%, H 6.05%, N 7.05%, P 5.2%.

NMR characterisation as a 1:1 mixture of diastereoisomers at phosphorus:

$^{31}P$ nmr $^1H$ decoupled (CDCl$_3$, 36.4 MHz) δ 47.9, 47.2 ppm.

EXAMPLE 5

This example describes the preparation of the compound of formula

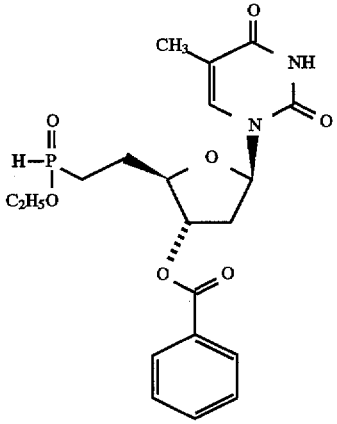

Compound 5

Trimethylsilylchloride (4.56 ml, 36 mmole) is added dropwise (2 minutes) at 0° C. to a stirred solution of Compound 2 (2 g, 3.6 mmole) and ethanol (1 ml) in chloroform (20 ml) under argon. The resulting solution is allowed to stand at room temperature overnight and then concentrated in vacuo to give an off-white foam which is purified by flash silica chromatography (eluant 40:1 chloroform/ethanol) to give Compound 5 as a white solid.

Found: C 52.7%, H 5.7%, N 6.1%, P 6.8%; $C_{20}H_{25}N_2O_7P.H_2O$ requires C 52.85%, H 6.0%, N 6.15%, P 6.8%.

NMR characterisation as a 1:1 mixture of diastereoisomers at Phosphorus:

$^{31}P$ nmr $^1H$ decoupled (162 MHz, CDCl$_3$) δ 37.4, 37.1 ppm.

EXAMPLE 6

This example describes the preparation of the compound of formula:

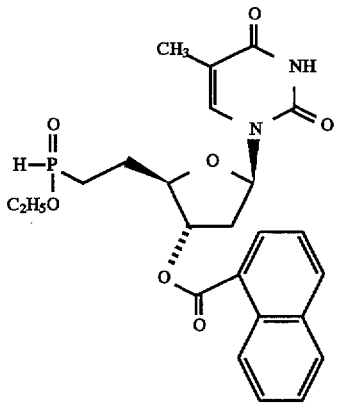

Compound 6

Trimethylsilylchloride (0.42 ml, 3.3 mmole) is added to a stiffed solution of Compound 3 (199 mg, 0.33 mmole) in chloroform (5 ml) containing ethanol (10 pipette drops) under argon. The resulting solution is allowed to stand at room temperature overnight and then concentrated in vacuo to give an off-white foam which is purified by flash silica column chromatography (eluant 40:1 chloroform/ethanol) to give Compound 6 as a white solid.

Found C 59.0%, H 5.5%, N 5.5%, P 6.1%; $C_{24}H_{27}N_2O_7P$ requires C 59.25%, H 5.6%, N 5.75%, P 6.35%.

NMR characterisation as a 1:1 mixture of diastereoisomers at phosphorus:

$^{31}P$ nmr $^1H$ decoupled (CDCl$_3$, 162 MHz) δ 37.6, 37.2 ppm.

EXAMPLE 7

The example describes the preparation of the compound of formula

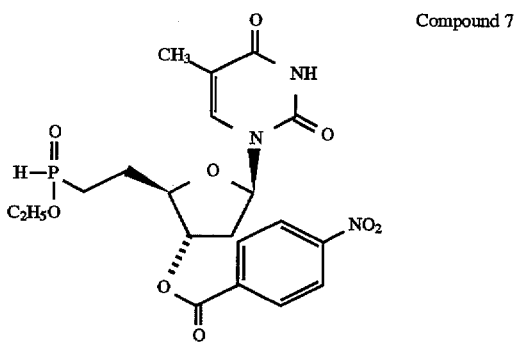

Compound 7

Trimethylsilylchloride (14 ml, 0.11 mmole) is added dropwise (2 minutes) to a stirred solution of Compound 4 (7 g, 11.7 mmole) and ethanol (1 ml) in chloroform (150 ml) under argon. The resulting solution is allowed to stand at room temperature overnight and then concentrated in vacuo to give a pale yellow foam which is purified by flash silica column chromatography (gradient elution: chloroform/ ethanol 40:1→20:1) to give Compound 7 as a white solid.

Found C 49.4%, H 5.1%, N 8.4%, P 6.3%; $C_{20}H_{24}N_3O_9P\cdot\frac{1}{2}H_2O$ requires C 49.3%, H 5.1%, N 8.6%, P 6.35%.

NMR characterisation as a 1:1 mixture of diastereoisomers at phosphorus:

$^{31}P$ nmr $^1H$ decoupled (36.4 MHz), CDCl$_3$) δ 36.3, 35.9 ppm.

EXAMPLE 8

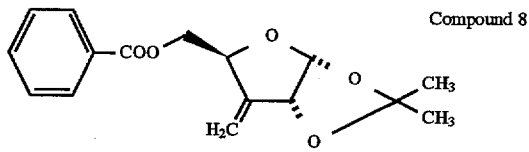

Compound 8

To a suspension of methyltriphenylphosphonium bromide (82.5 g, 0.231 mol) in dry tetrahydrofuran (500 ml) at −70° C. under argon is added n-butyl lithium (1.6 m in hexane, 144 ml, 0.231 mol) over about 10 minutes. The mixture is allowed to warm to 15° C. during which time an orange solution forms. This mixture is re-cooled to −70° C., more n-butyl lithium (6 ml) is added, and after a further 15 minutes, a solution of 5-O-benzoyl-1,2-di-O-acetonide-3-ketoxylose prepared as described by H. S. Mosher. J. Org. Chem. 1986, 51, 2702 (50.0 g, 0.171 mol) in dry tetrahydrofuran (100 ml) is added in 5 batches over 35 minutes, whilst maintaining the reaction temperature at −66 to −70° C. The mixture is kept at −70° C. for 2 hours, then allowed to warm to +10° C. over 1.5 hours and maintained at this temperature for 3 hours. Acetic acid (3.5 ml) is added, followed by hexane (500 ml). The resultant precipitate is separated by filtration and the liquors passed through a pad of silica gel ca 2 cm deep). This pad is washed with ether (1 litre) and the filtrate is evaporated to yield a crude oil. The product is purified by flash column chromatography over silica gel (Merck, Art 15111, 10 cm Ø, 5 cm L) eluting with hexane then hexane: ether (3:1) mixtures to yield Compound 8 as a colourless solid, mp 61–62° C.

δH (CDCl$_3$) 8.10 (2H, d, Ph-H), 7.55 (1H, t, Ph-H), 7.41 (2H, t, Ph-H), 5.95 (1H, d, H-1), 5.50) (1H, s, C=CH), 5.35 (1H, s, C=CH), 5.10 (1H, m, H=4), 4.96 (1H, d, H-2), 4.55 (1H, dd, H-5), 4.40 (1H, dd, H-5), 1.55 (3H, s, CH$_3$), 1.40 (3H, s, CH$_3$) ppm.

δC (CDCl$_3$) 166.2 (COPh), 145.6, 133.1, 129.6, 128.3, 112.7, 112.6, 104.5, 81.6, 77.3, 65.6, 27.3, 27.0 ppm.

Found: C 66.5, H 6.4%; $C_{16}H_{18}O_5$ requires C 66.25, H 6.25%.

EXAMPLE 9

This example describes the preparation of a compound of formula

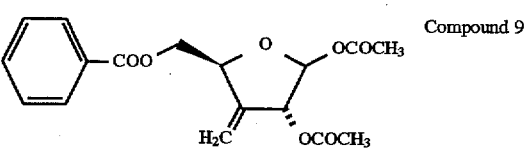

Compound 9

A mixture of Compound 8 (20.0 g, 68.9 mmol) in water (20 ml) and tetrahydrofuran (1 50 ml) and DOWEX® 50W×2 50–100 mesh ion-exchange resin (1 00 ml) is heated at reflux for 5 days. The mixture is filtered and the resin washed with dichloromethane (100 ml). The filtrates are evaporated and co-evaporated with toluene (3×100 ml) to yield a viscous orange oil. To a solution of this oil in dichloromethane (100 ml) at 0° C. is added pyridine (22 ml, 0.276 mol) and acetic anhydride (19.3 ml, 0.207 mol) and the mixture is stirred at 0° C. for 3 hours. The solvents are evaporated to yield the crude product which is purified by column chromatography over silica gel (Merck, Art 7734, 500 g) eluting with ether: hexane (1:10 to 4:10) mixtures. Fractions adjudged pure by thin layer chromatography are collected and evaporated to yield Compound 9 as a colourless oil, as a mixture 5:2 of α:β anomers at position 1.

Samples of each purified anomer are characterized:

α-anomer:

δH (CDCl$_3$) 8.03 (2H, d, Ph-H), 7.57 (1H, m, Ph-H), 7.44 (2H, t, Ph-H), 6.54 (1H, d, J=4.57 Hz, H-1, 5.69 (1H, m, H-2), 5.36 (2H, m, C=CH$_2$), 5.03 (1H, m, H-4), 4.54 (1H, dd, J=12.0, 3.3 Hz, H-5), 4.44 (1H, dd, J=12.0, 5.0 Hz, H-5), 2.15 (3H, s, COCH$_3$), 2.07 (3H, s, COCH$_3$) ppm.

δC (CDCl$_3$) 169.86, 169.62 (CH$_3$CO), 166.10 (PhC0), 141.01 (C-3) 133.17, 129.55, 129.45, 128.39 (Ph), 110.26 (C=CH$_2$), 93.77 (C-1), 79.62 (C-2), 72.30 (C-4), 65.87 (C-5), 20.91 (CH$_3$CO), 20.42 (CH$_3$) ppm.

β-anomer:

δH (CDCl$_3$) 8.07 (2H, d, Ph-H), 7.57 (1H, m, Ph-H), 7.44 (2H, t, Ph-H), 6.24 (1H, s, H-1), 5.73(1H, d, H-2), 5.56 (1H, m, C=CH), 5.49 (1H, m, C=CH), 5.10 (1H, m, H-4), 4.53 (1H, dd, J=11.9, 3.85 Hz, H-5), 4.44 (1H, dd, J=11.9, 6.7 Hz, H-5), 2.11 (3H, s, COCH$_3$), 2.01 (COCH$_3$) ppm.

δC (CDCl$_3$) 169.82, 169.25 (CH$_3$CO), 166.17 (PhCO), 142.56 (C-3), 138.14, 129.66, 128.32 (Ph), 116.17 (C=CH$_2$), 99.07 (C-1), 79.62 (C-2), 77.62 (C-4), 66.68 (C-5), 21.01 (CH$_3$CO), 20.88 (CH$_3$), ppm.

EXAMPLE 10

This example describes the preparation of a compound of formula

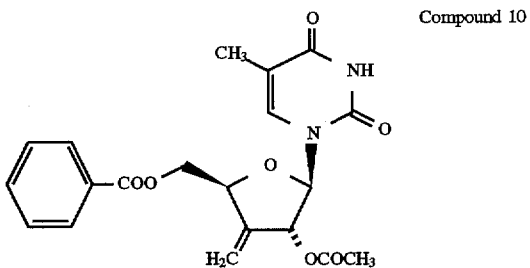

Compound 10

A suspension of thymine (4.38 g, 34.7 mmol) and bis (trimethylsilyl)acetamide (14.12 g, 69.4 mmol) is heated to 70° C. with stirring under argon for 2 hours. The resulting solution is allowed to cool to 22° C. over 2 hours. A solution of Compound 9 (11.6 g, 34.7 mmol) in 1,2-dichloroethane (15 ml) is added to the above reaction mixture with stirring at 22° C. Trimethylsilyl trifluoromethane sulphonate (9.25 g, 41.6 mmol) is then added, dropwise, over 15 minutes. The reaction mixture is heated to 50° C., with stirring, for 3 hours. A solution of saturated aqueous sodium hydrogen carbonate (80 ml) is added slowly to the mixture and, when effervescence ceases, this is transferred to a separating funnel. The products are extracted into chloroform (4×50 ml) and the extracts washed with brine before drying (magnesium sulphate). Evaporation affords the crude product (15.0 g). Purification by flash column chromatography over silica gel (Merck, Art 15111, 4 cm×10 cm L) eluting with hexane, then hexane:ethyl acetate (1:1) mixtures, affords after evaporation of those appropriate fractions ajudged pure by thin layer chromotography, Compound 10 as a colourless glassy solid mpt. 55°–58° C.

$^1$H NMR (CDCl$_3$) δ 8.95 (1H, bs, NH), 8.04 (2H, m, Ph-H). 7.61 (1H, m, Ph-H), 7.48 (2H, m Ph-H), 7.17 (1H, d, J=1.3H thymine-H), 6.07 (1H, d, J=5.7 Hz, H-1), 5.74 (1H, m, H-2'), 5.49 (1H, m, C=CH), 5.41 (1H, m, C=CH), 5.03 (1H, m, H-4'), 4.71 (1H, dd, J=12.3, 2.8 Hz, H-5'), 4.54 (1H, dd, J=12.3, 4.4 Hz, H-5'), 2.15 (3H, s, COCH$_3$), 1.65 (3H, d, J=1.0 Hz CH$_3$) ppm.

$^{13}$C NMR (CDCl$_3$) δ 170.29 (CH$_3$C(O)), 166.04 (Ph C(O)), 163.65 (C-2) 150.62 (C-4), 141.70 (C-3$^1$), 134.56 (C-6), 133.46, 129.43, 129.28, 128.60, (Ph), 112.76 (C=CH$_2$), 111.85 (C-5), 86.72 (C-1$^1$), 78.20 (C-2$^1$), 75.32 (C-4$^1$), 65.42 (C-5$^1$), 20.65 (CH$_3$C(O)), 12.15 (CH$_3$) ppm.

Found: C 59.6, H 5.25, N 6.7%; C$_{20}$H$_{20}$N$_2$O$_7$ requires C 60.0, H 5.03, N 7.00%.

EXAMPLE 11

This Example describes the preparation of a compound of formula

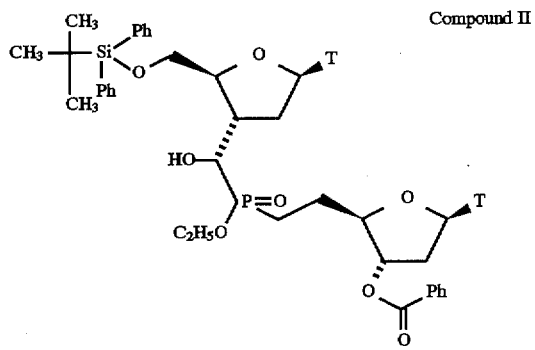

Compound II where Ph is phenyl and T is 1-thyminyl.

To a solution of Compound 5 (2.02 g, 4.56 mmole) and an aldehyde of formula IV where B$^{1-}$ is 1-thyminyl, R$^5$ is hydrogen and R$^6$ is tert-butyldiphenylsilyl (2.25 g, 4.53 mmol) in dry THF (30 ml) under argon at room temperature is added 1,8-diazabicyclo[5.4.0]undec-7-ene (DBU) (0.68 ml, 4.55 mmole). The resulting solution is stirred at room temperature for 2 hours. Concentration and purification by flash silica column chromatography (gradient elution 20:1–10:1 chloroform, ethanol) gives Compound 11 as a white foam, isolated as a mixture of four diastereoisomers.

Found C.57.45%, H 6.2%, N 5.7%; C$_{47}$H$_{57}$N$_4$O$_{12}$PSi.3H$_2$O requires C 57.4, H 6.45, N 5.7%.

$^{31}$P n.m.r $^1$H decoupled (CDCl$_3$, 162 MHz) δ 54.3, 53.5, 53.3, 52.7 ppm.

M/Z (FAB$^+$) 951 (MNa$^+$)

EXAMPLE 12

This Example describes the preparation of a compound of formula

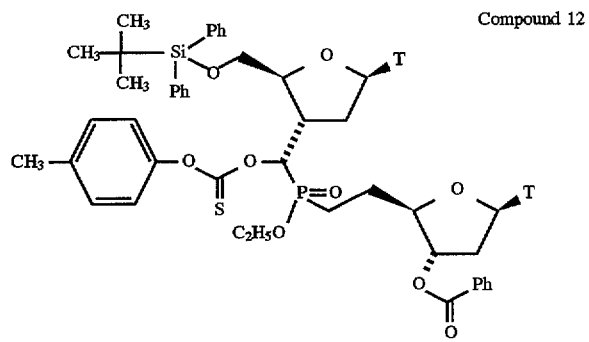

Compound 12 where Ph is phenyl and T is 1-thyminyl.

To a stirred solution of Compound 11 (5.75 g, 6.22 mmole) and dimethylaminopyridine (0.76 g, 6.22 mmole) in dry dichloromethane (80 ml) under an atmosphere of argon is added triethylamine (0.86 ml, 6.18 mmole). The resulting solution is cooled to 0° C. and p-tolylchlorothionoformate (1.05 ml, 6.81 mmole) is added dropwise over 5 minutes. The solution is allowed to warm to ambient temperature and stirring continued for 18 hours. The resulting mixture is diluted with dichloromethane (200 ml), washed with sodium dihydrogen phosphate (0.5 molar, 2×60 ml) and dried over magnesium sulphate. Concentration and purification by flash silica column chromatography (eluant chloroform/ethanol 30:1) gives Compound 12 as an off-white foam as a mixture of four diastereoisomers.

Found C 59.3%, H 6.0%, N 5.0%, P 2.5%; C$_{55}$H$_{63}$N$_4$O$_{13}$PS Si.2H$_2$O requires C 59.25, H 6.05%, N 5.0%, P 2.8%

$^{31}$P n.m.r. $^1$H decoupled (CDCl$_3$, 162 MHz) δ 47.9, 47.6, 47.3 ppm.

M/Z (FAB$^+$) 1101.6 (MNa$^+$)

EXAMPLE 13

This Example describes the preparation of a compound of formula

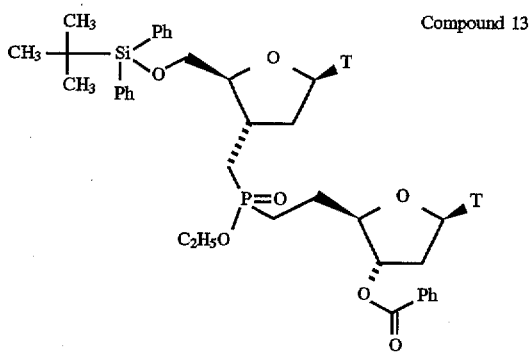

Compound 13 where Ph is phenyl and T is 1-thyminyl.

To a solution of Compound 12 (800 mg, 0.74 mmole) and tributyltin hydride (0.28 ml, 0.89 mmole) in degassed toluene (10 ml) under argon at 100° C. is added azobis (isobutyryl nitrile) (5 mg). After heating at 100° C. for 5 hours the crude mixture is concentrated and partitioned between acetonitrile (50 ml) and hexane (50 ml). The acetonitrile layer is separated and extracted with hexane (8×50 ml). Concentration gives an off-white foam which is purified by flash silica column chromatography (gradient elution, chloroform-ethanol 30:1–18:1) to give Compound 13 as a mixture of diastereoisomers which are partially separated by the above purification.

Found C 61.1, H 6.4, N 6.0%, $C_{47}H_{57}N_4O_{11}P$ Si.½$H_2O$ requires C 61.2, H 6.35, N 6.1%

1st Diastereoisomer $^{31}P$ nmr (162 MHz, $CDCl_3$) δ 54.8 ppm.

2nd Diastereoisomer $^{31}P$ nmr (162 MHz $CDCl_3$) δ 54.3 ppm.

M/Z ($FAB^+$) 935 ($MNa^+$)

EXAMPLE 14

This Example describes the preparation of a compound of formula

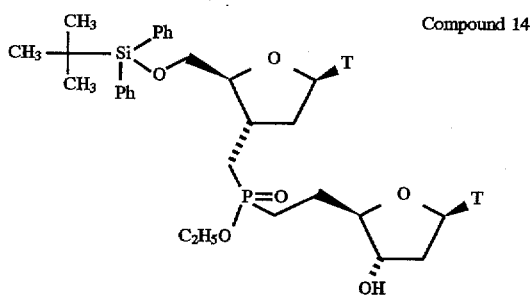

Compound 14 where Ph is phenyl and T is 1-thyminyl.

To a solution of Compound 13 (60 mg, 0.066 mmole) in dry ethanol (1 ml) under argon is added sodium (1 mg, 0.04 mmole). After 18 hours at room temperature, acetic acid (6 µl, 0.1 mmole) is added. Concentration and passage through a short plug of silica (5:1 dichloromethane/ethanol, 10 ml) gives a crude oil which is purified by flash silica column chromatography (eluant dichloromethane/ethanol 8:1) to give Compound 14 as a white foam, isolated as a mixture of diastereoisomers at phosphorus which are partially separable by the above purification.

Found: C 58.6, H 7.0, N 6.6, P 3.5%; $C_{40}H_{53}N_4O_{10}PSi.¾H_2O$ requires C 58.4, H 6.7, N 6.8, P 3.75%.

$^{31}P$ nmr 1H decoupled ($CDCl_3$, 162 MHz), δ 55.9, 55.7 ppm.

M/Z ($FAB^+$) 831 ($MNa^+$)

EXAMPLE 15

This Example describes the preparation of a compound of formula

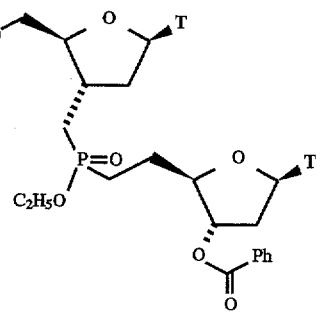

Compound 15 where Ph is phenyl and T is 1-thyminyl.

To a solution of Compound 13 (190 mg, 0.21 mmole) and acetic acid (12 µl, 11, 0.21 mmole) in dry THF (5 ml) at ambient temperature is added a solution of tetra-n-butylammonium fluoride (0.21 mmole) in THF (208 µl). The resulting solution is stirred for 2 hours at room temperature, and concentrated. Purification by flash silica column chromatography (eluant chloroform/ethanol 10:1) gives Compound 15 as a white foam and as a mixture of 2 diastereoisomers at phosphorus.

Found: C 49.8, H 5.6, N 7.1, P 3.9%; $C_{31}H_{39}N_4O_{11}P.½H_2O.½CHCl_3$ requires C 49.7, H 5.65, N 7.35, P 4.05%.

$^{31}P$ nmr $^1H$ decoupled ($CDCl_3$, 162 MHz) δ 56.1, 55.9 ppm.

M/Z ($FAB^+$) 675 ($MH^+$)

EXAMPLE 16

This Example describes the preparation of a compound of formula

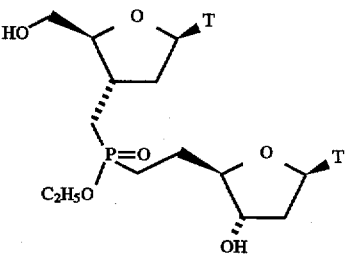

Compound 16 where T is 1-thyminyl.

To a solution of Compound 15 (116 mg, 0.17 mmole) in dry ethanol (2 ml) under argon is added sodium (8 mg, 0.34 mmol). After 18 hours at ambient temperature acetic acid (30 µl, 0.51 mmol) is added. Concentration and passage through a short plug of silica (2:1 ethyl acetate:ethanol) gives a crude oil which is purified by flash silica column chromatography (eluant:ethyl acetate/ethanol 3:1) to give Compound 16 together with recovered starting material. The product is isolated and characterised as a mixture of diastereoisomers at phosphorus.

Found: C 48.1, H 6.5, N 9.1, P 5.15%; $C_{24}H_{35}N_4O_{10}P.½H_2O$ requires C 48.25, H 6.4, N 9.4, P 5.2%.

$^{31}$P nmr $^1$H decoupled (162 MHz, CDCl$_3$) δ 57.9, 57.7 ppm.

M/Z (FAB$^+$) 571 (MH$^+$)

EXAMPLE 17

This Example describes the preparation of a compound of formula

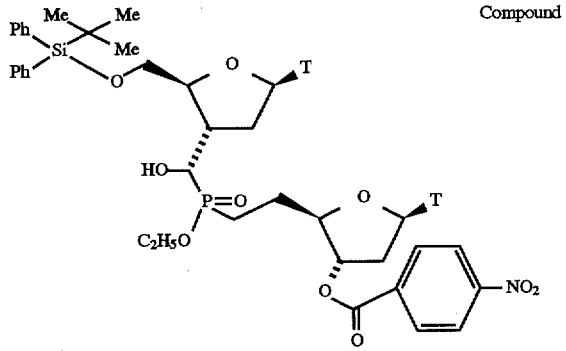

Compound 17 where Me is methyl, Ph is phenyl and T is 1-thyminyl.

To a solution of Compound 7 (0.38 g, 0.79 mmole) and an aldehyde of formula IV where B$^1$ is 1-thyminyl, R$^5$ is hydrogen and R$^6$ is tert-butyldiphenylsilyl (0.30 g, 0.61 mmole) in dry THF (3 ml) under argon at room temperature is added 1,8-diazabicyclo[5.4.0]undec-7-ene (DBU) (0.11 ml, 0.74 mmole). The resulting solution is stirred at room temperature for 3 hours. Concentration and purification by flash silica column chromatography (gradient elution 25:1–12:1 chloroform:ethanol) gives Compound 17 as a white foam isolated as a mixture of 4 diastereoisomers.

$^{31}$P nmr $^1$H recoupled (162 MHz, CDCl$_3$) δ 54.7, 54.0, 53.6, 52.8 ppm.

EXAMPLE 18

This describes the preparation of a compound of formula

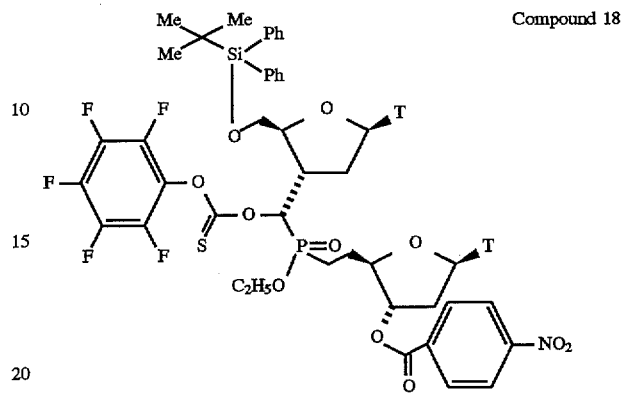

Compound 18 where Me is methyl, Ph is phenyl and T is 1-thyminyl.

To a stirred solution of Compound 17 (109 mg, 0.11 mmole) and dimethylaminopyridine (16.4 mg, 0.13 mmole) in dry dichloromethane (1 ml) under an atmosphere of argon at 0° C. is added pentafluorophenyl chlorothionoformate (20 μl, 0.12 mmole). The resulting solution is allowed to warm to room temperature. After 24 hours, concentration and purification by flash silica column chromatography gives the Compound 18, isolated as a mixture of 4 diastereoisomers.

$^{31}$P nmr $^1$H decoupled (162 MHz, CDCl$_3$) δ 47.3, 47.2, 46.6 ppm.

EXAMPLE 19

Treatment of Compound 18 by the procedure of Example 13 gives a compound of formula

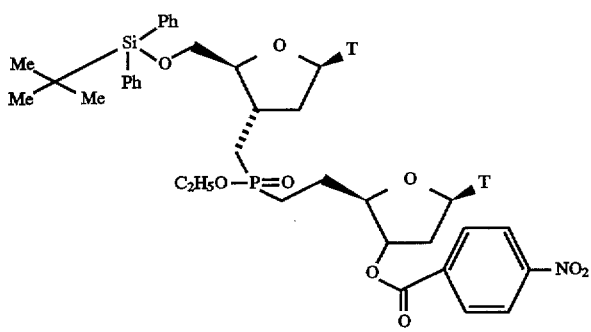

Compound 19 where Me is methyl, Ph is phenyl and T is 1-thyminyl.

EXAMPLE 20

This Example describes the preparation of a compound of formula

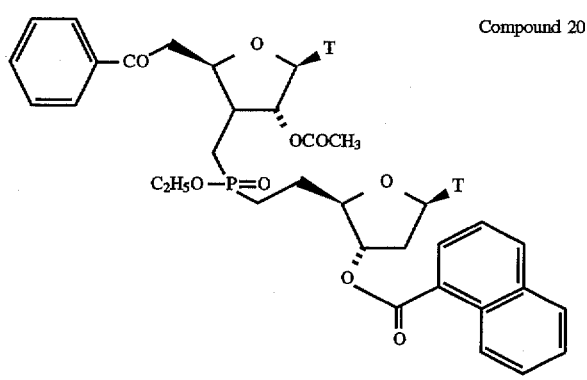
Compound 20 where T is 1-thyminyl.

To a heated (90° C.) solution of Compound 6 (72 mg, 0.15 mmole) and Compound 10 (52 mg, 0.13 mmole) in toluene (0.25 ml) under argon is added tert-butylcyclohexyl perdicarbonate (5 mg) as initiator. The addition of initiator is repeated every 30 minutes. After 3 hours, concentration and purification by flash silica column chromatography (ethylacetate:methanol mixtures) gives Compound 20 as a mixture of 4 diastereoisomers.

$^{31}P$ nmr $^1H$ decoupled ($CDCl_3$, 162 MHz) δ 54.1, 54.4, 54.5, 54.6 ppm.

EXAMPLE 21

This Example describes the preparation of the compound of formula

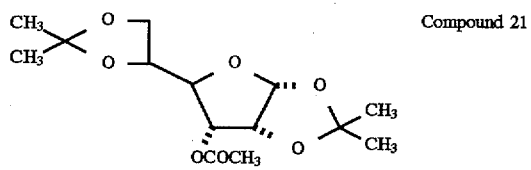
Compound 21

A mixture of 1,2,5,6-di-O-isopropylidene-a-D-allofuranose (the diacetonide of formula XXII) prepared according to Carbohyd. Res. 24(1972) 192 (55.72g., 0.214M), acetic anhydride (100 ml), and pyridine (50 ml) is stirred at room temperature for 3 hours. The solution is evaporated then co-evaporated with methanol three times to remove the excess of acetic anhydride and pyridine. The residue is dissolved in dichloromethane (200 ml), washed several times with water and dried (Mg $SO_4$). Evaporation gives a white solid, m.p.t.75° C., $[\alpha]_D^{25}$+109.4° C., 1.03 $CHCl_3$.

Found C 55.5, H 7.30; Calculated for $C_{14}H_{22}O_7$ C 55.6, H, 7.3%

EXAMPLE 22

This Example describes the preparation of the compound of formula

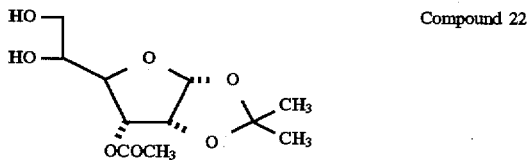
Compound 22

Compound 21 (65 g 0.215M) is dissolved in 80% acetic acid (250 ml) and allowed to stand for 60 hours. The acetic acid is removed by evaporation and co-evaporation with methanol to give a pale yellow oil. This oil is chromatographed on silica (750 g) using ethyl acetate eluant to give Compound 22 as a colourless oil. $[\alpha]_d^{20}$+125.2° C., 1.15 $CHCl_3$ Found C 50.1, H7.0; Calculated for $C_{11}H_{18}O_7$ C50.4, H6.9%

EXAMPLE 23

This Example describes the preparation of the compound of formula

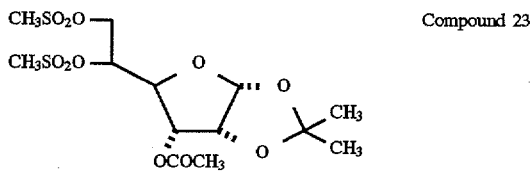
Compound 23

Compound 22 (45.9 g, 0.175M) in pyridine (180 ml) under argon is cooled to 5° C. and methanesulphonyl chloride (60.1 g, 0.525M) is added over 1 hour. The temperature is allowed to rise to room temperature and the mixture is stirred for a further 2.5 hours until the reaction, monitored by thin layer chromatography (TLC), appears complete. Chloroform (200 ml) and hydrochloric acid (2N, 300 ml), are added and the mixture is stirred for 5 minutes. The organic phase is separated, washed with sodium bicarbonate (250 ml) then brine (250 ml) and dried ($MgSO_4$). Evaporation of solvent gives a yellow oil (70 g) which is purified by flash chromatography using ether eluant to give Compound 23, m.p.t. 84°–5° C., $[\alpha]_D^{25}$+109.6° C. 0.75;

Found C 37.3, H5.3; Calculated for $C_{13}H_{22}O_{11}S_2$, C37.3, H5.3%.

EXAMPLE 24

This Example describes the preparation of the compound of formula

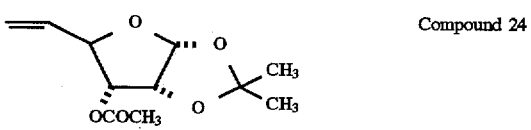
Compound 24

A mixture of Compound 23 (65 g, 0.155M) and sodium iodide (94 g, 0.62M) in butan-2-one (1.51) is heated to reflux for 5 hours. A further 10% of sodium iodide is added and heating continued for 3 hours. The solvent is removed and the dark brown residue is partitioned between chloroform and water. Sodium thiosulphate is added portionwise until the solution is colourless. The chloroform extracts are separated, washed with sodium bicarbonate then brine and dried ($MgSO_4$). Evaporation gives a pale yellow oil (35 g, 100%) which is purified by chromatography on silica using hexane: ethyl acetate, 2:1, eluant, to give Compound 24. An analytical sample is obtained by bulb to bulb distillation (100° C./0.1 mm Hg), $[\alpha]_D^{25}$+107.5° C., 1.13 $CHCl_3$;

Found $C_{58.0}$, H 7.0; $C_{11}H_{16}O_5$ requires $C_{57.9}$, H 7.1%.

EXAMPLE 25

This Example describes the preparation of the compound of formula

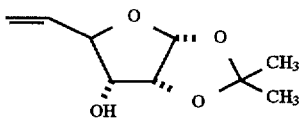

Compound 25

Compound 24 (15 g 0.066M) dissolved in methanol (100 ml) is added to a solution of potassium carbonate (22.7 g, 0.165M) in water (100 ml). After 15 minutes the reaction is complete (TLC). The solvent volume is reduced to 50 ml and after further co-evaporation with water the residue is washed with chloroform (3×100 ml). The chloroform extracts are washed with brine then dried (MgSO$_4$). Evaporation gives a white solid, m.p.t. 67.5°–68° C., $[\alpha]_D^{25}$+38.2° C., 0.95 CHCl$_3$.

Found C 57.8, H 8.0; Calculated for C$_9$H$_{14}$O$_4$, C 58.05, H 7.6%.

EXAMPLE 26

This Example describes the preparation of the compound of formula

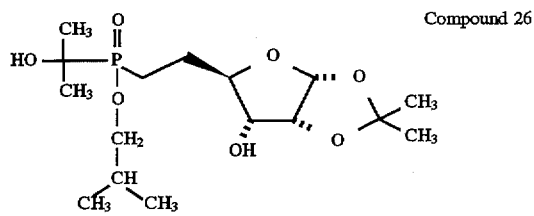

Compound 26

A solution of isobutyl (1-hydroxy-1-methylethyl) phosphinate (7.22 g, 0.0403M) and t-butylcyclohexylperdicarbonate (0.5 g) in toluene (1 ml) is heated to 80° C. and stirred under argon. A solution of Compound 25 and t-butyl cyclohexylperdicarbonate (2 g) in toluene (4 ml) is added slowly over 30 minutes and the mixture is stirred for 4 hours. When reaction is complete (monitored by ⁻p nmr) the solvent is stripped to give a pale yellow oil. The oil is chromatographed on silica using ether, ethyl acetate and finally 5% methanol in ethyl acetate gradient as eluants. There is obtained Compound 26 as an oil which partly solidifies.

Found C 52.7, H8.5, P8.7; C$_{16}$H$_{30}$O$_7$P requires C 52.6, H8.3 P8.5%.

$^{31}$P nmr (CDCl$_3$, 162 MHz): δ 56.85, 57.2 ppm.

EXAMPLE 27

This Example describes the preparation of the compound of formula

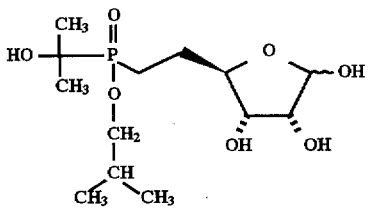

Compound 27

To Compound 26 (8.25 g, 0.0226M) in dimethoxyethane (200 ml) is added a slurry (50 ml) of Dowex 50 W×2 (100), H$^+$ form, in water and the mixture is heated to 80° C. for 12 hours then cooled. The Dowex is removed by filtration to give a pale yellow solution. Evaporation of the solvent gives Compound 27 as an oil which is not purified further.

$^{31}$P nmr (CD$_3$OD, 162 MHz): δ=63.2, 63.4, 64.3 and 64.4 ppm.

EXAMPLE 28

This Example describes the preparation of the compound of formula

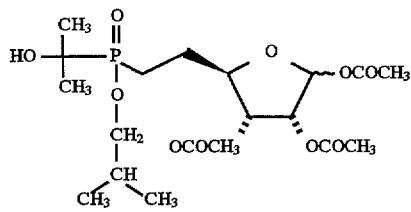

Compound 28

Compound 27 (20 g, 0.0613M) is added to a mixture of pyridine (40 ml) and acetic anhydride (40 ml) with cooling, maintaining the temperature below 30° C. Reaction is complete in 20 minutes (Monitored by TLC). The excess of acetic anhydride and pyridine are removed by evaporation. The residual oil is dissolved in chloroform and washed with dilute hydrochloric acid, sodium bicarbonate and brine and dried over MgSO$_4$. Evaporation gives a yellow syrup which is purified by chromatography with silica. There is obtained Compound 28.

Found C50.4; H7.15, P6.65; C$_{19}$H$_{32}$O$_{10}$P requires C$_{50.55}$, H 7.15, P 6.9%.

$^{31}$P nmr (CDCl$_3$, 162 MHz): δ 55.5, 55.7, 55.8 ppm.

EXAMPLE 29

This Example describes the preparation of the compound of formula

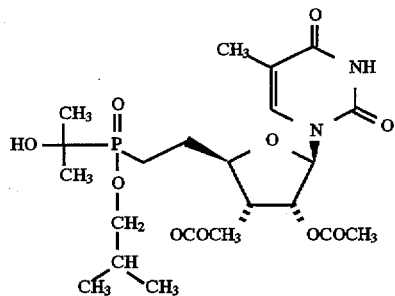

Compound 29

A mixture of thymine (6.31 g, 0.05M), N, O-bis trimethylsilyl acetamide (20.34 g, 0. 1M) and dichloroethane (125 ml) is heated to 80° C. under argon until a clear solution is obtained. The solution is cooled to room temperature and a solution of Compound 28 (22.57 g, 0.05M) in dichloroethane (75 ml) is added followed by trimethylsilytrifluoromethane sulphonate (32.91 g, 0.125M). The reaction mixture is heated to 50° C. and stirred for 8 hours until reaction is complete (TLC). Chloroform (300 ml) and water (200 ml) are added followed by saturated sodium bicarbonate solution until the aqueous phase is neutral. The mixture is washed with chloroform (3×100 ml) and the extracts are washed with water then brine and dried (MgSO$_4$).

Evaporation gives a viscous liquid which is chromatographed on silica using 5% methanol in chloroform as eluant. There is obtained a colourless oil which is dissolved in acetic acid, water and tetrahydrofuran (100 ml 3:1:1 ratio) and heated on a steam bath for 15 minutes. The solvent is removed by evaporation followed by co-evaporation with methanol then chloroform. There is obtained Compound 29 as a white hygroscopic solid.

Found C 50.9, H6.9, N5.2, P5.9; $C_{22}H_{35}O_{10}N_2P$ requires C 50.95, H 6.8, N5.4, P5.9%.

$^{31}P$ nmr (CDCl$_3$, 162 MHz): δ 56.0, 56.3 ppm.

EXAMPLE 30

This Example describes the preparation of the compound of formula

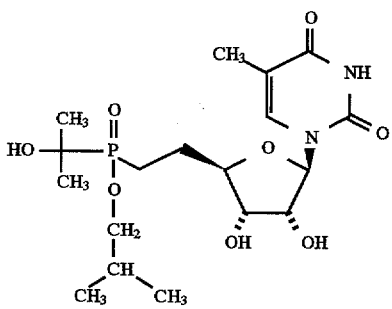

Compound 30

Compound 29 (4.4 g, 0.0085M) dissolved in methanol (5 ml) is added to potassium carbonate (2.34 g, 0.017M) in water (5 ml) and the mixture is stirred for 15 minutes. The mixture is evaporated to dryness and the residue is stirred with acetone. The inorganic solids are removed by filtration and the acetone is evaporated to give Compound 30 as an oil.

$^{31}P$ nmr (C20, 162 MHz): δ=63.0 ppm.

EXAMPLE 31

This Example describes the preparation of

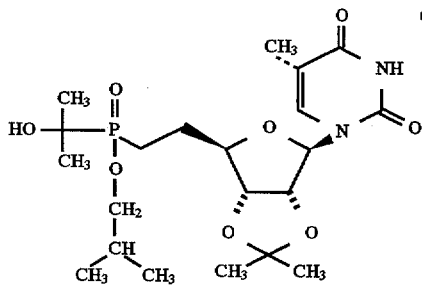

Compound 31

A mixture of Compound 30 (2.0 g, 0.0046M) 2,2-dimethoxypropane (20 ml), dimethylformamide (20 ml) and p-toluene sulphonic acid (0.1 g), is heated at 100° C. for 2.5 hours. The solution is concentrated to 10 ml, water (50 ml) is added and the product is extracted with ethyl acetate (3×50 ml). Concentration of the ethyl acetate phase gives an oil which is chromatographed on silica using 4% methanol in chloroform. There is obtained Compound 31.

$^{31}P$ nmr (CDCl$_3$, 162 MHZ) δ=56.05 ppm, 56.19 ppm.

EXAMPLE 32

This Example describes the preparation of

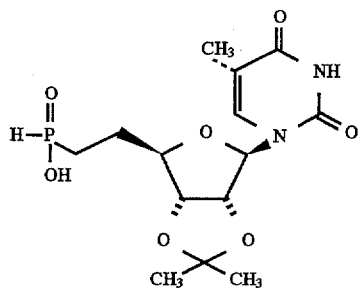

Compound 32

Compound 31 (1.71 g, 0.0036M) is heated in aqueous ammonia (10%, 20 ml) at 80° C. for 4 hours. Evaporation gives an oil which is stirred in methanol (10 ml) with Dowex 50 W×2 (2 g). Filtration and evaporation of the solvent gives Compound 32.

$^{31}P$ nmr (CD$_3$OD, 162 MHZ) δ=37.35 ppm, $J_{PH}$=540 Hz.

EXAMPLE 33

This Example describes the preparation of

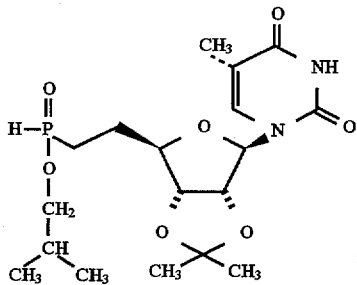

Compound 33

Compound 32 (0.8 g, 0.0022M), 2-methylpropanol (0.25 ml, 0.0026M), dimethylaminopyridine (0.1 g) in tetrahydrofuran (10 ml) are stirred at room temperature. Dicyclohexylcarbodimide (0.55 g, 0.0026M) is added and stirring is continued for 3 hours. The precipitate is filtered off and the filtrate is stripped to give an oil which is chromatographed on silica using ethyl acetate then a gradient of 5% methanol in ethyl acetate. There is obtained Compound 33.

$^{31}P$ nmr (CDCl$_3$ 162 MHZ) δ=39.2 ppm, $J_{PH}$=540 Hz.

EXAMPLE 34

This Example describes the preparation of

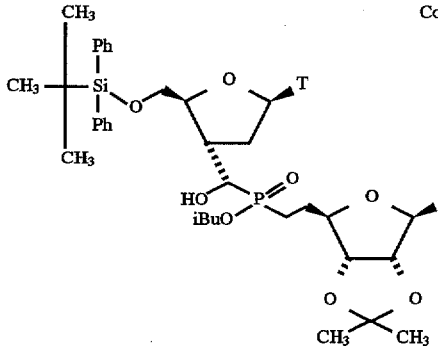

Compound 34 where Ph is phenyl, iBu is isobutyl and T is 1-thyminyl.

To a solution of Compound 33 (0.0833 g, 0.2 mmole) and an aldehyde of formula IV where $B^1$ is 1-thyminyl, $R^5$ is hydrogen and $R^6$ is tert-butyldiphenylsilyl (0.0985 g, 0.2 mmole) in dry THF (1 ml) under argon at room temperature is added 1,8-diazabicyclo[5.4.0]undec-7-ene (DBU) (0.03 ml, 0.2 mmole). The solution is stirred at room temperature for 4 hours. Concentration and purification by chromatography on silica gives Compound 34 as a viscous oil isolated as a mixture of four diastereoisomers.

$^{31}$P nmr (CDCl$_3$, 162 MHz) δ 54.8, 53.9, 53.0 and 52.6

EXAMPLE 35

This example describes the preparation of Compound 35

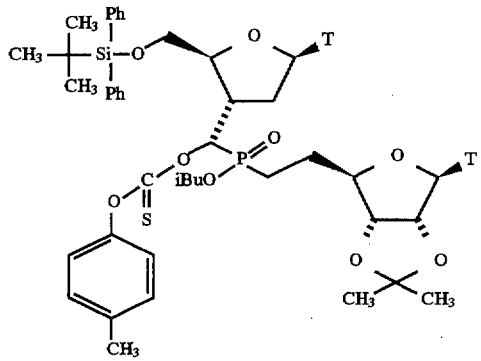

where T is 1-thyminyl 1, Ph is phenyl and iBu is isobutyl.

To a mixture of compound 34 (1.0 g, 1.08 mmole), triethylamine (0.109 g, 1.08 mmole), dimethylaminopyridine (0.27 mmole) in dichloromethane (50 ml) at 5° C. is added p-tolylchlorothionoformate (0.22 g, 1.19 mmole). The solution is allowed to warm to room temperature and stirred for 2 hours. More p-tolychlorothionoformate (0.55 g., 0.3 mmole) and dimethylaminopyridine (0.07 mmole) are added and the mixture is stirred for five days. The resulting mixture is washed with NaHCO$_3$, dilute HCl, water and brine and then dried (MgSO$_4$). The solvent is removed and the residue purified on silica using methanol (5%) in chloroform as eluant. There is obtained Compound 35 as an off-white solid as a mixture of four diastereoisomers.

$^{31}$P nmr (CDCl$_3$, 162 MHz) δ 47.06, 47.37, 47.89, 48.65 ppm

EXAMPLE 36

This example describes the preparation of Compound 36:

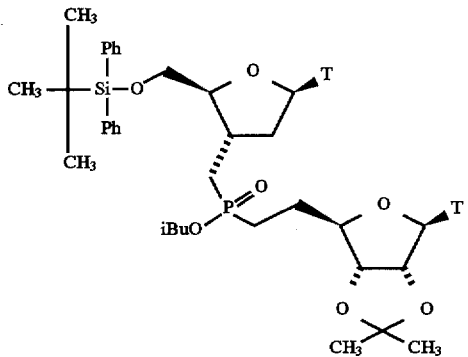

where T is 1-thyminyl, Ph is phenyl and iBu is isobutyl.

To a mixture of Compound 35 (0.48 g, 0.45 mmole), tributyltinhydride (0.158 g, 0.54 mmole), in degassed toluene (5 ml) at 100° C. under argon is added azobis (isobutyronitrile) (2.5 mg) and the mixture is heated for 4 hours. The resulting mixture is concentrated and the residue is dissolved in acetonitrile (25 ml) and washed with hexane (3×25 ml). The acetonitrile phase is evaporated to an oil which is purified on silica using methanol (5%) in chloroform as eluant. There is obtained Compound 36 as a white foamy solid as a mixture of diastereoisomers.

$^{31}$Pnmr. (CDCl$_3$, 162 MHz) δ 54.61, 54.67 ppm

M/Z(FAB$^+$) 915(MNa$^+$)

EXAMPLE 37

This example describes the preparation of Compound 37:

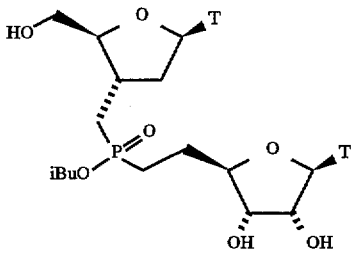

Compound 37 where T is 1-thyminyl and iBu is isobutyl.

Compound 36 (0.26g., 0.279 mmole) is dissolved in tetrahydrofuran (10 ml) and dilute hydrochloric acid (2M 10 ml) is added. The milky solution is heated at 70° C. and the resulting clear solution stirred and heated for 24 hours. The solvent is removed and the residue is dissolved in water (10 ml). The solution is washed successively with ether and ethylacetate, then evaporated to dryness. There is obtained Compound 37 as a mixture of diastereoisomers.

$^{31}$P nmr. (CD$_3$OD, 162 MHz) δ 59.61, 59.96 ppm.

EXAMPLE 38

This example described the preparation of

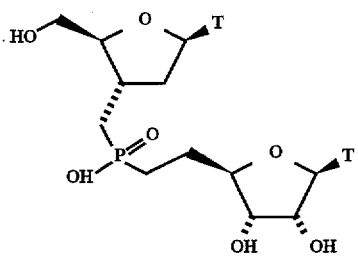

Compound 38 where T is 1-thyminyl.

Compound 37 (0.104 g., 0.169 mmole) is dissolved in aqueous sodium hydroxide ( 1M., 10 ml.). The solution is heated to 40° C. for 3 hours and then stood overnight at room temperature.

$^{31}$P nmr indicates hydrolysis to the sodium salt (δ 42.9 ppm(singlet)). Dowex 50 W×2 ion exchange resin (20 ml. slurry) is added and the mixture is stirred for 5 minutes. The mixture is filtered and the filtrate evaporated to a white solid, which is lyophilized. There is obtained Compound 38 as a white solid.

$^{31}$Pnmr (D$_2$O, 162 MHz) δ 48.81 ppm. $^1$H and $^{13}$Cnmr confirm the structure of Compound 38.

EXAMPLE 39

The example describes the preparation of a compound of formula

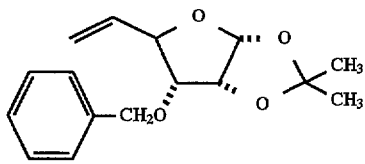

Compound 39

Sodium hydride (4.0 g, 0.1M, 60% dispersion in oil) is rinsed with petroleum ether (40°–60° C.) and added to tetrahydrofuran (75 ml) under argon. The mixture is cooled to −10° C. and Compound 25 (18.62 g, 0.1M) in tetrahydrofuran (50 ml) is added dropwise maintaining the temperature at −5° C. The solution is warmed to 5° C. and benzyl bromide (11.9 ml, 0.1M) and tetra-n-butylammonium iodide (0.37 g, 0.001M) in tetrahydrofuran (25 ml) are added slowly. The mixture is allowed to warm to room temperature and stirred for a further three hours when reaction is complete (monitored by T.L.C. in ether). Florisil (5 g) is added and the solvent is evaporated. The residue is mobilised with hexane (50 ml) and the solids are filtered off. The filtrate is evaporated to a yellow oil which is purified by 'bulb to bulb' distillation (150° C., 1 mm Hg) to give 26.9 g oil. This oil is chromatographed on silica using 10% ethyl acetate in petroleum ether (40°–60°) to give Compound 39.

Found: C 69.6, H 7.5%; calculated for $C_{16}H_{20}O_4$, C 69.5, H 7.2%.

EXAMPLE 40

This Example describes the preparation of

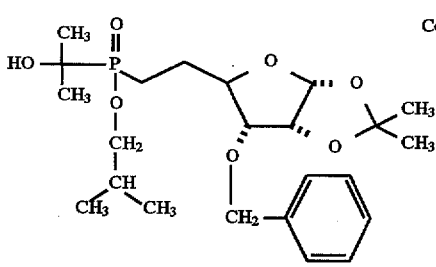

Compound 40

A solution of isobutyl(1-hydroxy-1-methylethyl)phosphinate (12.6 g, 0.07M) and tert-butylcyclohexylperdicarbonate (0.5 g) in toluene (2 ml) is heated at 80° C. under argon. Compound 39 (19.34 g, 0.07M) in toluene (2 ml) is added portionwise over 2 hours. A further 2.5 g perdicarbonate in toluene (6 ml) is added over 2 hours. The reaction mixture is stirred for a further 10 hours, adding perdicarbonate (0.25 g) every 2 hours when the reaction appears complete ($^{31}$P nmr). The mixture is cooled and evaporated to a gum which is purified on silica by flash chromatography using ethyl acetate, then 5% methanol in ethyl acetate, as eluants. The methanolic eluates are re-chromatographed on silica using 5% methanol in ethyl acetate as eluant to give Compound 40.

$^{31}$P nmr (CDCl$_3$ 162 MHz) δ=56.0, 56.2 ppm

EXAMPLE 41

This Example describes the preparation of

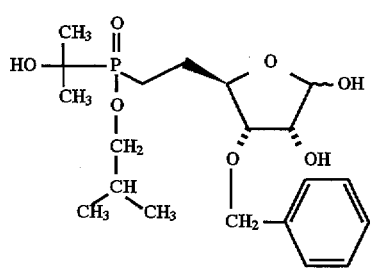

Compound 41

Compound 40 (15.07 g, 0.033M), tetrahydrofuran (150 ml) and dilute hydrochloric acid (150 ml, 1M) are stirred at room temperature for 24 hours, then at 40° C. for 8 hours. The resulting solution is neutralised with solid sodium bicarbonate and then evaporated. The residue is dissolved in water and washed with ethyl acetate (3×50 ml). The organic extracts are washed with brine and dried (MgSO$_4$). Evaporation of the solvent gives Compound 41, which is further purified by chromatography on silica using 5% methanol in ethyl acetate.

Found: C 57.5, H 8.4%;

$C_{20}H_{33}O_7P$ requires C 57.68, H 7.99%

$^{31}$P nmr (CDCl$_3$ 162 MHz) δ=56.7, 56.9, 57.3, 57.8 ppm

EXAMPLE 42

This Example describes the preparation of Compound 42.

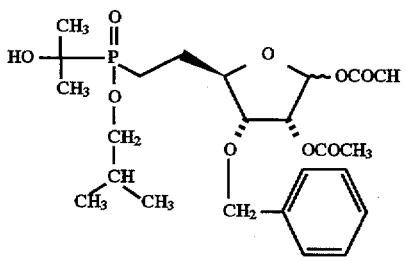

Compound 42

Compound 41 (10.41 g, 0.025M) and acetic anhydride (100 ml) in pyridine (100 ml) are allowed to stand at room temperature for 18 hours. The solution is evaporated to dryness and the residue is dissolved in chloroform (100 ml), washed successively with dilute hydrochloric acid (100 ml), sodium bicarbonate (100 ml), brine (100 ml) and then finally dried (MgSO$_4$). Evaporation gives Compound 42, which is used directly in the preparation of Compound 43.

$^{31}$P nmr (CDCl$_3$, 162 MHz) δ=55.5, 55.7, 55.9 ppm.

EXAMPLE 43

This Example describes the preparation of Compound 43

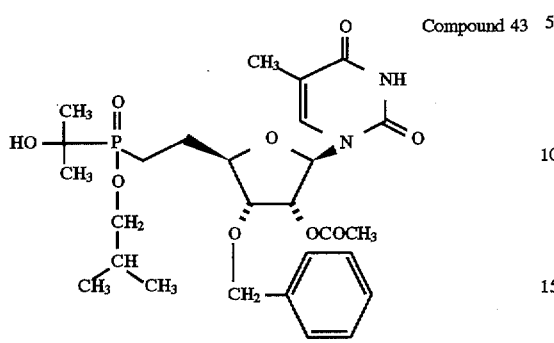

A mixture of thymine (2.02 g, 0.004M) N,O-bistrimethylsilylacetamide (1.63 g, 0.008M) and dichloroethane (10 ml) is heated at 80° C. under argon for 2 hours to give a colourless solution.

The solution is cooled to room temperature and a solution of Compound 42 (2.02 g, 0.004M) in dichloroethane (15 ml) is added followed by trimethylsilyltrifluoromethane sulphonate (2.67 g, 0.012M). The mixture is heated at 50° C. for 3 hours. The resulting yellow solution is cooled and added to water (20 ml). Sodium bicarbonate is added until the pH is neutral. The aqueous phase is extracted with dichloromethane (3×10 ml) and the organic extracts are washed with brine and then dried (MgSO$_4$). Evaporation gives a white solid which is purified by chromatography using silica and a gradient of 2–5% methanol in ethyl acetate as eluant. There is obtained Compound 43 as a white hygroscopic solid.

$^{31}$P nmr (CDCl$_3$ 162 MHz) δ=56.3 ppm.

EXAMPLE 44

This Example describes the preparation of

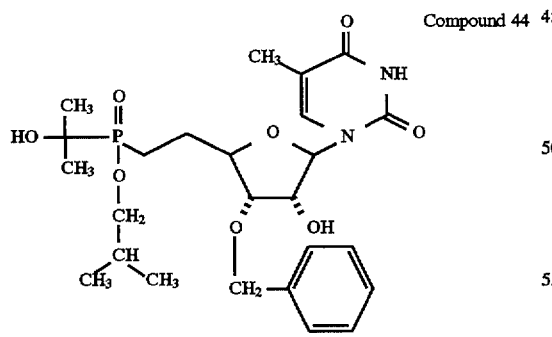

A mixture of Compound 43 (1.80 g, 0.0032M), potassium carbonate (0.438 g, 0.0032M), methanol (8 ml) and water (2 ml) is allowed to stand at room temperature for 15 hours. Evaporation gives a gum which is partitioned between water and ethyl acetate (10 ml). Extraction with ethyl acetate (3×10 ml) followed by a brine wash, drying (MgSO$_4$) and evaporation gives Compound 44 as a white solid.

$^{31}$P nmr (CDCl$_3$, 162 MHz) δ=56.3, 56.4 ppm.

EXAMPLE 45

This example describes the preparation of

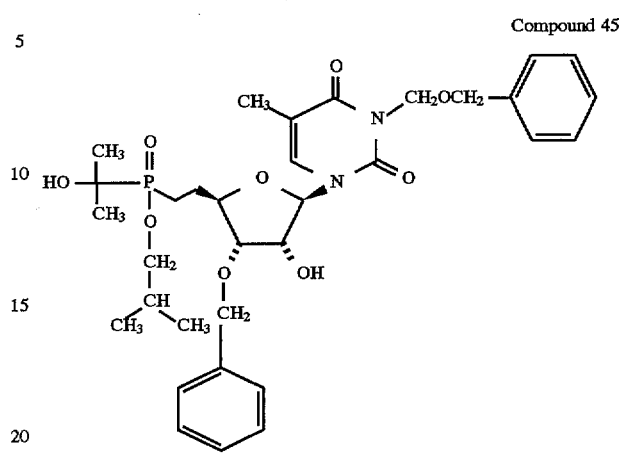

Compound 44 (16.79 g., 32 mmole) is dissolved in dichloromethane (100 ml) and the mixture is cooled to 5° C. 1,8-Diazabicyclo[5.4.0]undec-7-ene (DBU) (10.72 g., 70.4 mmole) is added followed by phenylmethoxychloromethane (6.02 g., 38.4 mmole). The reaction mixture is allowed to warm to room temperature and stirred for three hours. Further phenylmethoxychloromethane (0.6 g, 3.8 mmole) is added and the mixture left overnight. Dilute hydrochloric acid (100 ml) is added and the organic phase separated off and washed with water then brine and dried (Mg80$_4$). Evaporation of the solvent gives an oil which is purified by dry flash silica chromatography using 2% methanol in dichloromethane as eluant to give Compound 45.

$^{31}$P nmr (CDCl$_3$, 162 MHz) δ 55.87 ppm.

EXAMPLE 46

This describes the preparation of

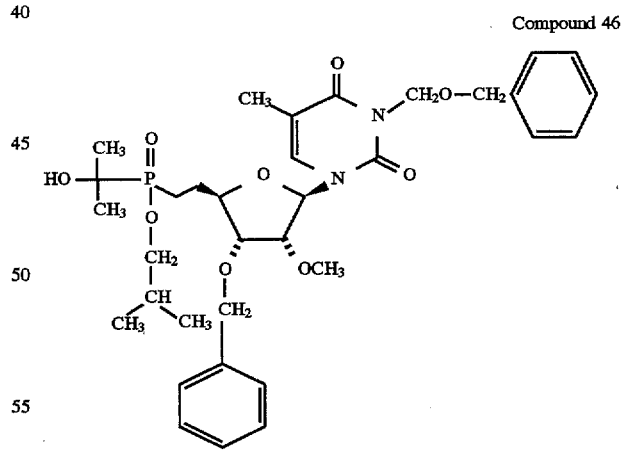

Compound 45 (5.6 g, 8.7 mmole, and iodiomethane (2.47 g, 8.7 mmole) are stirred in acetonitrile (50 ml) and the solution is cooled to 5° C. 2-tert-Butylimino-2-diethylamino-1,3-dimethylperhydro 1,3,2-diazaphosphorin-BDDDP., ex Fluka (2.38 g., 8.7 mmole) is added and the mixture stirred for 5 hours. More iodomethane (1.2 g) and BDDDP (1.2 g) are added in portions over 24 hours. The solvent is removed by evaporation and the residue dissolved in ethyl acetate and washed successively with water, dilute HCl, aqueous NaHCO$_3$ and brine. The solvent is removed and the residue is purified by flash chromatography using 10% methanol in chloroform eluant on silica, and then silica chromatography using 1.2% methanol in chloroform as eluant. There is obtained Compound 46.

$^{31}$P nmr (CDCl$_3$ 162 MHz) δ 55.78 ppm.

EXAMPLE 47

This example describes the preparation of

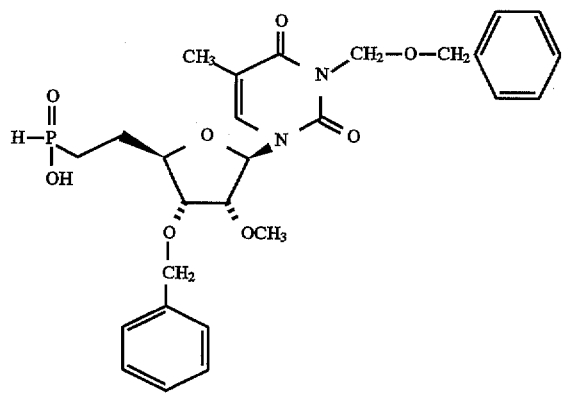

Compound 47

A solution of Compound 46 (1.3 g., 1.97 mmole) in methanol (10 ml) and aqueous ammonia (50%, 25 ml) is heated at 80° C. for 8 hours. The resulting solution is evaporated and the residual oil dissolved in water (10 ml). Dowex (50 W×2) ion exchange resin is added until the solution becomes acidic. The Dowex is filtered off and the aqueous solution evaporated to dryness to give Compound 47.

$^{31}$P nmr (CD$_3$OD., 162 MHz) δ 35.89 ppm., J$_{PH}$ 540 Hz

EXAMPLE 48

This example describes the preparation of

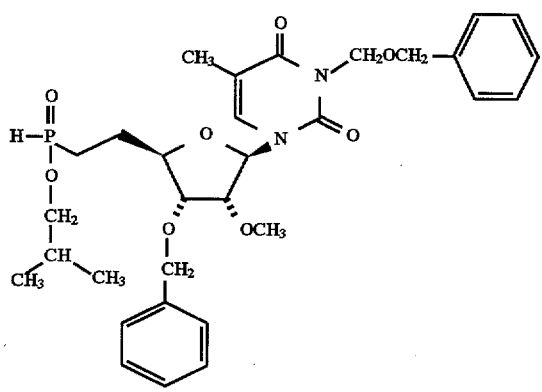

Compound 48

Compound 47 (0.45 g., 0.83 mmole) is dissolved in tetrahydrofuran (5 ml.) and 2-methylpropan-1-ol (0.07 g., 0.99 mmole), dimethylaminopyridine (50 mg.), and dicyclohexylcarbodiimide (0.205 g., 0.99 mmole ) are added. The mixture is stirred for three hours. Ether (15 ml.) and hexane (5 ml.) are added. The dicylohexylurea formed is filtered off and the solvent is evaporated. The residual oil is purified by chromatography on silica using 2% methanol in ethyl acetate as eluant, to give Compound 48.

$^{31}$P nmr. (CDCl$_3$ 162 MHz) δ, 38.29 and 38.75 ppm, J$_{PH}$=540 Hz

EXAMPLE 49

This example describes the preparation of

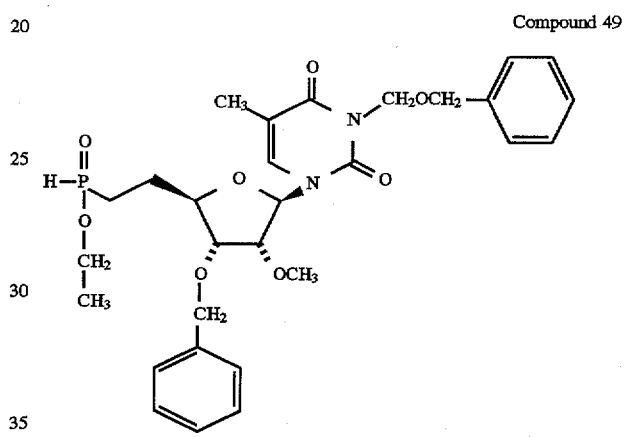

Compound 49

Compound 47, (0.9 g, 1.65 mmole) is dissolved in tetrahydrofuran (10 ml.) and ethanol (0.076 g., 1.65 mmole), Dimethylaminopyrine (10 mg.), and dicyclohexylcarbodiimide (0.409 g., 1.98 mmole) are added and the mixture is stirred for three hours. Ether (30 ml.) and hexane (5 ml.) are added and the dicyclohexyl urea formed is filtered off. Evaporation of the solvent gives Compound 49, which is used in the preparation of Compound 50 without further purification.

$^{31}$P nmr(CDCl$_3$, 162 MHz) δ 37.65, 38.09 ppm, J$_{PH}$=535 Hz

EXAMPLE 50

This example describes the preparation of

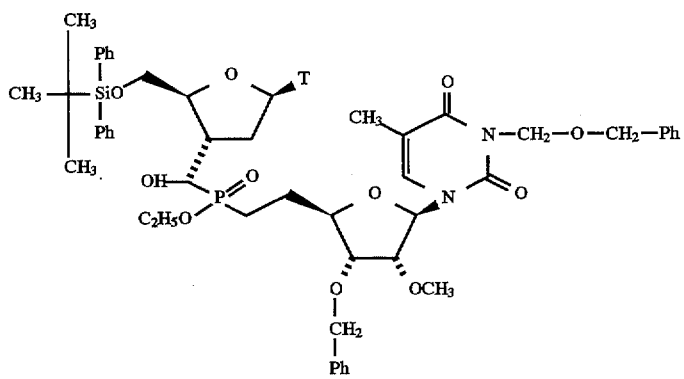

Compound 50 where Ph is phenyl and T is 1-thyminyl.

To a solution of Compound 49 (4.9 g., 8.56 mmole) and an aldehyde of formula IV where $B^1$ is I-thyminyl, $R^5$ is hydrogen and $R^6$ is tert-butyldiphenylsilyl (4.22 g., 8.56 mmole) in dry THF (50 ml.) under argon at room temperature is added 1,8-diazabicyclo[5.4.0]undec-7-ene. (DBU., 1.30 g., 8.56 mmole). The solution is stirred for four hours and flash-chromatographed on silica using 10–20% ethanol in chloroform as eluant. Further purification is achieved with chromatography on silica using 2–5% ethanol in chloroform as eluant. There is obtained Compound 50 as a mixture of four diastereoisomers.

$^{31}P$ nmr (CDCl$_3$, 162 MHz) δ 54.23, 53.24, 52.34, and 52.10 ppm.

EXAMPLE 51

This example describes the preparation of

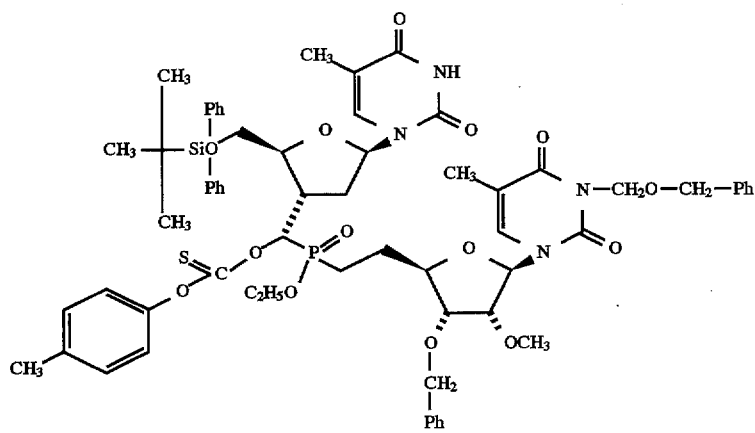

Compound 51 where Ph is phenyl.

Compound 50 (4.7 g., 4.41 mmole), triethylamine (1.62 ml, 13.2 mmole) and dimethylaminopyridine (0.54 g., 4.4 mmole) are dissolved in dichloromethane (50 ml).

The solution is cooled to 5° C. p-Tolylchlorothionoformate (1.54 g., 8.2 mmole) is added and the mixture stirred for 8 hours, allowed to warm to room temperature and allowed to stand for 48 hours. The solvent is removed and the residue purified firstly by flash chromatography on silica using dichloromethane—10% ethanol/dichloromethane gradient and then chromatography on silica using 2–4% ethanol/dichloromethane as eluant. There is obtained Compound 51 as a mixture of four diastereoisomers.

$^{31}$P nmr. (CDCl$_3$, 162 MHz) δ 47.85, 48.12, 48.20, 48.32 ppm.

EXAMPLE 52

This example describes the preparation of

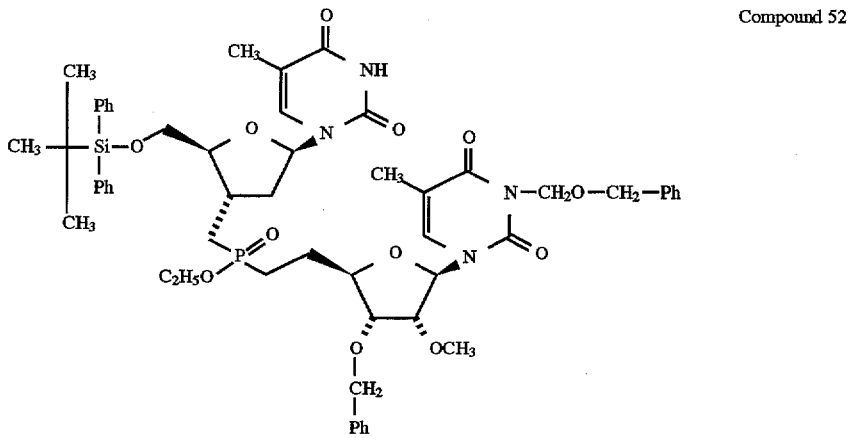

Compound 52 where Ph is phenyl.

Compound 51 (3.25 g., 2.67 mmole), tributyltinhydride (1.12 g., 3.85 mmole) and azobis (isobutyronitrile) (0.054 g., 3.3 mmole) are heated to 100° in degassed toluene (25 ml) under argon for 6 hours. The solvent is removed and the residue is dissolved in acetobitrile and washed with hexane (3×25 ml). Evaporation of the acetonitrile gives a white foamy solid, which is purified by chromatography on silica, using 2–5% ethanol in dichloromethane as eluant. There is obtained Compound 52 successively from the column as a single isomer A, a mixture of isomers B and the other isomer C.

$^{31}$Pnmr (CDCl$_3$, 162 MHz).
A δ=53.87 ppm
B δ=54.14 and 53.87 ppm
C δ=54.10 ppm

EXAMPLE 53

This example describes the preparation of

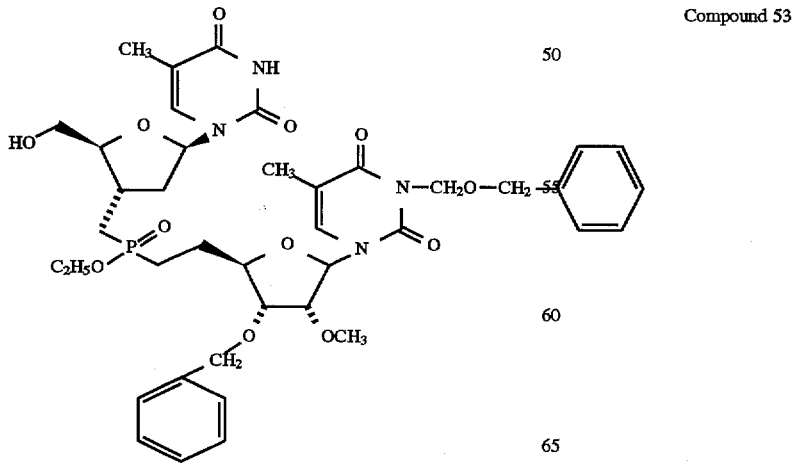

Compound 53

Compound 52 (single isomer A, 0.57 g., 0.54 mmole) is mixed with tetra n-butylammonium fluoride (1.0 m. THF, 0.53 μl.) and acetic acid (0.033 g) in tetrahyctrofuran. The mixture is allowed to stand overnight, then evaporated to a gum which is purified by chromatography on silica using 4–7.5% ethanol in chloroform as eluant. There is obtained Compound 53 as a single isomer.

³¹P nmr (CDCl₃, 162 MHz.) δ=55.86 ppm.

When the reaction is repeated on Compound 52 (mixed isomers, B) it gives the mixed isomers of Compound 53. ³¹Pnmr δ=55.78 and 56.14 ppm.

EXAMPLE 54

This example describes the preparation of

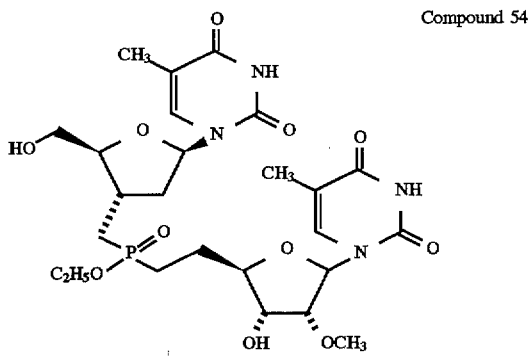

Compound 54

Compound 53 (0.66 g., 0.81 mmole) is hydrogenated in ethanol (10 ml.) using 5% palladium on carbon as catalyst. The reaction is complete in 72 hours at room temperature.

The catalyst is filtered off and the solvent removed to give a white solid. This solid is dissolved in ethanol (5 ml) and sodium ethoxide solution (1 ml. 0.1%) is added and the mixture stood at room temperature for 2 hours. The solvent is removed and ethanol (2×10 ml.) is added, evaporating the solvent after each addition. The residue is dissolved in ethanol (10 ml.) and Dowex (50 W×2) ion exchange resin is added until neutral. The Dowex is filtered off and the solvent removed to give Compound 54 as a mixture of isomers.

³¹P nmr (CDCl₃, 162 MHz) δ 62.09, 62.16 ppm.

EXAMPLE 55

This example describes the preparation of

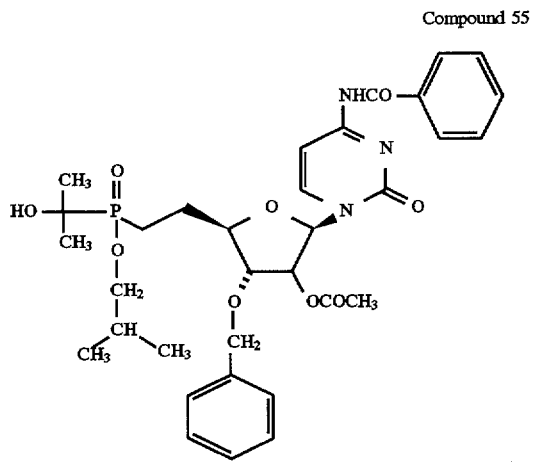

Compound 55

N-Benzoylcytosine (3.4 g., 15.88 mmole) N,O-bis trimethylsilylacetamide (9.69 g., 47.65 mmole) and dichloroethane (40 ml) are stirred at 50° C. for 1 hour. The resulting clear solution is cooled to room temperature and Compound 42 (7.95 g., 15.88 mmole) in dichloroethane (40 ml.) is added, followed by trimethylsilytrifluoromethane sulphonate (10.6 g., 47.65 mmole). The mixture is stirred at 50° C. for 4 hours, then cooled and poured onto ice-cold saturated aqueous sodium bicarbonate maintaining pH above 7. The organic phase is separated, washed with brine and dried. On evaporation of the solvent, a yellow foamy solid is obtained. This is dissolved in acetic acid (60 ml.), THF (20 ml.) and water (20 ml.). The solution is heated to 50° C. for four hours. The resulting mixture is evaporated to half the volume and then co-evaporated with methanol and water mixtures twice. There is obtained Compound 55 as a white solid, which is further purified by chromatography on silica using 10% methanol in chloroform as eluant.

³¹Pmnr. (CDCl₃, 162 MHz) δ 54.7, 54.8 ppm.

EXAMPLE 56

This example describes the preparation of

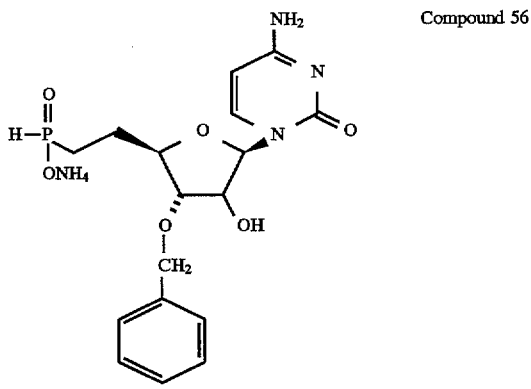

Compound 56

Compound 55 (2.0 g., 3.0 mmole), sodium methoxide (0.65 g., 25% solution in methanol) and methanol (20 ml) are mixed. The mixture is left at room temperature overnight under argon. Dowex 50 W×8 H⁺ form ion exchange resin is added until the solution is acidic. The Dowex is filtered off and the filtrate washed with methanol and water, then eluted with aqueous ammonia (1%). Evaporation of the eluant gives Compound 56.

³¹P nmr (CD₃OD, 162 MHz) δ 27.5 ppm. J$_{PH}$=500 Hz.

EXAMPLE 57

This example describes the preparation of

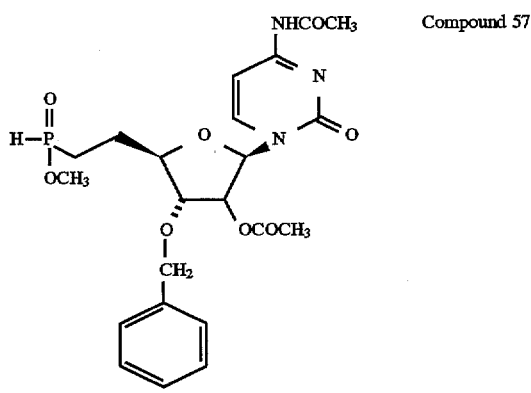

Compound 57

Compound 56 (0.08 g.), acetic anhydride (2 ml.), pyridine (2 ml.) and tetrahydrofuran (5 ml) are heated at 50° C. for 3 hours. The mixture is evaporated and co-evaporated with methanol (3×10 ml.).The residue is purified by silica chromatography using 5% methanol in chloroform as eluant. There is obtained Compound 57 as a colourless oil.

$^{31}$Pnmr (CDCl$_3$, 160 MHz) δ=40.84., 41.16 ppm. $J_{PH}$=540 Hz

EXAMPLE 58

This example describes the preparation of

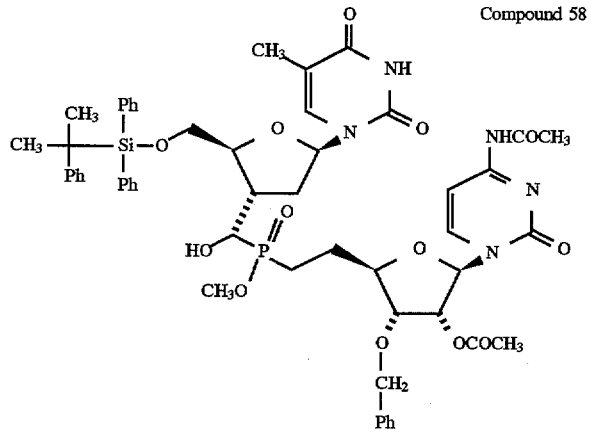

Compound 58 where Ph is phenyl.

Compound 57 (0.09 g.) is added to an aldehyde of formula IV (0.09 g.) where B$^1$ is thyminyl, R$^5$ is hydrogen and R$^6$ is tert-butyl diphenylsilyl in dry THF (5 ml) under argon. 1,8-Diazabicyclo [5.4.0]undec-7-ene (D.B.U., 0.03 g) is added and the mixture is stirred for 3 hours. Removal of the solvent gives an oil which is passed quickly down a dry column of silica using 1% methanol in chloroform. There is obtained Compound 58 as a mixture of diastereoisomers.

$^{31}$P nmr (CDCl$_3$, 162 MHz) δ=56.47, 56.51, 56.58 and 56.88 ppm.

EXAMPLE 59

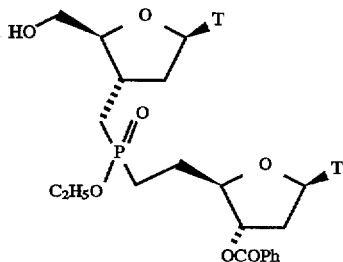

Compound 59 where Ph is phenyl and T is 1-thyminyl.

Following the procedure of Example 15, but replacing Compound 13 by the first diastereomer obtained in Example 13, Compound 59 is obtained as a single diastereoisomer.

$^{31}$Pnmr $^1$H decoupled (CDCl$_3$, 162 MHz) δ 55.95 ppm.

EXAMPLE 60

This example describes the preparation of

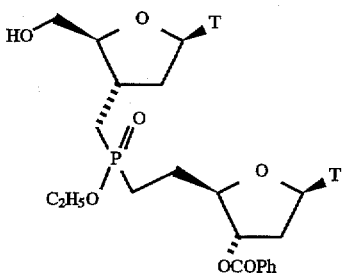

Compound 60 where Ph is phenyl and T is l-thyminyl.

Following the procedure for Example 15, but replacing Compound 13 by the second diastereoisomer obtained in Example 13, Compound 60 is obtained as a single diastereoisomer.

$^{31}$Pnmr $^1$H decoupled (CDCl$_3$, 162 MHz) δ 55.2 ppm.

EXAMPLE 61

This example describes the preparation of

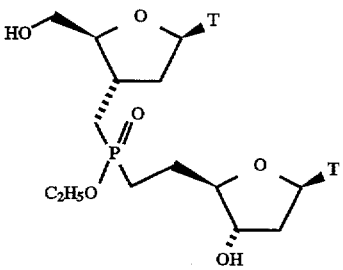

Compound 61 where T is 1-thyminyl.

To a solution of Compound 59 (1.20 g., 1.78 mmol) in dry methanol (20 ml) is added sodium (81 mg. 3.6 mmol) and the resulting solution stirred at room temperature for 1 hour. Acetic acid (2031 μl, 3.6 mmol) is then added and the resulting mixture concentrated and purified by flash silica column chromatography (chant chloroform/ethanol gradient elution 4:1–3:1). Compound 61 is obtained as a single diastereoisomer.

$^{31}$P nmr $^1$H decoupled (162 MHz, CD$_3$OD), δ 63.3 ppm.

EXAMPLE 62

This example describes the preparation of

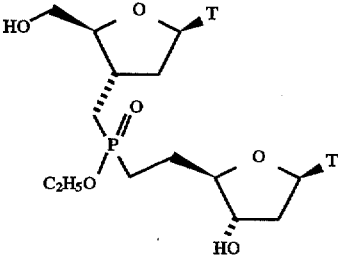

Compound 62 where T is l-thyminyl.

Following the procedure of Example 61, but replacing Compound 59 by Compound 60, there is obtained Compound 62 as a single diastereoisomer.

$^{31}$Pnmr $^1$H decoupled (162 MHz, CD$_3$OD) δ 59.7 ppm.

EXAMPLE 63

This describes the preparation of

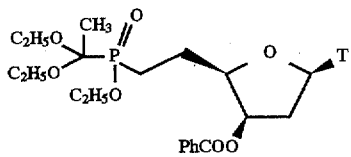
Compound 63 where Ph is phenyl and T is 1-thyminyl.

To a solution of Compound 1 (6.08 g, 13.6 mmol) in dry pyridine (50 ml) is added benzoyl chloride (1.89 ml, 16.3 mmol). After standing at room temperature under argon for 48 hours, concentration gives a yellow oil. Dissolution in dichloromethane (200 ml), washing with 0.5N HCl (2×50 ml) and saturated $NaHCO_3$ (2×50 ml) and drying over $Na_2SO_4$ gives a yellow foam which is purified by repeated flash silica column chromatography to give Compound 63 as a white solid.

$^{31}P$ nmr $^1H$ decoupled ($CDCl_3$), 162 MHz) δ 48.3 and 48.2 ppm m/z (CI,$NH_3$) 553.3($MH^+$) 507.3($M^+$—$OC_2H_5$).

EXAMPLE 64

This describes the preparation of

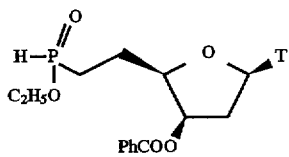
Compound 64 where Ph is phenyl and T is 1-thyminyl.

Trimethylsilylchloride (1.6 ml, 13 mmole) is added to a stirred solution of Compound 63 (700 mg, 1.3 mmole) in chloroform (10 ml) containing ethanol (0.2 ml) under argon. The resulting solution is stood at room temperature for 20 hours and is then concentrated under vacuum. Purification by flash silica column chromatography (eluant:chloroform/ethanol 20:1) gives Compound 64 as a white foam isolated as a mixture of 2 diastereoisomers.

Found C 52.4, H5.4, N 6.2, P 6.3%

$C_{20}H_{25}N_2O_7P.¼CHCl_3$ requires $C_{52.15}$, H5.45, $N_{6.0}$, P6.65%.

m/z (CI $NH_3$) 454($MNH_4^+$) 437($MH^+$)

EXAMPLE 65

This describes the preparation of

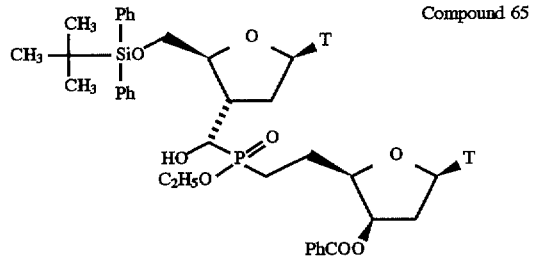
Compound 65 where Ph is phenyl and T is 1-thyminyl.

To a solution of Compound 64 (393 mg, 0.9 mmole) and an aldehyde of Formula IV where $R^6$ is tert-butyldiphenylsilyl, $R^5_a$ is a hydrogen and $B^1$ is 1-thyminyl (433 mg, 0.87 mmole) in dry THF (10 ml) under an atmosphere of argon is added diazabicyclo[5.4.0]undec-7-ene (0.13 ml, 0.88 mmole) at 0°–5° C. The resulting mixture is stirred at room temperature for 2 hours and concentrated. Passage through a 2 cm thick flit of silica with a 5:1 mixture of chloroform and ethanol (400 ml) gives, after concentration, an off-white solid. Further purification by flash silica chromatography (gradient elution, chloroform:ethanol 25:1–13:1) gives Compound 65 as a white solid, isolated as a mixture of four diastereoisomers.

Found C 58.7, H5.7, $N_{5.6}$, P3.0%

$C_{47}H_{57}N_4O_{12}PSi.⅓CHCl_3$ requires C 58.7, H 5.95, N 5.8, P 3.2%.

$^{31}$Pnmr $^1H$ decoupled ($CDCl_3$, 162 MHz) δ 53.9, 53.8, 53.6 and 53.1 ppm. m/z ($FAB^+$) 929 ($MH^+$), 803, (M-T).

EXAMPLE 66

This example describes the preparation of

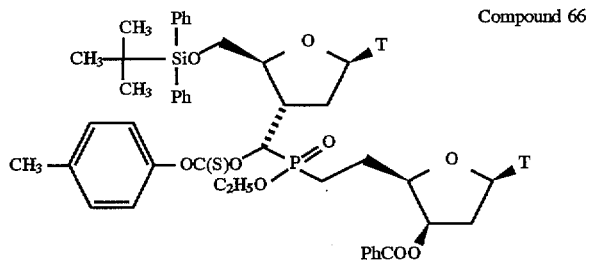
Compound 66 where Ph is phenyl and T is 1-thyminyl.

To a solution of Compound 65 (0.50 g, 0.54 mmol) and dimethylaminopyridine (65 mg, 0.53 mmol) in dry dichloromethane (15 ml) is added triethylamine (97 µl, 0.7 mmol) under argon. The resulting solution is cooled to 0°–5° C. and p-tolylchlorothiononformate (117 µl, 0.76 mmol) is added dropwise over 5 minutes. After standing at room temperature for 18 hours, the reaction mixture is diluted (50 ml $CH_2Cl_2$) and washed with 0.1N $NaH_2PO_4$ (2×25 ml). Drying ($MgSO_4$), concentration and purification by flash silica column chromatography (eluant:Chloroform-ethanol, 25:1) gives Compound 66 as a white solid isolated as a mixture of 4 diastereoisomers.

Found C 58.4, H 5.7, N 4.8, P 2.5%.

$C_{55}H_{63}N_4O_{13}PSSi.3H_2O$ requires C58.3, H6.15, N 4.95, P 2.75%.

$^{31}P$ nmr. $^1H$ decoupled ($CDCl_3$, 162 MHz) δ 47.7, 47.4, 46.7 ppm.

EXAMPLE 67

This describes the preparation of

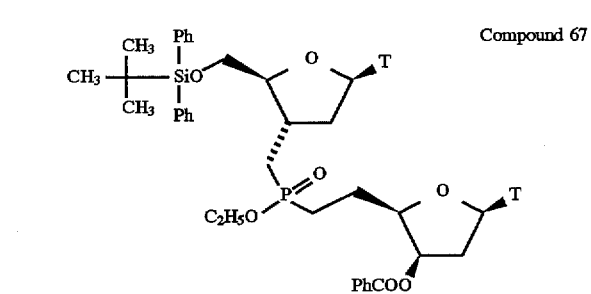
Compound 67 where Ph is phenyl and T is 1-thyminyl.

To a solution of Compound 66 (365 mg, 0.34 mmol), and tributyltinhydride (109 µl, 0.41 mmol) in degassed toluene (3 ml) under argon at 100° C. is added azobisisobutyronitrile (AIBN) (3 mg). After 3 hours at 100° C., concentration gives an off white foam which is purified by flash silica column chromatography (gradient elution, chloroform:ethanol 30:1–25:1) to give Compound 67 as a mixture of 2 diastereoisomers.

Found C60.0, H6.3, $N_{5.9}$% $C_{47}H_{57}N_4O_{11}$ PSi. ¼ $CHCl_3$ requires C 60.2, H 6.1, $N_{5.95}$%.

$^{31}$P nmr $^1$H decoupled ($CDCl_3$, 162 MHz) δ 54.3, 53.6 ppm.

m/z ($FAB^+$) 913 ($MH^+$), 787 (M-T).

EXAMPLE 68

This describes the preparation of

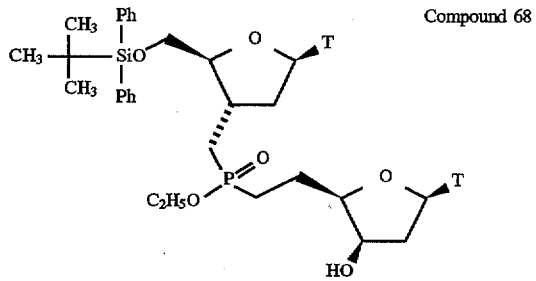

Compound 68 where Ph is phenyl and T is 1-thyminyl.

To a solution of Compound 67 (100 mg. 0.11 mmole) in dry methanol (2 ml) under argon is added sodium (5 mg). After stirring for 1 hour at room temperature acetic acid (35 μl) is added. Concentration gives a white solid which is purified by flash silica column chromatography (eluant, chloroform:ethanol, 15:1) to give Compound 68 as a white solid, isolated as a mixture of 2 diastereoisomers.

$^{31}$P nmr $^1$H decoupled ($CDCl_3$, 162 MHz) δ 56.1, 55.6 ppm.

m/z ($FAB^+$) 809 ($MH^+$) 683 (M-T).

EXAMPLE 69

This describes the preparation of

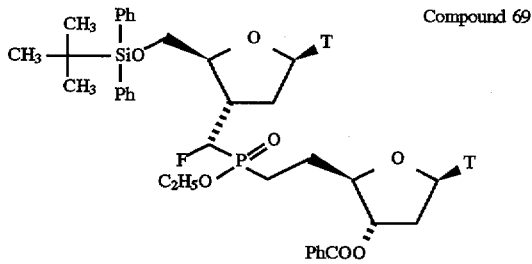

Compound 69 where Ph is phenyl and T is 1-thyminyl.

To a solution of Compound 11 (a mixture of 4 diastereoisomers, 4.0 g, 4.3 mmol) in dry chloroform (70 ml) is added diethylaminosulphurtrifluoride (1.13 ml, 8.6 mmol) at 0° C. under an atmosphere of argon. After one hour, triethylamine (1.2 ml, 8.6 mmol) is added. The resulting mixture is transferred to a separating funnel with chloroform (100 ml) and washed with saturated aqueous $NaHCO_3$ (2×30 ml). Drying ($MgSO_4$), concentration and purification by flash silica column chromatography (gradient elution, chloroform-ethanol 35:1–25:1) gives Compound 69 as a white foam containing a mixture of diastereomeric products.

Found C.56.8%, H 5.9%, F 1.7%, N 5.5%,P 2.8%; $C_{47}H_{56}FN_4O^{11}PSi$. ⅔$CHCl_3$ requires C 56.65%, H 5.65%, F 1.9%, N 5.55%, P3.05%

$^{31}$P nmr $^1$H decoupled ($CDCl_3$, 162 MHz), δ 47.75 (d, $J_{P-F}$ 67.4 Hz), 47.7 (d, $J_{P-F}$ 76.8 Hz), 47.2 (d, $J_{P-F}$ 69.3 Hz), 47.15 (d, $J_{P-F}$67.1 Hz) ppm.

m/z ($FAB^+$) 931 ($MH^+$).

Purification of this product mixture also allows the separation of the first eluted diastereoisomer in a pure form: Compound 69A.

$^{31}$Pnmr $^1$H decoupled ($CDCl_3$, 162 MHz) δ 47.35 (d, $J_{P-F}$ 64.4 Hz).

EXAMPLE 70

This describes the preparation of

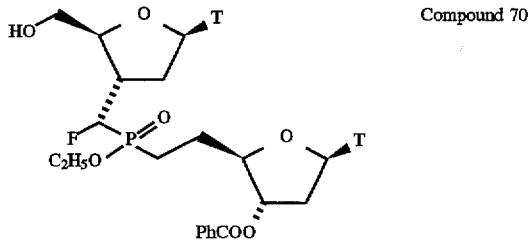

Compound 70 where Ph is phenyl and T is 1-thyminyl.

To a solution of Compound 69 (100 mg, 0.107 mmol) in THF (2 ml) containing acetic acid (6.2 μl, 0.1 mmol) is added a 1.0 molar solution of tetra-n-butylammonium flouride in THF (107 μl, (0.107 mmol). The resulting solution is stirred at room temperature for 3 hours and concentrated. Purification by flash silica column chromatography (gradient elution, chloroform-ethanol 20:1–15:1) gives Compound 70 as a white foam after concentration-isolated as a mixture of 4 diastereoisomers.

Found C:48.5%, H.5.1%, N 7.0%, $C_{31}H_{38}FN_4O_{11}P$. ¾ $CHCl_3$ requires C.48.75%, H. 5.0%, N. 7.15%.

$^{31}$Pnmr $^1$H decoupled ($CDCl_3$, 162 MHz) δ 49.1 (d, $J_{P-F}$ 74.7 Hz), 48.2 (d, $J_{P-F}$ 77.9 Hz) 47.9 (d, $J_{P-F}$ 62.9 Hz), 47.6, (d, $J_{P-F}$ 65.8 Hz) ppm m/z ($FAB^+$). 715 ($MNa^+$), 693($MH^+$).

EXAMPLE 71

This describes the preparation of

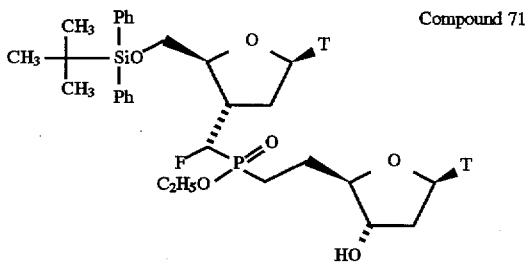

Compound 71 where Ph is phenyl and T is 1-thyminyl.

To a solution of Compound 69 (100 mg, 0.107 mmol) in dry methanol (2 ml) under an atmosphere of argon is added sodium (8 mg, 0.35 mmol). The resulting solution is stirred at room temperature for 2 hours. Acetic acid (60 μl 1.0 mmol) is added and the mixture concentrated under vacuum. Purification by flash silica column chromatography (eluant chloroform-ethanol 15:1) gives Compound 71 as a mixture of 4 diastereoisomers.

Found: C 54.0%, H. 5.8%, F. 2.0%, N. 6.1%, P.3.0%; $C_{40}H_{52}FN_4O_{10}PSi$. ⅔ $CHCl_3$ requires C 53.9%, H. 5.85%, F 2.1%, N 6.2%, P. 3.4%

$^{31}$Pnmr $^1$H decoupled ($CDCl_3$, 162 MHz),δ 49.2 (d, $J_{P-F}$ 67.8 Hz), 48.35 (d, $J_{P-F}$ 76.8 Hz) 48.3 (d, $J_{P-F}$ 64.0 Hz), 48.25 (d, $J_{P-F}$ 77.3 Hz) ppm.

EXAMPLE 72

This describes the preparation of

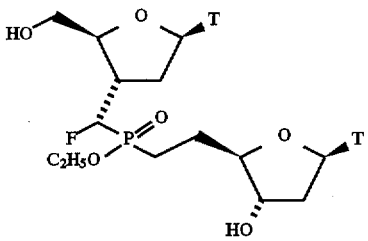

Compound 72 where T is 1-thyminyl.

Method 1

To a solution of Compound 70 (375 mg, 0.54 mmol) in dry ethanol (40 ml) under an argon atmosphere is added sodium (50 mg, 2.2 mmol). The resulting suspension is stirred at room temperature for 4 hours before the addition of acetic acid (0.5 ml). Concentration and purification by flash silica column chromatography (gradient elution:chloroform-ethanol 8:1–4:1) gives Compound 72 as a white foam and a mixture of 4 diastereoisomers.

$^{31}$P nmr $^1$H decoupled (CD$_3$OD, 162 MHz) δ 50.7 (d, $J_{P-F}$ 80.9 Hz), 50.6 (d, $J_{P-F}$ 67.1 Hz) 50.4 (d, $J_{P-F}$ 68.7 Hz), 50.2 (d, $J_{P-F}$ 57.0 Hz) ppm.

Method 2

To a solution of Compound 71 (65 mg, 0.079 mmol) in THF (2 ml) containing acetic acid (4.5 µl, 0.079 mmol) is added a 1 molar solution of tetrabutylammonium flouride in THF (78 µl, 0.078 mmol). After 3 hours the solution is concentrated in vacu and triturated with diethylether (2×10 ml). The remaining crude solid is purified by flash silica column chromatography (eluant:chloroform-ethanol 7:1) to give Compound 72 as a white foam and a mixture of 4 diastereoisomers having the same $^{31}$P NMR spectrum as the product of Method 1.

EXAMPLE 73

This describes the preparation of

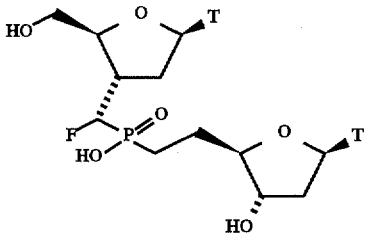

Compound 73 where T is 1-thyminyl.

Method A

To a solution of Compound 72 (18 mg, 30.6 µmol) in deuteromethanol (0.5 ml) containing water (50 µl) is added sodium hydroxide (10 mg). After standing at room temperature for 18 hours, Compound 72 is fully converted into Compound 73, which is present as two diastereoisomers.

$^{31}$P nmr $^1$H decoupled (CD$_3$OD, 162 MHz) δ 34.2 (d, $J_{P-F}$ 67 Hz), 33.9 (d, $J_{P-F}$ 64.1 Hz)

Method B

Compound 72 is dissolved in concentrated aqueous ammonia solution and heated at 70° C. After 7 hours the mixture is concentrated and passed through a short column of silica with 3:1 chloroform/ethanol and then ethanol; reconcentrated and further purified by passage through Amberlite (basic) with a 1:1 acetic acid/water mixture. Freeze drying gives the product as a white meringue which is present as a mixture of two diastereoisomers having the same $^{31}$P nmr spectrum as the product of Method A.

Found C 47.3%, H 5.7%, F 3.1%, N 9.8%, P 5.1%, C$_{22}$H$_{30}$FN$_4$O$_{10}$P requires C 47.15%, H 5.4%, F 3.4%, N 10.0%, P 5.5%.

m/z (FAB$^+$) 599 (MK$^+$), 583 (MNa$^+$), 561 (MH$^+$).

EXAMPLE 74

This describes the preparation of

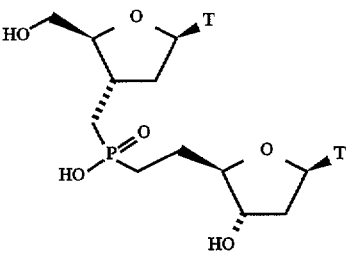

Compound 74 where T is 1-thyminyl.

A solution of Compound 16 (47 mg, 82.4 µmol) in 2N aqueous NaOH is sonicated at 40° C. for 1 hour. Acidic Dowex ion exchange resin is added until the solution remains acidic. Filtration and freeze drying gives the product as a white meringue, isolated as the sodium salt.

Found C 42.8%, H 5.3%, N 9.3%, P 4.9% C$_{22}$H$_{30}$N$_4$O$_{10}$PNa.3H$_2$O requires C42.7, H5.9% N 9.05%, P 5.0%.

$^{31}$P nmr $^1$H decoupled (D$_2$O, 162 MHz) δ 43.0 ppm m/z (FAB$^+$) 543(MH$^+$).

EXAMPLE 75

Purification of Compound 11 by flash silica column chromatography (chloroform/ethanol mixtures) readily gives the first eluting diastereoisomer in a pure form, Compound 75.

$^{31}$P nmr $^1$H decoupled (CDCl$_3$, 162 MHz) δ 53.7 ppm.

EXAMPLE 76

This example describes the preparation of

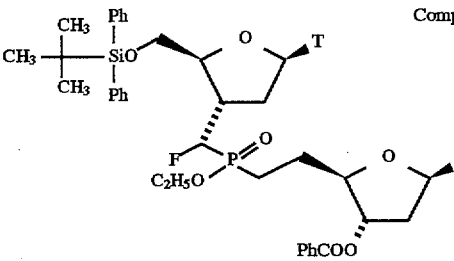

Compound 76 where Ph is phenyl and T is 1-thyminyl.

The procedure of Example 69 is repeated, but using Compound 75 in place of Compound 11. The product, obtained as a single diastereoisomer, is Compound 76.

$^{31}$Pnmr $^1$H decoupled (CDCl$_3$, 162 MHz) δ 47.3 (d, $J_{P-F}$ 79.1 Hz) ppm.

EXAMPLE 77

This describes the preparation of

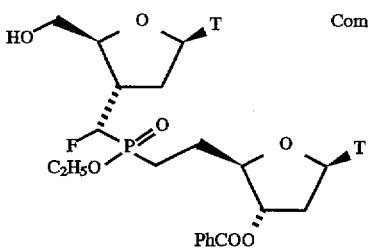

Compounds 77A and 77B where Ph is phenyl and T is 1-thyminyl.

(A) Example 70 is repeated, but using Compound 69A in place of Compound 69. The product, obtained as a single diastereoisomer, is Compound 77A.

$^{31}$Pnmr $^{1}$H decoupled (CDCl$_3$, 162 MHz) δ 48.65 (d, J$_{P-F}$ 64.2 Hz) ppm.

(B) Example 70 is repeated, but replacing Compound 69 by Compound 76. The product, obtained as a single diastereoisomer, is Compound 77B.

$^{31}$Pnmr $^{1}$H decoupled (CDCl$_3$, 162 MHz) δ 48.2 (d, J$_{P-F}$ 78.6 Hz) ppm.

EXAMPLE 78

This describes the preparation of

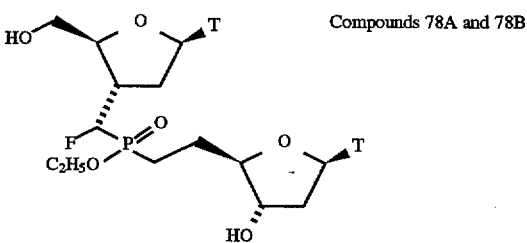

Compounds 78A and 78B where T is 1-thyminyl.

(A) Method 1 of Example 72 is repeated, using Compound 77A in place of Compound 70. The product is Compound 78A, obtained as a mixture of two diastereoisomers at phosphorus.

$^{31}$P nmr $^{1}$H decoupled (CDCl$_3$, 162 MHz) δ 50.6 (d, J$_{P-F}$, 81 Hz) and 50.2 (d, J$_{P-F}$ 55 Hz) ppm.

(B) Method 1 of Example 72 is repeated, using Compound 77B in place of Compound 70. The product is Compound 78B, obtained as a mixture of two diastereoisomers at phosphorus.

$^{31}$P nmr $^{1}$H decoupled (CDCl$_3$, 162 MHz) δ 50.7 (d, J$_{P-F}$ 79.3 Hz) and 50.4 (d, J$_{P-F}$, 68.7 Hz) ppm.

EXAMPLE 79

This describes the preparation of

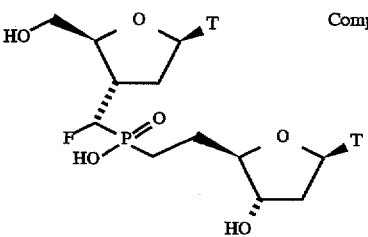

Compounds 79A and 79B where T is 1-thyminyl.

(A) Method A of Example 73 is repeated, using Compound 78A in place of Compound 72. The product is Compound 79A, obtained as a single diastereoisomer.

$^{31}$Pnmr $^{1}$H decoupled (CDCl$_3$, 162 MHz) δ 34.2 (d, J$_{P-F}$ 64.1 Hz) ppm.

(B) Method A of Example 73 is repeated, using Compound 78B in place of Compound 72. The product is Compound 79B, obtained as a single diastereoisomer of opposite chirality to Compound 79A.

$^{31}$Pnmr $^{1}$H decoupled (CDCl$_3$, 162 MHz) δ 34.5 (d, J$_{P-F}$ 67.1 Hz) ppm.

EXAMPLE 80

This describes the preparation of

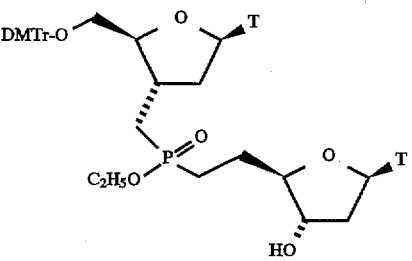

Compounds 80, 80A, and 80B where DMTr is dimethoxytriphenylmethyl and T is 1-thyminyl.

Compound 80A

To a solution of Compound 61 (400 g, 0.7 mmol) in dry pyridine (12 ml) at room temperature under argon atmosphere are added triethylamine (78 mg, 0.77 mmol), dimethylaminopyridine (3.5 mg, 0.028 mmol) and 4$_1$4$^1$-dimethoxytriphenylmethylchloride (225 mg, 0.66 mmol).

After 4 hours at room temperature, a second portion of triethylamine (19 mg, 0.19 mmol), dimethylaminopyridine (1 mg, 0.008 mmol) and dimethoxytriphenylmethylchloride (56 mg, 0.16 mmol) are added. After stirring at room temperature overnight, the reaction mixture is poured into water (15 ml). The aqueous layer is extracted with chloroform (3×20 ml), the combined organic fractions are dried (Na$_2$SO$_4$) and the solvent is removed under vacuum. Flash-chromatography on silica (eluant:CH$_2$Cl$_2$/C$_2$H$_5$OH: 9/1 and 1% triethylamine) gives Compound 80 as a yellow foam.

$^{31}$Pnmr (CDCl$_3$, 101 MHz) δ 54.3 ppm.

$^{1}$H nmr (CDCl$_3$, 250 MHz) δ 3.68 (s 2×OCH$_3$), 6.05–6.15 (m 2, H1') ppm.

Compound 80

The procedure used for the preparation of Compound 80A is repeated, but using Compound 16 (335 mg, 0.59 mmol) is place of Compound 61 and using 104 mg (1.03 mmol) of triethylamine, 4.6 mg (0.038 mmol) of dimethylaminopyridine, 300 mg (0.88 mmol) of dimethoxytriphenylmethyl chloride and 13 ml of pyridine.

The product is Compound 80.

$^{1}$H nmr (CDCl$_3$, 500 MHz) δ 3.79 (s, 2×OCH$_3$), 6.06–6.11 (m, H1'), 6.12–6.14 (m, H1') ppm

FAB-MS: (M+H)$^+$=873.

Compound 80B

The procedure used for the preparation of Compound 80A is repeated, but using Compound 62 (175 mg, 0.31 mmol) in place of Compound 61 and using 54 mg (0.54 mmol) of triethylamine, 3 mg (0.025 mmol) of dimethylaminopyridine, 136 mg (0.40 mmol) of dimethoxytriphenylmethyl chloride and 7 ml of pyridine. The product is Compound 80B.

$^{1}$Hnmr (CDCl$_3$, 250 MHz) δ 3.75 (s, 2×OCH$_3$), 5.95–6.12 (m, H1', H1') ppm.

EXAMPLE 81

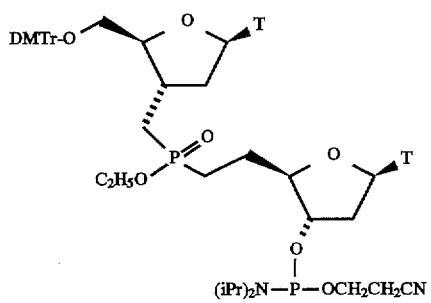

Compounds 81, 81A, 81B where DMTr is dimethoxytriphenylmethyl, iPr is isopropyl and T is 1-thyminyl.

Compound 81A

A solution of Compound 80A (460 mg, 0.527 mmol) in dry dichloromethane (18 ml) is added dropwise at room temperature to a mixture of disopropylammonium tetrazolide (108 mg, 0.63 mmol) and 2-cyanoethyl-N,N,$N^1$,$N^1$-tetraisopropylphosphoro diamidite (174 mg, 0.58 mmol) in dry dichloromethane (10 ml) under an argon atmosphere. The reaction mixture is stirred at 40° C. for 4 hours and after cooling is poured into a saturated aqueous $NaHCO_3$ solution (25 ml). The aqueous layer is extracted with dichloromethane (3×20 ml). The combined organic layers are dried ($Na_2SO_4$) and evaporated. Flash chromatography on silica (eluant:ethyl acetate/methanol: 9/1 and 1% triethylamine) gives an oil. Pure Compound 81 A is obtained by dissolving the residue in dry chloroform, and precipitating with pentane. After coevaporation with benzene, Compound 81A is isolated as a white foam.

$^{31}$P-NMR ($CDCl_3$, 101 MHz) δ 148.55, 148.69, 53.35, 53.75 ppm.

Compound 81

The procedure used for the preparation of Compound 81A is repeated, but using Compound 80 (300 mg, 0.34 mmol) in place of Compound 80A and using 71 mg (0.41 mmol) of diisopropylammonium tetrazolide, 113 mg (0.38 mmol) of cyanoethyl-N,N,$N^1$,$N^1$-tetraisopropylphosphor diamidite and 19 ml of dichloromethane. The product is Compound 81.

$^{31}$Pnmr ($CDCl_3$, 101 MHz) δ 148.57, 148.71, 53.69, 53.29 ppm.

Pd-MS: $(M+K)^+$: 1112.

Compound 81B

The procedure used for the preparation of Compound 81A is repeated, but using Compound 80B (239 mg, 0.27 mmol) in place of Compound 80A and using 56 mg (0.33 mmol) of diisopropylammonium tetrazolide, 91 mg (0.30 mmol) of cyanoethyl-N,N,$N^1$,$N^1$-tetraisopropylphosphor diamidite and 15 ml of dichloromethane. The product is Compound 81B.

$^{31}$Pnmr ($CDCl_3$, 101 MHz) δ 148.61, 148.56, 53.75, 53.35 ppm.

EXAMPLE 82

This describes the preparation of

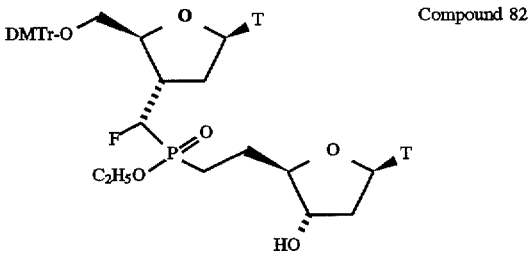

Compound 82 where DMTr and T are as defined in Example 81.

The procedure used for the preparation of Compound 80A in Example 80 is repeated, but using Compound 72 (240 mg, 0.41 mmol) in place of Compound 61, and using 80 mg (0.79 mmol) of triethylamine, 3 mg (0.025 mmol) of dimethylaminopyridine, 228 mg (0.67 mmol) of dimethoxytriphenylmethyl chloride and 10 ml of pyridine. The product is Compound 82.

$^{31}$Pnmr ($CDCl_3$, 101 MHz) δ 47–48 ppm.

EXAMPLE 83

This describes the preparation of

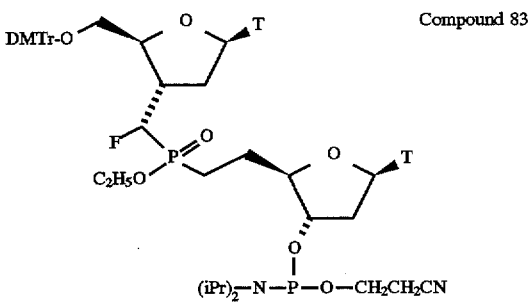

Compound 83 where DMTr, iPr and T are as defined in Example 81.

The procedure used for the preparation of Compound 81A in Example 81 is repeated, but using Compound 82 (365 mg, 0.41 mmol) in place of Compound 80A, using 100 mg (0.58 mmol) of diisopropylammonium tetrazolide, 161 mg (0.53 mmol) of cyanethyl-N,N,$N^1$,$N^1$-tetraisopropylphoshoro diamidite and 12 ml of dichloromethane, and using $CH_2Cl_2$/$CH_3OH$: 20/1 with 1% triethylamine as eluant. The product is Compound 83.

$^{31}$Pnmr ($CDCl_3$, 101 MHz) δ 148.60, 47.2–46.2 ppm
Pd-MS: $(M+Na)^+$: 1115.

EXAMPLE 84

This describes the preparation of

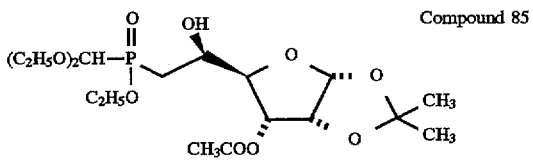

Compound 85

Compound 22 is convened, following the procedure of V. Zsoldos-Mády et al, Monatschifte für Chemie 117, 1325 (1986) into 5,6-anhydro-1,2-O-(1-methylethylidene)α-D-allofuranose-3-O-acetate (Compound 84).

To sodium hydride (60% dispersion in oil, 66 mg, 1.64 mmol), washed free of oil, toluene (8 ml) is added. The suspension is cooled to 0° C., and a solution of ethyl diethoxymethyl phosphinate (321 mg, 1.64 mmol) in toluene (1 ml) is added dropwise over 5 minutes. The mixture is stirred vigorously for 0.5 h at 0° C., allowed to warm to 20° C. and then recooled to 0° C., at which point a solution of Compound 84 (200 mg, 0.82 mmol) in toluene (1 ml) is added dropwise, followed by boron trifluoride etherate (0.30 ml, 2.46 mmol). The solution is warmed to 20° C. and stirred for 3 hours. Saturated aqueous sodium bicarbonate (4 ml) is added to the mixture. The aqueous phase is extracted three times with ether, and the combined ether phase is dried with brine and magnesium sulphate and then evaporated.

The crude product is purified by flash chromatography on silica gel, eluting with a gradient of ethyl acetate/ethanol. The product, a mixture of two diastereoisomers, is obtained as a viscous oil.

$^{31}$Pnmr (162 MHz, CDCl$_3$) δ 44.9, 45.9 ppm m/z (CI,NH$_3$) 441 (MH$^+$). 103 (CH(OEt)$_2$, 100%).

EXAMPLE 85

This describes the preparation of

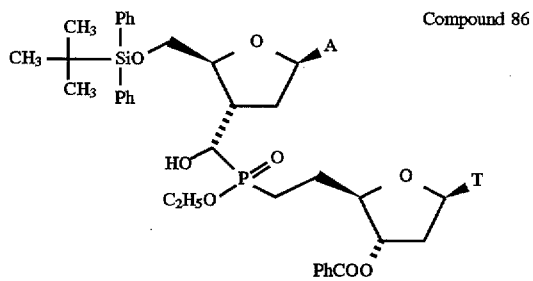

Compound 86 where Ph is phenyl, A is 9-adeninyl and T is 1-thyminyl.

To a solution of Compound 5 (0.12 g, 0.26 mmol) and an aldehyde of formula IV where B$^1$ is 9-adeninyl, R$^5_a$ is hydrogen and R$^6$ is tert-butyldiphenylsilyl (0.10 g, 0.26 mmol, prepared by the method of D. Yu and M. d'Alarcao, J. Org. Chem. 1989, 54, 3240) in dichloromethane (5 ml) at 20° C. is added 1,8-diazabicyclo[5.4.0]undec-7-ene (0.04 ml, 0.26 mmol). The mixture is stirred for 15 hours, at room temperature, concentrated by evaporation and purified by flash silica column chromatography to give Compound 86 as a mixture of diastereoisomers.

EXAMPLE 86

This describes the preparation of

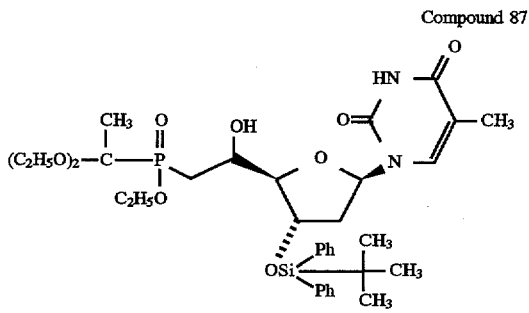

Compound 87 where Ph is phenyl n-Butyl lithium (1.6 m in hexane, 3.9 ml, 6.25 mM) is added dropwise to a solution of ethyl [(methyl) 1,1 diethoxy ethyl]phosphinate (1.4 g, 6.25 mM) in dry THF (20 ml) maintained at −78° C. After 15 minutes a solution of an aldehyde of formula XXXIX where B$^2$ is 1-thyminyl, R$^7$a is tert-butyldiphenylsilyl and R$^8$a is hydrogen, prepared as described in WO92/20822 (1.2 g, 2.5 mM) in THF (5 ml) is added dropwise at −78° C. and the solution is allowed to warm to room temperature.

Saturated aqueous ammonium chloride (50 ml) and ethyl acetate (100 ml) are added. The organic phase is dried (MgSO$_4$) and evaporated to afford a yellow oil. Purification by silica column chromatography, eluting with ethylacetate-hexane (1:1–2:1) mixtures gives Compound 87 as a colourless foam.

$^{31}$P nmr (CDCl$_3$, 16 1 MHz) δ 50.74, 49.76, 49.54, 48.54.

EXAMPLES 87–99

Oligonucleotides are prepared from Compounds 81,81A and 81B and similarly DMTr-protected and phosphoramidite-activated natural nucleosides -2'-deoxyadenosine (dA), -2'-deoxyadcytidine (dC), -2'-deoxyguanosine (dG) and thymidine (dT)—on an ABI 390 automatic DNA synthesiser (available from Applied Biosystems Inc) using standard phosphoramidite chemistry according to Oligonucleotide Sunthesis: A Practical Approach, M. J. Gait, IRL Press, Oxford 1984, but with prolonged coupling times (10 minutes). DMTr oligonucleotides are purified by reverse phase HPLC (eluant A=50 mM triethylammonium acetate (TEAA), pH 7.0; eluant B:50 mM TEAA, pH 7.0 in 70% acetonitrile; elution with gradient from 15% to 45% B in 45 minutes). After purification by HPLC, the DMTr protective group is removed by treatment with 80% aqueous acetic acid and the oligonucleotides are precipitated with ethanol and isolated by centrifugation. The purity of the oligodeoxynucleotides is checked by capillary gel electrophoresis (polyacrylamide; buffer: 100 mM H$_3$PO$_4$, 100 mM Tries, 2 mM ethylenediaminetetracetic acid, 7M urea, pH 8.8).

Part of each of the oligonucleotides derived from Compound 81 prepared as described above is reacted with 2N aqueous NaOH at room temperature to hydrolyse the C$_2$H$_5$O— group on the phosphorus atom in the unit derived from Compound 81 to a hydroxy group. The resulting oligonucleotides are designated as having a modifying unit derived from Compound 81 (hydrolysed) in the tables below.

The prepared oligonucleotide sequences are as follows:

EXAMPLES 87–90

TTT T*TC TCT CTC TCT

T*T indicating the unit derived from the modifying dinucleotide.

| Example | Modifying Dinucleotide |
|---------|------------------------|
| 87      | Compound 81 (hydrolysed) |
| 88      | Compound 81            |
| 89      | Compound 81A           |
| 90      | Compound 81B           |

EXAMPLES 91–94

CTC GTA CCT *TTC CGG TCC

T*T indicating the unit derived from the modifying dinucleotide.

| Example | Modifying Dinucleotide |
|---|---|
| 91 | Compound 81 (hydrolysed) |
| 92 | Compound 81 |
| 93 | Compound 81A |
| 94 | Compound 81B |

EXAMPLES 95–98

CTC GTA CT*T T*TC CGG TCC

T*T indicating the unit derived from the modifying dinucleotide.

| Example | Modifying Dinucleotide |
|---|---|
| 95 | Compound 81 (hydrolysed) |
| 96 | Compound 81 |
| 97 | Compound 81A |
| 98 | Compound 81B |

EXAMPLE 99

GCG T*TT *TT*T T*TT *TGC G

T*T indicating a unit derived from Compound 81 (hydrolysed)

The structure of the oligodeoxynucleotides is checked by matrix assisted laser-desorption time-of-flight (MALDI-TOF) mass spectroscopy; the oligonucleotides being desorbed using 2,4,6-trihydroxyacetophenone as a matrix with diammonium hydrogen citrate as additive (25 mM final concentration) (U. Pieles et at, Nucl. Acids Res. 1993, 21,3191).

The ability of the oligonucleotides to hybridise to their complementary RNA sequences is assessed by recording UV melting curves and determining the melting temperature (Tm) values therefrom. The method is described, for example, by S. M. Freier et al, Biopolymers, 1982,22,1107. The thermal denaturation of the DNA/RNA hybrids is performed at 260 nm using a Gilford Response II Spectrophotometer (available from Ciba-Corning Diagnostics).

Absorption vs temperature profiles are measured at 4 μM of each strand in 10 mM phosphate, 100 mM Na+, 0.1 mM EDTA, pH 7.0. The Tm values are determined from the melting curves obtained. The change in Tm per number of modifying units in the oligonucleotide compared with the corresponding unmodified natural oligonucleotides (ΔTm/mod) is recorded for each oligonucleotide. The results are given below:

| Oligonucleotide | | Tm(°C.) | ΔTm/mod(°C.) |
|---|---|---|---|
| Example | 87 | 45.7 | −2.8 |
| " | 88 | 46.8 | −2.2 |
| " | 89 | 45.7 | −3.3 |
| " | 90 | 47.2 | −1.3 |
| " | 91 | 61.8 | −2.4 |
| " | 92 | 62.6 | −1.6 |
| " | 93 | 62.0 | −2.2 |
| " | 94 | 62.4 | −1.8 |
| " | 95 | 58.2 | −1.6 |
| " | 96 | 58.5 | −1.5 |
| " | 97 | 57.9 | −1.8 |
| " | 98 | 58.8 | −1.3 |
| " | 99 | 39.6 | −1.8 |

EXAMPLE 100

Compounds prepared in some of the previous Examples are tested for antiviral activity against herpes simplex virus type 1 (HSV-1) (strain 17i) and human cytomegalovirus (HCMV) (strain AD 169) in vitro. Aqueous solutions of the compounds are prepared at concentrations between 10 mM and 50 mM. The solutions are stored at −70° C. after preparation and thawed prior to use in the antiviral assays. After thawing, the solutions are diluted to the appropriate concentration in the cell-culture medium without prior filtration.

In a procedure similar to that described by Tyms et al, J. Antimicrob. Chemother., 8, 65–72 (1981), cell monolayers are infected with 20–200 plaque forming units and after virus adsorption the inoculum is replaced by maintenance medium containing different concentrations of the compound under investigation. Virus spread is prevented by the incorporation of 0.5% low gelling temperature agarose. At the end of a set period (2 or 3 days for HSV and 7 to 10 days for HCMV) monolayers are fixed, stained with methylene blue and plaque numbers determined.

The results of the plaque-reduction assay for different dinucleotide analogues of the invention are given below.

| | | IC 50 | | |
|---|---|---|---|---|
| Virus | Cells | Compound 13 | Compound 14 | Compound 15 |
| HCMV | Human embryonic fibroblasts | >1<10 μM | >200 μM | >2 μM |
| HSV-1 | Vero | >5<50 μM | >20<200 μM | >5 μM |

What is claimed is:

1. An oligonucleotide of Formula $$5'\text{-U-(O-L-O-V)}_n\text{O-L-O-W-3'} \qquad \text{XXXXI}$$

where U,V, and W are selected from the group consisting of a natural or a synthetic nucleoside, nucleotide or oligonucleotide at least one of the residues U,V, and W being a dinucleotide residue having the formula

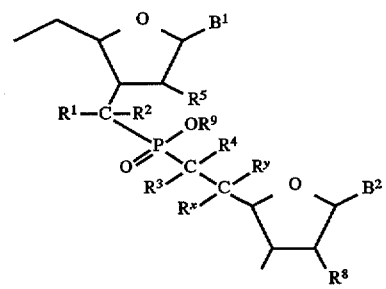

XXXXII where L is a nucleoside bridging group, n is a number from 0 to 200 and $B^1$ and $B^2$ are each independently a monovalent nucleoside base radical;

$R^1$ is $R^1_a$ or Z;

$R^1_a$, $R^2$, $R^3$ and $R^4$ are each independently hydrogen, halogen or hydroxy;

$R^5$ is $R^5_a$ or Z;

$R^8$ is $R^8_a$ or Z;

$R^5_a$ and $R^8_a$ are each independently hydrogen, halogen, hydroxy, —$OR^{10}$, —$OCOR^{10}$ or silyloxy substituted by three $C_1$–$C_{15}$ hydrocarbyl groups;

$R^9$ is hydrogen, a $C_1$–$C_8$ aliphatic radical, a $C_3$–$C_8$ cycloaliphatic radical, a $C_6$–$C_{15}$ aromatic radical, a $C_7$–$C_{13}$ araliphatic radical, an alkali metal ion or an ammonium ion;

$R_{10}$ is a $C_1$–$C_{10}$ aliphatic radical, a $C_3$–$C_8$ cycloaliphatic radical, a $C_6$–$C_{15}$ aromatic radical or a $C_7$–$C_{16}$ araliphatic radical:

$R^x$ and $R^y$ are independently hydrogen, halogen, hydroxy, a $C_1$–$C_{10}$ alkyl, $C_2$–$C_{10}$ alkenyl, $C_3$–$C_8$ cycloalkyl, $C_6$–$C_{15}$ aryl, $C_7$–$C_{16}$ aralkyl, $C_1$–$C_{10}$ alkoxy, $C_2$–$C_{10}$ alkenoxy, $C_6$–$C_{10}$ aryloxy or $C_7$–$C_{16}$ aralkyloxy group, which is substituted or unsubstituted, or —$OCOR^z$;

$R^z$ is a substituted or unsubstituted $C_1$–$C_{10}$ alkyl, $C_2$–$C_{10}$ alkenyl, $C_3$–$C_8$ cycloalkyl, $C_6$–$C_{15}$ aryl or $C_7$–$C_{16}$ aralkyl group; and Z is $C_6$–$C_{10}$ aryloxythiocarbonyloxy, the $C_6$–$C_{10}$ aryl group being substituted or unsubstituted.

2. A oligonucleotide according to claim 1, in which $R^5_a$ and $R^8_a$ are each independently hydrogen, fluorine, chlorine, hydroxy, $C_1$–$C_{10}$ alkoxy, $C_2$–$C_{10}$ alkenoxy, $C_6$–$C_{15}$ aryloxy, $C_7$–$C_{16}$ aralkyloxy, —$OCOR^1$ or silyloxy substituted by three $C_1$–$C_{15}$ hydrocarbyl groups;

$R^6_a$ and $R^7_a$ are each independently a substituted or unsubstituted $C_1$–$C_{10}$ alkyl, $C_2$–$C_{10}$ alkenyl, $C_6$–$C_{15}$ aryl or $C_7$–$C_{16}$ aralkyl group, —$COR^{11}$, —$SO_2R^{11}$ or silyl substituted by three $C_1$–$C_{15}$ hydrocarbyl groups;

$R^9$ is hydrogen, substituted or unsubstituted $C_1$–$C_8$ alkyl, $C_3$–$C_8$ cycloalkyl, $C_6$–$C_{15}$ aryl or $C_7$–$C_{13}$ aralkyl, an alkali metal ion or an ammonium ion; and $R^{10}$ and $R^{11}$ are each independently substituted or unsubstituted $C_1$–$C_{10}$ alkyl, $C_2$–$C_{10}$ alkenyl, $C_3$–$C_8$ cycloalkyl, $C_6$–$C_{15}$ aryl or $C_7$–$C_{16}$ aralkyl.

3. An oligonucleotide according to claim 1, which contains a dinucleotide diradical residue having the formula

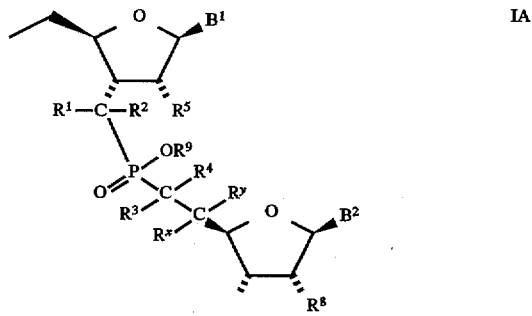

IA where $B^1$, $B^2$, $R^x$, $R^y$ are as defined in claim 2.

4. An oliginucleotide according to claim 1, in which $R^x$, $R^y$, $R^5$ or $R^8$ as alkoxy is $C_1$–$C_4$ alkoxy, $R^x$, $R^y$, $R^5$ or $R^8$ as alkenoxy is $C_3$ or $C_4$ alkenoxy, $R^x$, $R^y$, $R^5$ or $R^8$ as aryloxy is $C_6$–$C_8$ aryloxy, $R^x$, $R^y$, $R^5$ or $R^8$ as $C_7$ to $C_{16}$ aralkyloxy is $C_7$–$C_9$ aralkyloxy and $R^5$ or $R^8$ as tri($C_1$–$C_{15}$ hydrocarbyl)-substituted silyloxy is $C_1$ to $C_6$ alkyl di($C_6$–$C_8$ aryl) silyloxy.

5. A oligonucleotide according to claim 4, in which $R^x$, $R^y$, $R^5$ or $R^8$ as $C_1$–$C_4$ alkoxy is methoxy or ethoxy, $R^x$, $R^y$, $R^5$ or $R^8$ as $C_3$ or $C_4$ alkenoxy is allyloxy or methallyloxy, $R^x$, $R^y$, $R^5$ or $R^8$ as $C_6$–$C_8$ aryloxy is phenoxy, $R^x$, $R^y$, $R^5$ or $R^8$ as $C_7$–$C_9$ aralkyloxy is benzyloxy and $R^5$ or $R^8$ as tri($C_1$–$C_{15}$ hydrocarbyl)-substituted silyloxy is tert-butyldiphenylsilyloxy.

6. A oligonucleotide according to claim 1, in which $R^x$, $R^y$, $R^z$, $R^6$, $R^7$, $R^{10}$ or $R^{11}$ as $C_1$–$C_{10}$ alkyl is $C_1$–$C_4$ alkyl, $R^x$, $R^y$, $R^z$, $R^6$, $R^7$, $R^{10}$ or $R^{11}$ as $C_2$–$C_{10}$ alkenyl is $C_3$–$C_4$ alkenyl, $R^x$, $R^y$, $R^z$, $R^9$, $R^{10}$ or $R^{11}$ as $C_3$–$C_8$ cycloalkyl is $C_6$–$C_8$ cycloalkyl, $R^x$, $R^y$, $R^z$, $R^6$ or $R^7$ as $C_6$–$C_{15}$ aryl is $C_6$–$C_8$ aryl, $R^{10}$ or $R^{11}$ as $C_6$–$C_{15}$ aryl is $C_6$–$C_{10}$ aryl, $R^x$, $R^y$, $R^z$, $R^6$, $R^7$, $R^{10}$ or $R^{11}$ as $C_7$–$C_{16}$ aralkyl is $C_7$–$C_9$ aralkyl and $R^6$ or $R^7$ al tri($C_1$–$C_{15}$ hydrocarbyl)-substituted silyl is $C_1$–$C_6$ alkyldi($C_6$–$C_8$ aryl)silyl.

7. A oligonucleotide according to claim 6, in which $R^x$, $R^y$, $R^z$, $R^6$, $R_7$, $R^{10}$ or $R^{11}$ as $C_1$–$C_4$ alkyl is methyl or ethyl, $R^x$, $R^y$, $R^z$, $R^6$, $R^7$, $R^{10}$ or $R^{11}$ as $C_3$–$C_4$ alkenyl is allyl or methallyl, $R^x$, $R^y$, $R^z$, $R^9$, $R^{10}$ or $R^{11}$ as $C_6$–$C_8$ cycloalkyl is cyclohexyl, $R^x$, $R^y$, $R^z$, $R^6$ or $R^7$ as $C_6$–$C_8$ aryl is phenyl, $R^{10}$ or $R^{11}$ as $C_6$–$C_{10}$ aryl is phenyl, nitrophenyl, or naphthyl, $R^x$, $R^y$, $R^z$, $R^6$, $R^7$, $R^{10}$ or $R^{11}$ as $C_7$–$C_{16}$ aralkyl is benzyl and $R^6$ or $R^7$ as tri($C_1$–$C_{15}$ hydrocarbyl)-substituted silyl is tert-butyldiphenylsilyl.

8. A oligonucleotide according to claim 1, in which $R^9$ as $C_1$–$C_8$ alkyl is $C_1$–$C_6$ alkyl, $R^9$ as $C_7$–$C_{13}$ aralkyl is $C_7$–$C_9$ aralkyl, and $R^9$ as an alkali metal ion is a sodium or potassium ion.

9. A oligonucleotide according to claim 1, in which $B^1$ and $B^2$ are each a monovalent radical of a pyrimidine base, $R^1$ is hydrogen, fluorine, hydroxy or $C_1$–$C_4$ alkyl- or halogen-substituted phenyloxythiocarbonyloxy, $R^2$, $R^3$ and $R^4$ are each hydrogen, $R^5$ is hydrogen, hydroxy or —$OCOR^{10}$ where $R^{10}$ is $C_1$–$C_4$ alkyl or $C_6$–$C_{10}$ aryl, $R^6$ is hydrogen, —$COR^{11}$ where $R^{11}$ is $C_1$–$C_4$ alkyl or $C_6$–$C_{10}$ aryl or alkyldiarylsilyl, or $R^6$ is unsubstituted or $C_1$–$C_4$ alkoxy-substituted $C_7$–$C_{20}$ aralkyl, $R^7$ is hydrogen, benzyl, cyano-$C_1$–$C_4$ alkyl-N,N-di($C_1$–$C_4$)alkylphosphoramidyl, or —$COR^{11}$ where $R^{11}$ is $C_6$–$C_{10}$ aryl, $R^8$ is hydrogen, hydroxy, —$OR^{10}$ where $R^{1-}$ is $C_1$–$C_4$ alkyl or —$OCOR^{10}$ where $R^{10}$ is $C_1$–$C_4$ alkyl or $C_6$–$C_{10}$ aryl, or $R^7O$ and $R^8$ together denote an isopropylidenedioxy group, $R^9$ is hydrogen or unsubstituted or substituted $C_1$–$C_6$ alkyl, and $R^x$ and $R^y$ are independently hydrogen, fluorine, methyl, ethyl or phenyl or $R^y$ is hydrogen, methyl, ethyl or phenyl and $R^x$ is hydroxy, fluorine, methoxy, ethoxy, benzyloxy, acetoxy or benzoyloxy.

10. A oligonucleotide according to claim 9, in which $B^1$ and $B^2$ are each 1-thyminyl, $R^5$ is hydrogen or —$OCOCH_3$, $R^6$ is hydrogen, benzoyl, tert-butyl diphenylsilyl or 4,4¹-dimethoxytriphenylmethyl, $R^7$ is hydrogen, benzyl, 2-cyanoethyl-N,N-diisopropylphosphoramidyl, or —$COR^{11}$ where $R^{11}$ is phenyl, 4-nitrophenyl or alpha-naphthyl, $R^9$ is methyl, ethyl, isobutyl or 2-cyanoethyl, and $R^x$ and $R^y$ are each hydrogen.

11. An oligonucleotide according to claim 1, in which n is a number from 0 to 30 and L is a group —$P(O)O^\ominus$.

12. An oligonucleotide according to claim 1, in which n is 1 to 6.

13. An oligonucleotide according to claim 1, in which U,V, and W are the same or different residues of a natural nucleoside, and at least one of the residues U,V, and W is of formula XXXXII where $B^1$ and $B^2$ are natural nucleoside base radicals.

14. A pharmaceutical composition comprising as active ingredient an oligonucleotide according to claim 1 and a pharmaceutically acceptable carrier.

* * * * *